(12) United States Patent
Rogers et al.

(10) Patent No.: US 10,688,313 B2
(45) Date of Patent: Jun. 23, 2020

(54) ELECTROMAGNETIC RADIATION TARGETING DEVICES, ASSEMBLIES, SYSTEMS AND METHODS

(71) Applicant: ROCOMP GLOBAL, LLC, Houston, TX (US)

(72) Inventors: Charles Brian Rogers, Dunedin, FL (US); Scott David Compton, Houston, TX (US)

(73) Assignee: ROCOMP GLOBAL, L.L.C., Houston, TX (US)

( * ) Notice: Subject to any disclaimer, the term of this patent is extended or adjusted under 35 U.S.C. 154(b) by 182 days.

(21) Appl. No.: 15/887,783

(22) Filed: Feb. 2, 2018

(65) Prior Publication Data
US 2018/0178029 A1 Jun. 28, 2018

Related U.S. Application Data

(63) Continuation of application No. 14/764,564, filed as application No. PCT/US2014/015180 on Jul. 29, 2015, now abandoned.
(Continued)

(51) Int. Cl.
*A61N 5/06* (2006.01)
*A61B 18/24* (2006.01)
(Continued)

(52) U.S. Cl.
CPC .......... *A61N 5/0601* (2013.01); *A61B 18/24* (2013.01); *A61N 5/0624* (2013.01);
(Continued)

(58) Field of Classification Search
CPC .......... A61B 18/00; A61B 18/000053; A61B 18/00404; A61B 18/18; A61B 2018/1861; A61B 2018/1869; A61B 2018/18; A61B 18/20; A61B 2018/2035; A61B 2018/206; A61B 18/22; A61B 2018/2255; A61B 18/24; A61B 18/245; A61B 18/26; A61B 2018/263; A61N 5/06; A61N 5/0601; A61N 2005/0602; A61N 2005/063; A61N 2005/0632; A61N 2005/0643; A61N 2005/0644
(Continued)

(56) References Cited

U.S. PATENT DOCUMENTS 5,165,773 A * 11/1992 Nath .................... G02B 6/0006
362/318
5,267,341 A * 11/1993 Shearin .................. A61B 18/24
385/125
(Continued)

FOREIGN PATENT DOCUMENTS

WO   WO 94-26185   11/1994

*Primary Examiner* — Ahmed M Farah
(74) *Attorney, Agent, or Firm* — The Compton Law Firm, P.C.; Scott D. Compton

(57) ABSTRACT

The present application is directed to devices, assemblies, systems and methods for targeting one or more sites with electromagnetic radiation. The devices, assemblies and systems are operationally configured to transform and convey electromagnetic radiation to one or more targeted sites. The devices, assemblies and systems may also convey one or more fluids or fluid solutions to the one or more targeted sites.

15 Claims, 23 Drawing Sheets

Related U.S. Application Data

(60) Provisional application No. 61/761,702, filed on Feb. 7, 2013, provisional application No. 61/785,817, filed on Mar. 14, 2013, provisional application No. 61/800,455, filed on Mar. 15, 2013.

(51) Int. Cl.
*A61B 18/20* (2006.01)
*A61B 18/00* (2006.01)

(52) U.S. Cl.
CPC .............. *A61B 2018/00404* (2013.01); *A61B 2018/206* (2013.01); *A61B 2018/20355* (2017.05); *A61N 2005/0602* (2013.01); *A61N 2005/063* (2013.01); *A61N 2005/0632* (2013.01); *A61N 2005/0644* (2013.01); *A61N 2005/0664* (2013.01)

(58) Field of Classification Search
USPC .................. 606/7, 13–17; 607/88, 89, 92
See application file for complete search history.

(56) References Cited

U.S. PATENT DOCUMENTS

| | | | | |
|---|---|---|---|---|
| 5,452,395 | A * | 9/1995 | Schichman | G02B 6/032 362/555 |
| 5,673,341 | A * | 9/1997 | Takesue | G01N 21/03 250/227.11 |
| 5,702,432 | A | 12/1997 | Chen et al. | |
| 5,855,203 | A | 1/1999 | Matter | |
| 6,117,128 | A * | 9/2000 | Gregory | A61B 18/24 606/15 |
| 6,908,460 | B2 | 6/2005 | Distefano | |
| 6,986,782 | B2 | 1/2006 | Chen et al. | |
| 7,767,208 | B2 | 8/2010 | Chen | |
| 7,811,281 | B1 | 10/2010 | Rentrop | |
| 7,815,632 | B2 * | 10/2010 | Hayakawa | A61B 17/32037 604/19 |
| 8,109,981 | B2 | 2/2012 | Gertner et al. | |
| 8,932,208 | B2 * | 1/2015 | Kendale | A61B 17/3478 600/176 |
| 9,717,927 | B2 * | 8/2017 | Rogers | A61B 18/24 |
| 9,814,901 | B1 * | 11/2017 | Rogers | A61N 5/0601 |
| 9,827,438 | B2 * | 11/2017 | Johnson | G02B 6/3851 |
| 9,848,952 | B2 * | 12/2017 | Khanna | A61B 18/24 |
| 2003/0114842 | A1 * | 6/2003 | DiStefano | A61B 18/24 606/7 |
| 2004/0142484 | A1 | 7/2004 | Berlin et al. | |
| 2005/0090722 | A1 | 4/2005 | Perez | |
| 2005/0261621 | A1 | 11/2005 | Perez | |
| 2006/0074467 | A1 | 4/2006 | Perez | |
| 2006/0095102 | A1 | 5/2006 | Perez | |
| 2006/0247743 | A1 * | 11/2006 | Hayakawa | A61B 18/20 607/89 |
| 2006/0259101 | A1 | 11/2006 | Perez | |
| 2007/0203550 | A1 | 8/2007 | Perez | |
| 2008/0051736 | A1 | 2/2008 | Rioux et al. | |
| 2008/0167617 | A1 | 7/2008 | Boulanger et al. | |
| 2008/0249517 | A1 * | 10/2008 | Svanberg | A61N 5/0601 606/15 |
| 2009/0112198 | A1 | 4/2009 | Khanna et al. | |
| 2009/0216246 | A1 | 8/2009 | Nita et al. | |
| 2009/0228081 | A1 | 9/2009 | Perez | |
| 2009/0253990 | A1 | 10/2009 | Lieber et al. | |
| 2011/0082526 | A1 | 4/2011 | Rizoiu et al. | |
| 2011/0144630 | A1 * | 6/2011 | Loeb | A61B 18/22 606/16 |
| 2012/0053512 | A1 | 3/2012 | Muse | |
| 2012/0157982 | A1 | 6/2012 | Anderson et al. | |
| 2015/0360048 | A1 * | 12/2015 | Rogers | A61N 5/0624 607/80 |
| 2019/0374684 | A1 * | 12/2019 | Laudenslager | A61L 29/085 |

* cited by examiner

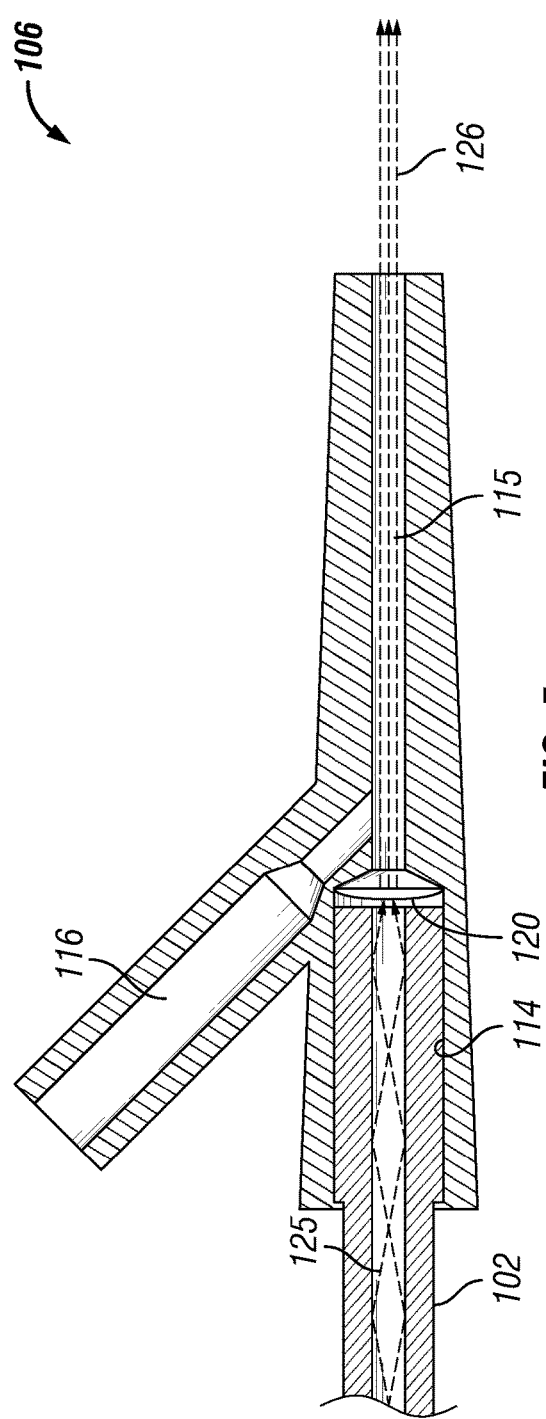
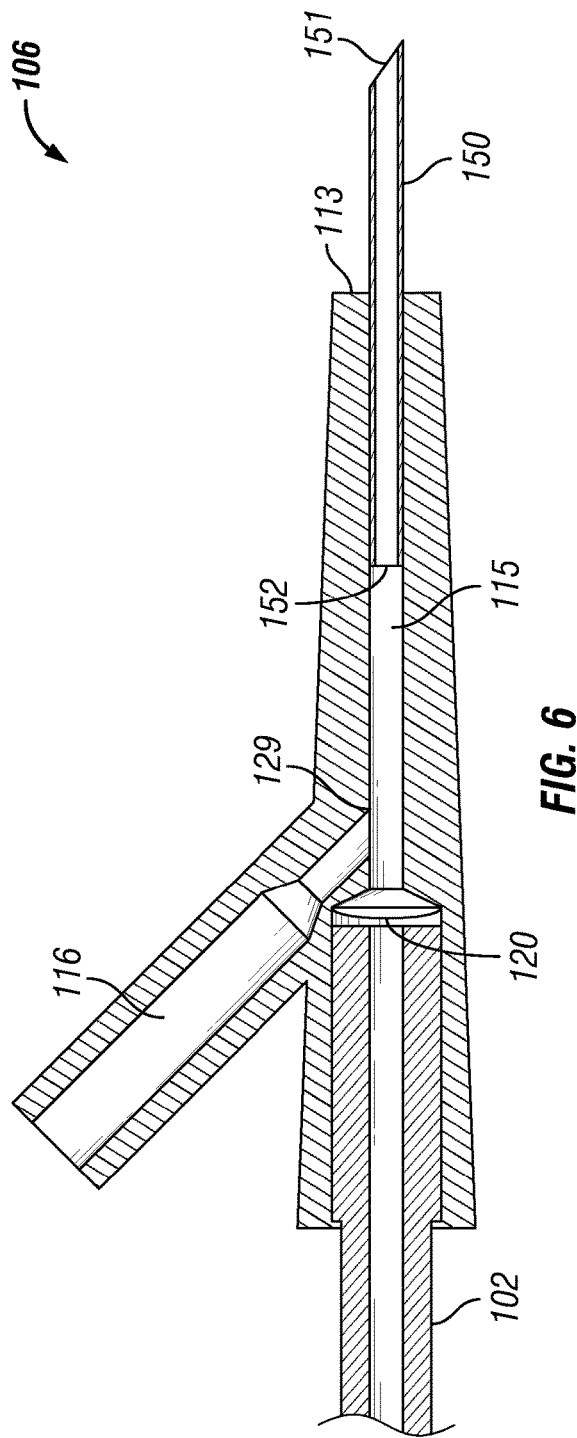
FIG. 5
FIG. 6

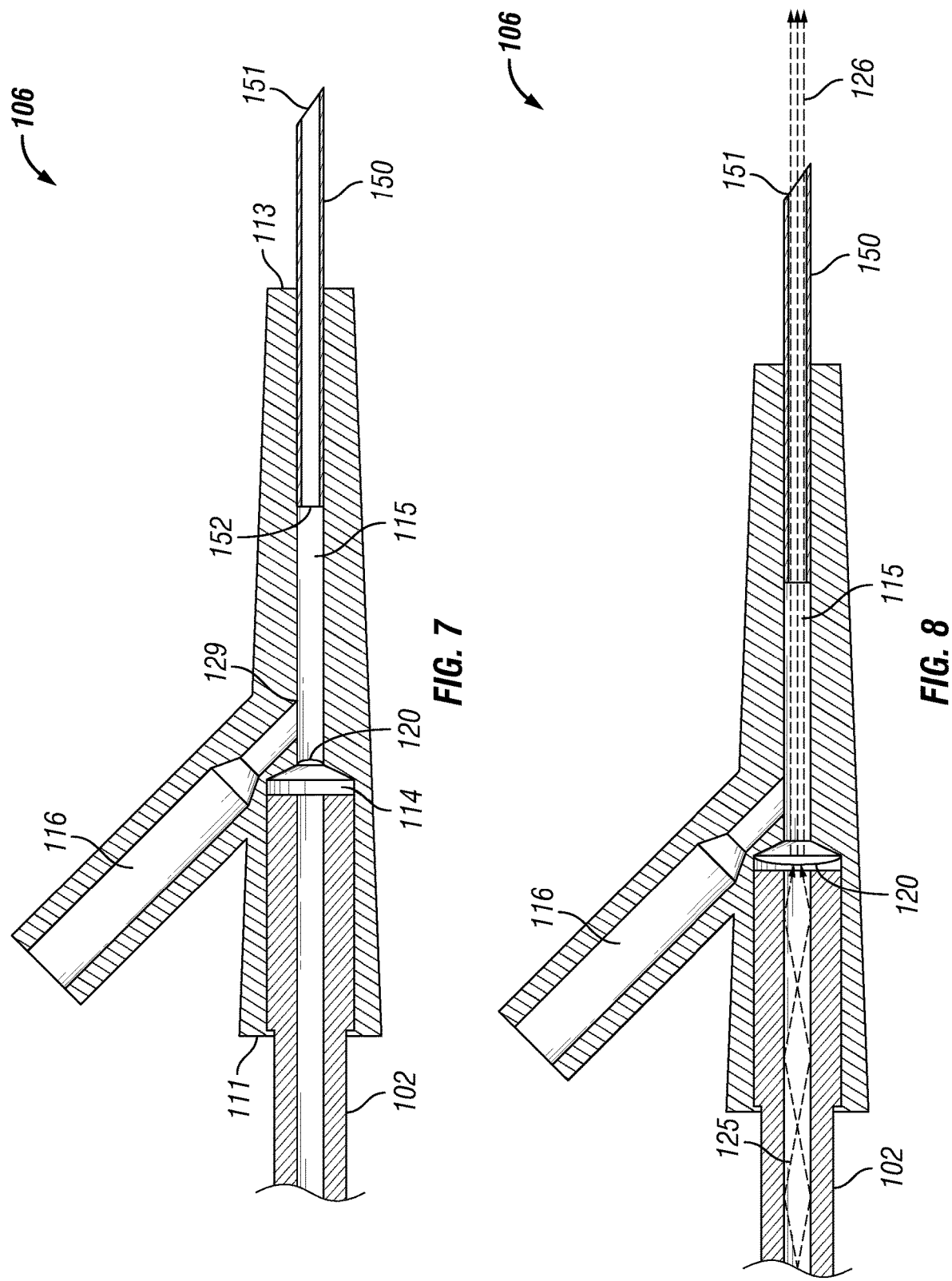

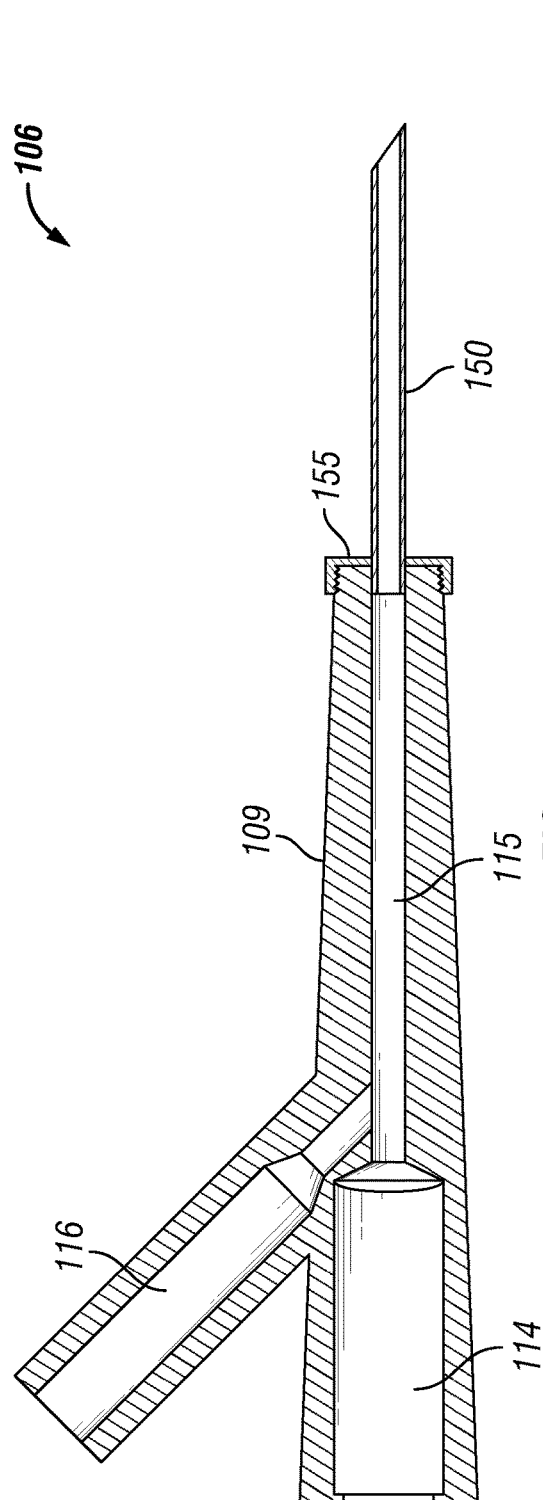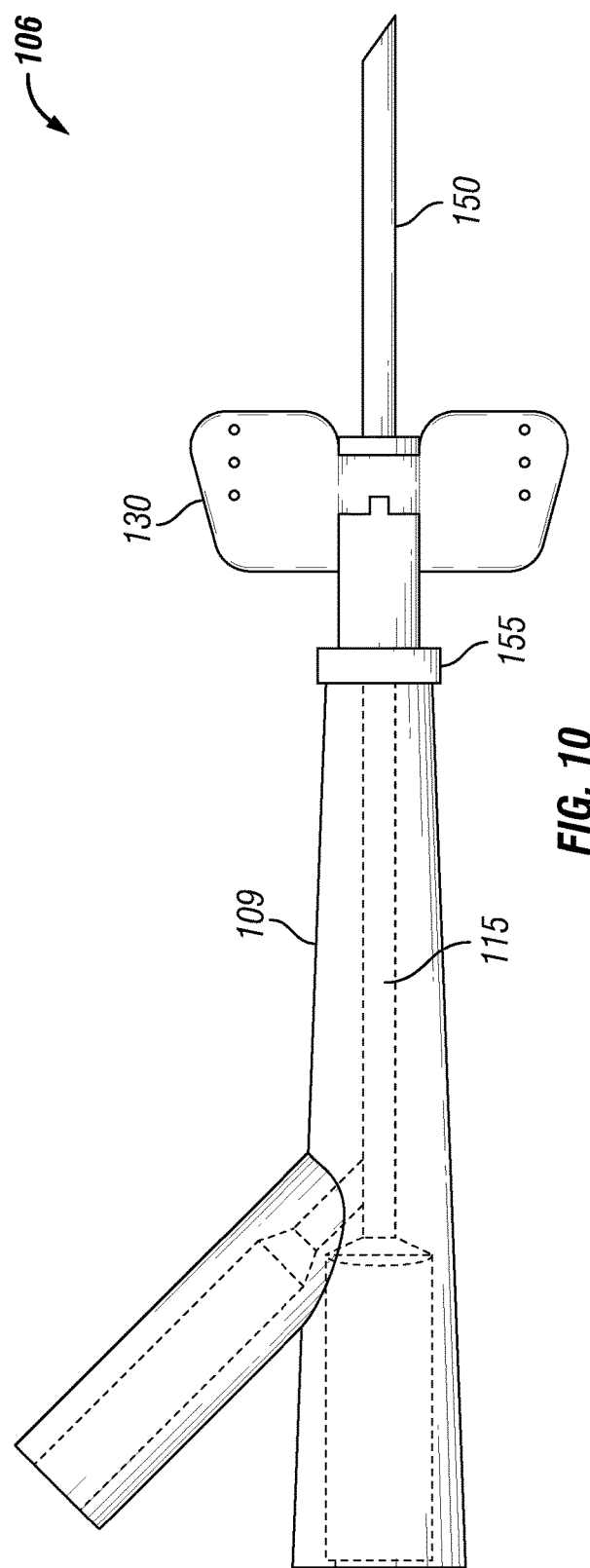

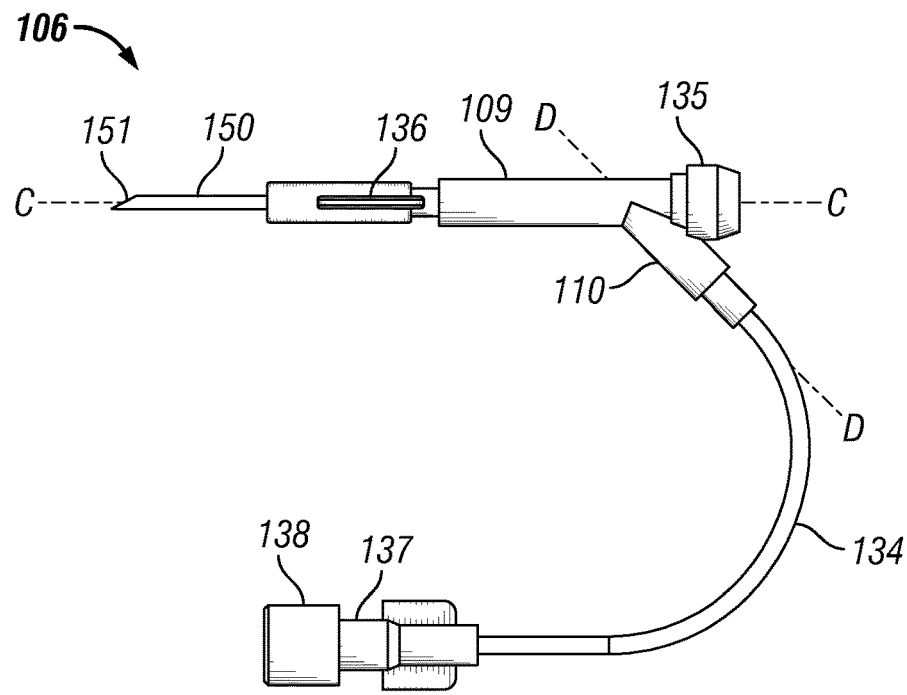
FIG. 14A
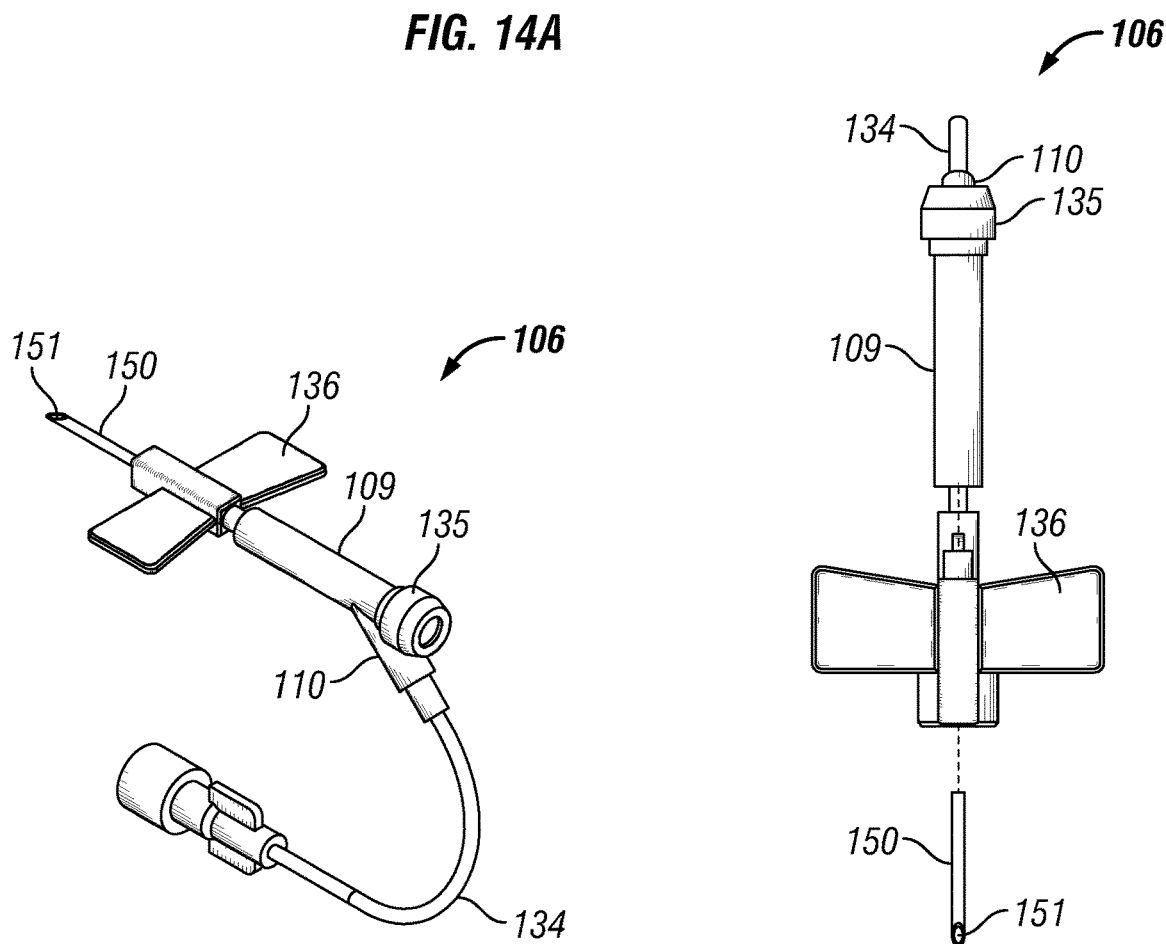
FIG. 14B  FIG. 14C

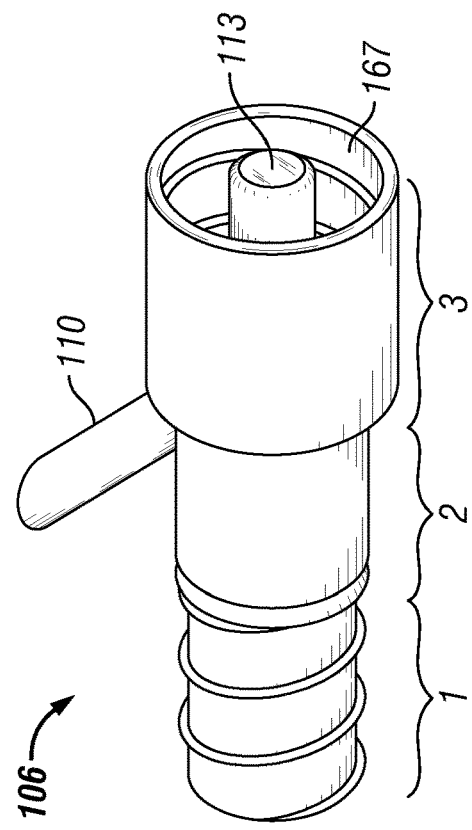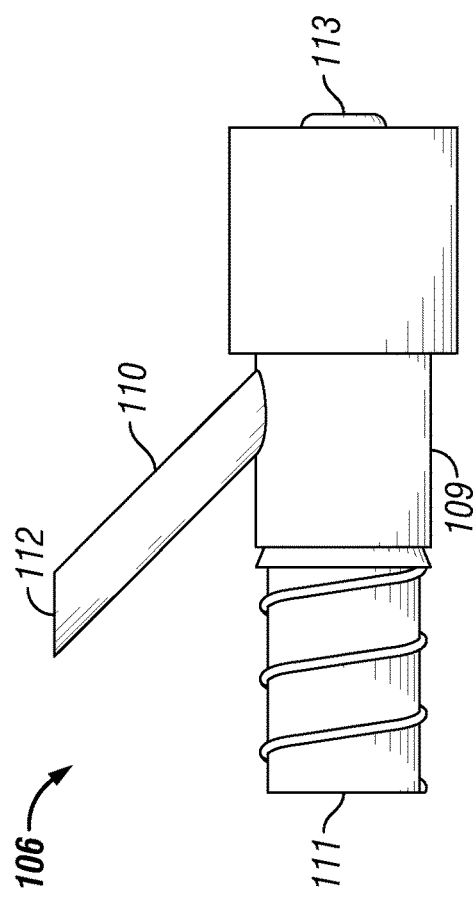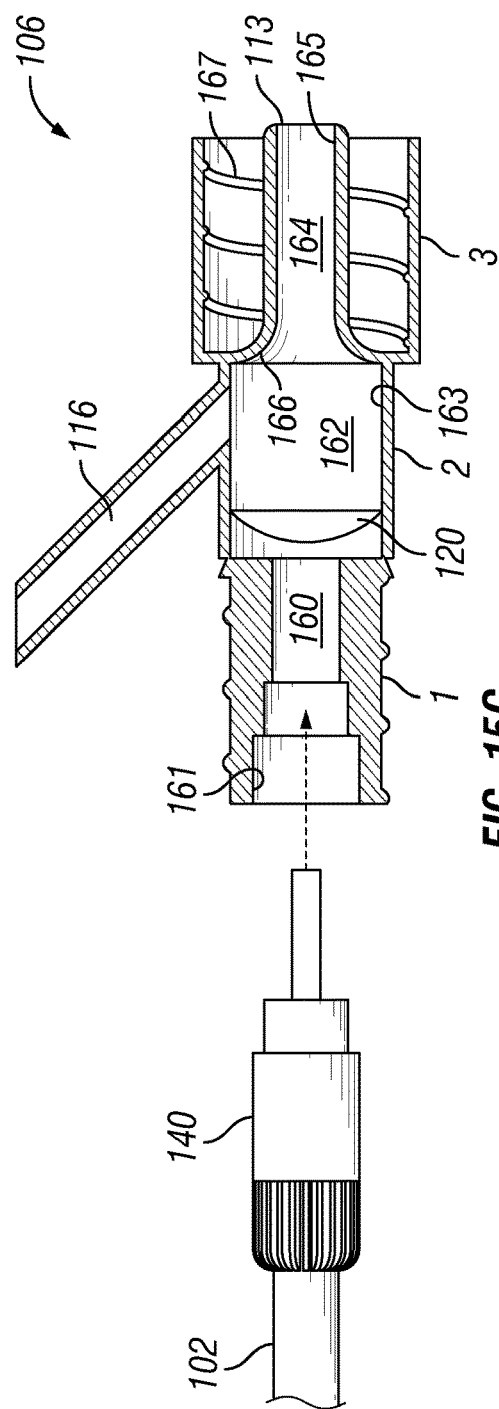

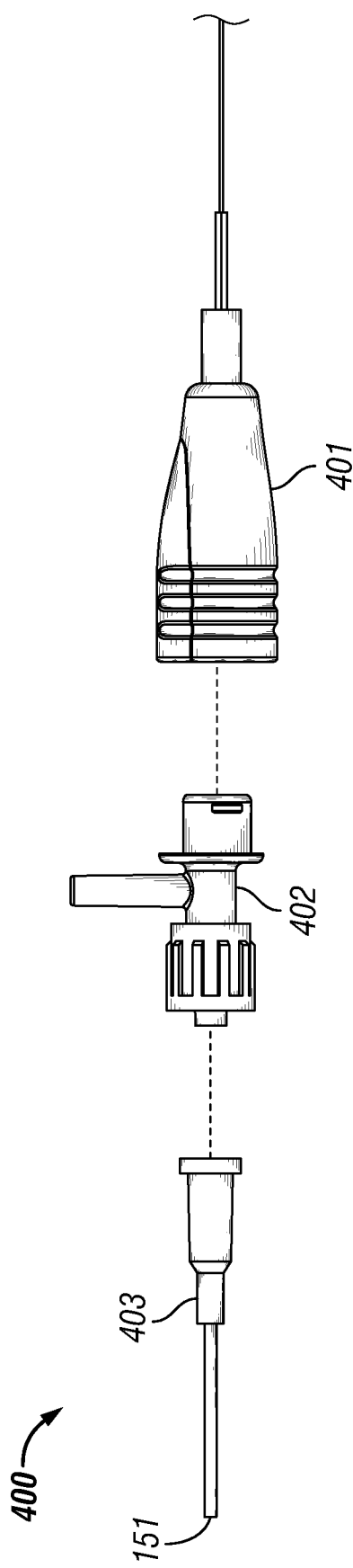
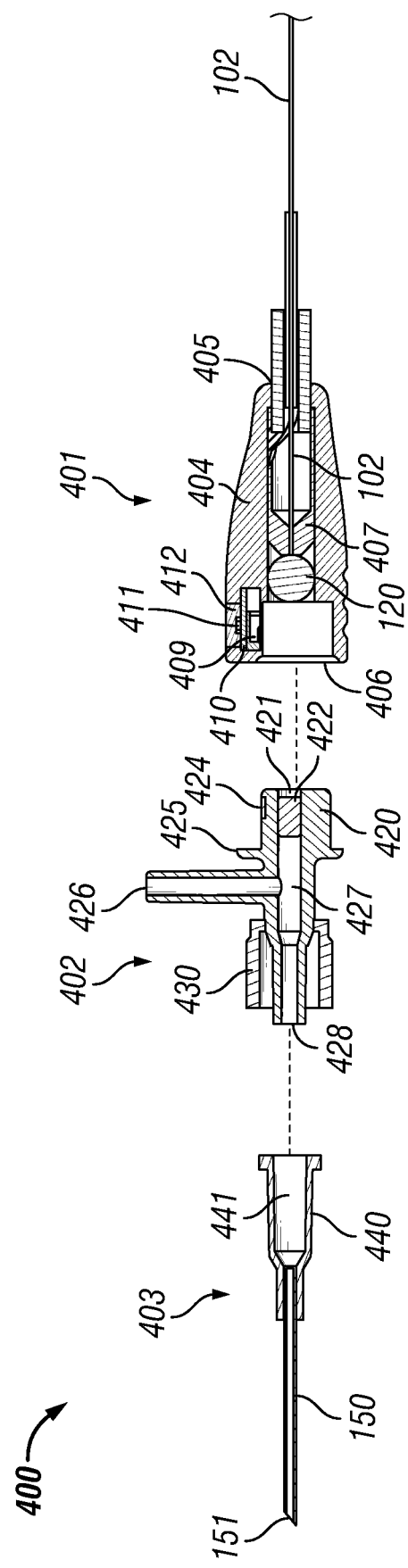
FIG. 27
FIG. 28

ELECTROMAGNETIC RADIATION TARGETING DEVICES, ASSEMBLIES, SYSTEMS AND METHODS

CROSS-REFERENCE TO RELATED APPLICATIONS

This application is a continuation of U.S. patent application Ser. No. 14/764,564, filed on Jul. 29, 2015, which is entitled to the benefit of the filing date of the prior-filed U.S. provisional applications No. 61/761,702, filed on Feb. 7, 2013, No. 61/785,817, filed on Mar. 14, 2013 and No. 61/800,455, filed on Mar. 15, 2013.

STATEMENT REGARDING FEDERALLY SPONSORED RESEARCH OR DEVELOPMENT

Not applicable.

FIELD OF THE APPLICATION

The application relates generally to the conveyance of electromagnetic radiation to target sites such as superficial anatomical locations ("surface locations"), subsurface locations, and internal locations of a subject.

BACKGROUND

Waveguides such as optical fiber have been used to deliver light radiation and light laser energy topically and subcutaneously. Optical fiber, which is made of pure glass (or silica) is subject to breakage. Broken shards of optical fiber contacting an individual may cause injury or result in other undesired consequences. In addition, bodily fluids or other chemicals and foreign substances may contaminate such waveguides.

The emanation of electromagnetic radiation to target sites without contacting the sites or otherwise exposing such sites to breakable materials like optical fiber is desired.

SUMMARY

The present application is directed to device for targeting one or more sites with electromagnetic radiation, the device having a housing operationally configured to (1) receive electromagnetic radiation through a first inlet and fluid through a second inlet, (2) fluidly seal the first inlet from the second inlet and (3) emit the electromagnetic radiation and fluid through a first outlet of the housing.

The present application is also directed to an assembly for targeting electromagnetic radiation at one or more sites including (1) a first member operationally configured to receive electromagnetic radiation therein; (2) a second member attachable to the first member and operationally configured to receive fluid therein; and (3) a third member attachable to the second member, the third member having an outlet operationally configured to emit electromagnetic radiation received by the first member and fluid received by the second member.

The present application is also directed to a system for targeting electromagnetic radiation at one or more sites including (1) an electromagnetic radiation source; (2) a fluid source; (3) a waveguide in radiant communication with the electromagnetic radiation source; and (4) an assembly including (A) a device having a first inlet for receiving electromagnetic radiation from the waveguide, a second inlet for receiving fluid from the fluid source and a first outlet for emitting electromagnetic radiation and fluid received through the first and second inlets, the device being operationally configured to transform electromagnetic radiation received through the first inlet and (B) a hollow member having an open proximal end releasably attachable to the first outlet and an open distal end operationally configured for the emission of electromagnetic radiation and fluid out of the hollow member.

The present application is also directed to a method of targeting an animal blood vessel with electromagnetic radiation including (1) providing an assembly including (A) a device having an inlet for receiving electromagnetic radiation from an electromagnetic radiation source, an inlet for receiving fluid from a fluid source and an outlet for emitting the electromagnetic radiation and fluid, the device being operationally configured to transform the electromagnetic radiation received therein and (B) a hollow puncture forming member attachable to the outlet of the device; (2) connecting the device to an electromagnetic radiation source and a fluid source; (3) directing an open distal end of the hollow puncture forming member into the blood vessel; and (4) conveying electromagnetic radiation and fluid to the device wherein the device transforms the electromagnetic radiation emitting transformed electromagnetic radiation and fluid out through the distal end of the hollow puncture forming member into the blood vessel. The present application is also directed to a method of controlling the propagation of electromagnetic radiation conveyed to one or more target sites by (1) providing a device for conveying electromagnetic radiation and fluid there through to one or more target sites, the device being constructed from one or more materials providing one or more optical properties of the device, the device having a housing including an electromagnetic radiation inlet, a fluid inlet, and an outlet for the electromagnetic radiation and the fluid; and (2) providing one or more fluids to be delivered through the device, the one or more fluids having one or more optical properties.

BRIEF DESCRIPTION OF THE FIGURES

FIG. 5 illustrates a sectional view of the treatment device of FIG. 3 including a waveguide attached thereto.

FIG. 6 illustrates a sectional view of the treatment device of FIG. 3 including a waveguide and hollow member attached thereto.

FIG. 7 illustrates another sectional side view of a simplified embodiment of a treatment device including a waveguide attached thereto.

FIG. 8 illustrates another sectional side view of the treatment device of FIG. 7.

FIG. 9 illustrates another sectional side view of a simplified embodiment of a treatment device.

FIG. 10 illustrates a partial phantom side view of another simplified embodiment of a treatment device.

FIG. 14A illustrates a side view of another embodiment of a treatment device.

FIG. 14B illustrates a perspective view of the embodiment of FIG. 14A.

FIG. 14C illustrates an exploded view of the embodiment of FIG. 14A.

FIG. 15A illustrates a side view of another embodiment of a treatment device.

FIG. 15B illustrates a perspective view of the embodiment of FIG. 15A.

FIG. 15C illustrates a sectional view of the embodiment of FIG. 15A including a waveguide connector.

FIG. 27 illustrates an exploded view of a treatment assembly of the present application.

FIG. 28 illustrates a sectional view of the treatment assembly of FIG. 27.

BRIEF DESCRIPTION

Figure 1:
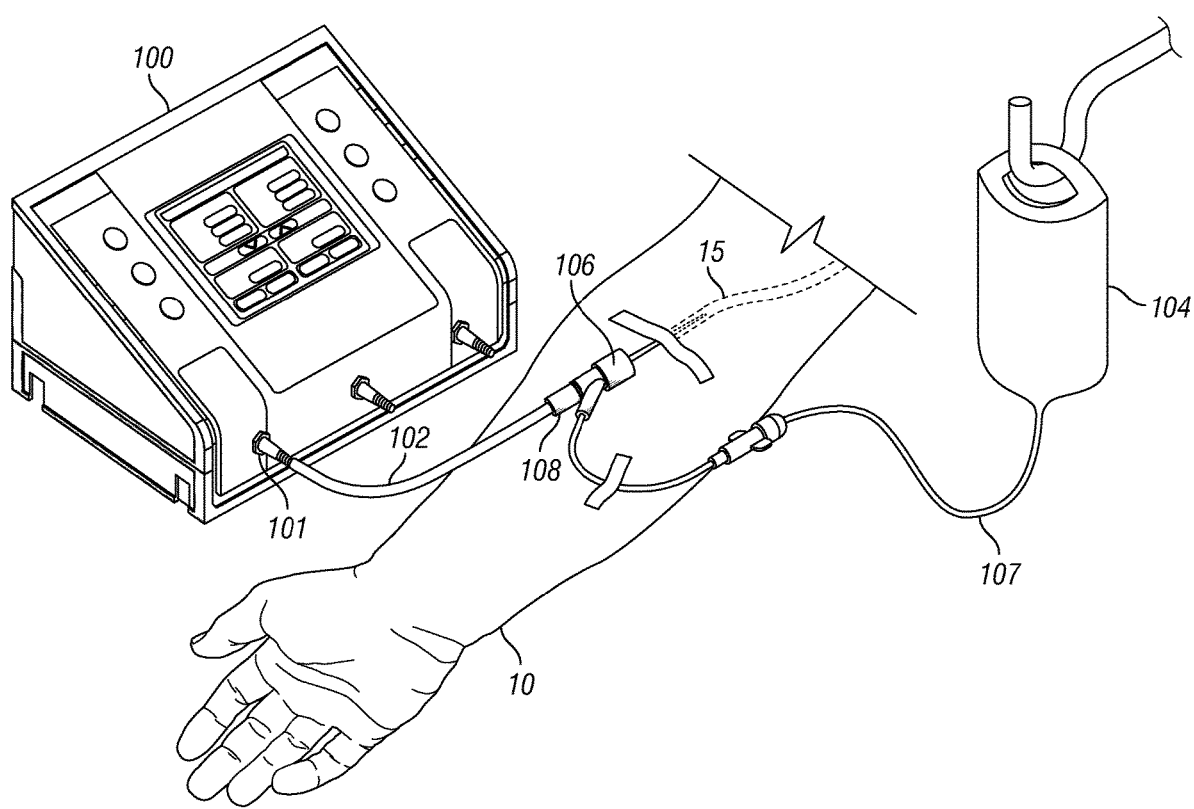
FIG. 1 illustrates a simplified embodiment of a system of this application.

Before describing the invention in detail, it is to be understood that the present device, system and method are not limited to particular embodiments. It is also to be understood that the terminology used herein is for the purpose of describing particular embodiments only, and is not intended to be limiting. As used in this specification and the appended claims, the term "blood contaminant" may refer to one or more viral contaminants, bacterial contaminants, pathogenic organisms, pathogenic microorganisms, toxins, organisms, poisons, abnormal cells, allergens, other agents, and combinations thereof. Herein, "toxin" or "toxins" may be characterized and include one or more neurotoxins, hemotoxins, phototoxins, exotoxins, endotoxins, biotoxins, man-made toxins, and combinations thereof. The phrase "pathogenic organism" or "pathogen" herein refers to any particle and/or organism that can enter the body of a living subject including, but not necessarily limited to microorganisms such as bacteria, viruses, fungi, protozoa, multicellular parasites, and aberrant proteins ("prions"), and combinations thereof. In terms of animals, the phrase "blood-borne pathogen" herein refers to one or more infectious microorganisms present in an animal's blood that may cause sickness, disease or other abnormal state in an animal. A "blood-borne disease" means a disease that can be spread through contamination of the blood and/or blood components and/or cellular blood matter and/or blood plasma protein fractions of an animal. In particular, a blood-borne disease may refer to any disease of the blood, involving the red blood cells (erythrocytes), white blood cells (leukocytes), or platelets (thrombocytes) or the tissues in which these elements are formed, e.g., the bone marrow, lymph nodes, spleen. The phrase "emerging infectious disease" ("EID") refers to an infectious disease whose incidence has increased in recent years with prospects of continual increasing. As understood by persons of ordinary skill in the art, EIDs are caused by newly identified species or strains, e.g., severe acute respiratory syndrome ("SARS") and acquired immune deficiency syndrome ("AIDS"), which (1) may have evolved from a known infection, e.g. influenza, or (2) spread to a new population, e.g., West Nile virus, or area undergoing ecologic transformation, e.g., Lyme disease, or be reemerging infections, like drug resistant tuberculosis. The phrase "infectious disease" (also referred to as "transmissible diseases" and/or "communicable diseases") suitably includes a clinically evident illness, i.e., characteristic medical signs and/or symptoms of disease, resulting from the infection, presence and growth of pathogenic biological agents in an individual host organism.

Herein, a "blood infection" may be referred to as a condition wherein the blood cells and/or blood plasma get infected by one or more pathogens and their toxins. When referring to blood infections, the term "sepsis" refers to a condition where the entire body is involved in a toxic condition with microorganisms and their toxins spreading from one site to another. The term "septicemia" refers to a condition where there are active pathogens present in the bloodstream itself. A "blood disorder" refers to conditions that are mostly genetic and non-contagious in nature. The phrase "blood constituent" may refer to red blood cells and/or blood platelets and/or blood plasma. The phrase "cellular blood constituent" may refer to red blood cells and/or blood platelets. The phrase "blood product" may refer to one or more blood constituents either alone or in combination, and either with or without other blood constituents or other substances. Thus, blood products may include for example, whole blood and blood plasma.

Blood-borne pathogens may be transferred to an animal via inhalation, direct contact with contaminated blood or fluid(s) of another animal. Depending on the animal in question, pathogens may be transferred through open sores, cuts, abrasions, acne, blisters, sun-damaged skin, mucous membranes of the eyes, mucous membranes of the mouth, mucous membranes of the nose, mucous membranes of the genital area, mucous membranes of the anus, and combinations thereof. Exemplary animal fluids may include, but are not necessarily limited to animal semen, animal secretions, cerebrospinal fluid, synovial fluid, pleural fluid, peritoneal fluid, amniotic fluid, saliva, and combinations thereof. The phrase "vector-borne disease" refers to a disease caused by an infectious microbe that is transmitted to animals by arthropods. The arthropods, e.g., insects or arachnids, may include but are not necessarily limited to (1) blood sucking insects such as mosquitoes, fleas, lice, biting flies and bugs and (2) blood sucking arachnids such as mites and ticks. The term "vector" may refer to any arthropod that transmits a disease through feeding activity. Herein, blood-borne pathogens may be blood-borne, vector borne, or otherwise transferred to an animal by other intentional and unintentional means including, for example, via transfusion of human blood products. Herein, the term microorganism may include, but is not necessarily limited to one or more microscopic disease-causing organisms.

"Electromagnetic radiation," as understood by a skilled artisan, is classified by wavelength into radio, microwave, infrared, the visible spectrum perceived as visible light, ultraviolet ("UV"), X-rays, and gamma rays. The phrase "radiant energy" refers to the energy of electromagnetic waves. The phrase "optical property" refers to any fundamental property of a material that affects its interaction with electromagnetic energy. Optical properties may include, but are not necessarily limited to optical transmission, optical absorption, index of refraction, reflectivity, non-linear effects, and scattering. The term "transparent" can be defined to include the characterization that no significant obstruction or absorption of electromagnetic radiation occurs at the particular wavelength or wavelengths of interest. Herein, the term "treatment" refers to the delivery of electromagnetic radiation to one or more target sites of one or more subjects. A "target site" may include one or more superficial or surface sites and/or subsurface sites of a subject. The term "subject" or "target subject" refers to a target entity, entities, object or objects of the electromagnetic radiation. Exemplary subjects may include one or more (1) inanimate objects, (2) organisms of the three domains (Archaea, Eubacteria and Eukaryota) and six kingdoms (Archaebacteria, Eubacteria, Protista, Fungi, Plantae, and Animalia), (3) individual cells and cellular components of the three domains and six kingdoms including cell cultures, (4) blood products, (5) fluids or fluid compositions, and combinations thereof. Suitable inanimate objects may include but are not necessarily limited to inorganic compounds, organic compounds, compositions thereof and articles of construction made there from. Herein, "DNA" refers to deoxyribonucleic acid and "RNA" refers to ribonucleic acid as understood by persons of ordinary skill in the art of science and medicine.

The term "skin" may refer to the topical surface of members of the Animalia kingdom. With regard to mammals, the term "skin" refers to the epidermis and/or dermis of an animal. The epidermis is comprised of the stratum corneum, the stratum granulosum, the stratum spinosum, and the stratum basale, with the stratum corneum being at the surface of the skin and the stratum basale being the deepest portion of the epidermis. The epidermis ranges from about 0.05 mm to about 0.2 mm in thickness, depending on the location on the body of the mammal. Beneath the epidermis is the dermis, which is significantly thicker than the epidermis ranging from about 0.3.0 mm to about 3.0 mm in thickness, depending on the location on the body of the mammal. The dermis is primarily composed of collagen in the form of fibrous bundles. Herein, the term "subcutaneous" may refer to being, living, occurring, or administered under the skin. The term "topical" refers to any external or outer surface locations of a target subject. The phrases "blood vessel" and "blood vessels" may refer to veins and/or arteries as each is understood by persons of ordinary skill in the art of circulatory systems of animals. The term "intravenous" may refer to being situated, performed, occurring within, administered into, or involving entry by way of a vein. The term "intra-arterial" may refer to being situated, performed, occurring within, administered into, or involving entry by way of an artery.

Herein, the phrase "hollow puncture forming member" refers to an object operationally configured to penetrate and/or puncture (1) inanimate material(s) and (2) dead and/or live tissue of an animal via subcutaneous injection into veins, arteries, and other subcutaneous areas or spaces. One suitable hollow puncture forming member includes a cannula, as the term is understood by persons of ordinary skill of the art of medicine. Another suitable hollow puncture forming member includes a needle, including a hypodermic needle as understood by persons of ordinary skill in the art of medicine. Another suitable hollow puncture forming member includes a catheter or flexible catheter tube. Another suitable hollow puncture forming member includes a liquid light guide. In one suitable embodiment, the hollow puncture forming member of the present application is operationally configured to act as a waveguide to convey (1) electromagnetic radiation and/or (2) one or more fluids there through. In one implementation, fluids may include water, saline solution or other medicinal solutions. Fluids may also include one or more therapeutic agents including, but not necessarily limited to hydrogen peroxide, vitamins, minerals, pharmaceutical drugs including photo-active drugs, herbs, herbal medicinal products, nutrients (lipids, carbohydrates, proteins), and combinations thereof there through. In one particular embodiment, therapeutic agents may include one or more cell populations, such as a cell population comprising stem cells, chemicals, compounds, chemotherapeutic agents, proteins, nucleic acids such as DNA and RNA, other natural nucleic acids, modified nucleic acids, DNA or nucleic acid aptamers, and combinations thereof. In another embodiment, therapeutic agents may include a DNA that encodes an immunogen (such as a viral antigen, like hepatitis C virus (HCV), hepatitis B virus (HBV), human immunodeficiency virus (HIV), influenza, Japanese encephalitis virus (JEV), human papilloma virus (HPV), or a parasite antigen, such as a malaria antigen, or a plant antigen, such as birch antigen, or a bacterial antigen, such as a staphylococcal or anthrax antigen, or a tumor antigen). As such, the hollow puncture forming member of the present application is operationally configured to convey or otherwise allow passage of electromagnetic radiation and/or one or more pharmaceutically acceptable solutions or fluids there through. Therapeutic agents of this application may also include one or more selective release agents as desired.

Herein, "pharmaceutical drug," "drug" or "pharmaceutical" may refer to any chemical substance intended for use in the medical diagnosis, cure, treatment, or prevention of disease. The phrase "herbal medicinal product" may refer to any medicinal product, exclusively containing as active ingredients one or more herbal substances or one or more herbal preparations, or one or more such herbal substances in combination with one or more such herbal preparations. The phrase "active agent" may be defined herein to mean a therapeutic agent given to a target subject to elicit a desired effect.

In one aspect, the application provides a waveguide and/or waveguide assembly operationally configured to be inserted or injected into a target subject as desired. In another embodiment, the application provides a waveguide, including but not necessarily limited to an injectable waveguide operationally configured to receive and emit electromagnetic radiation there from. In still another embodiment, the application provides a photon transmitting waveguide including but not necessarily limited to an injectable waveguide. In still another embodiment, the application provides a waveguide configured to operate in a manner similar as a liquid light guide receiving radiant energy from another waveguide such as an optical fiber and conveying the same to a target site.

In another aspect, the application provides a device, assembly, system and method for employing transformation optics for the delivery of electromagnetic radiation to one or more target sites.

In another aspect, the application provides a device, assembly, system and method for the delivery of electromagnetic radiation and a therapeutic amount of one or more fluids to one or more subcutaneous target sites. The device, assembly, system may also be operationally configured to deliver electromagnetic radiation and a therapeutic amount of hydrogen peroxide to one or more subcutaneous target sites. For purposes of this application, hydrogen peroxide may be used to boost oxygen levels of a target animal subject. In another aspect, ozone blood infusion techniques may also be employed via the device, assembly, system and method of this application.

In another aspect, the application provides transformation optics for targeting electromagnetic radiation. Employing transformation optics, a device, assembly and/or system of this application is suitably operationally configured to convey electromagnetic radiation to a removable hollow puncture forming member in radiant communication thereto. In another implementation, a device, assembly, and/or system employing transformation optics may necessarily include a hollow puncture forming member into the physical design of the device or assembly.

In another aspect, the application provides an injectable parallel radiant energy forming device positioned to transform electromagnetic radiation generated by one or more light sources into substantially parallel beams of electromagnetic radiation. In another aspect, the application provides an injectable collimator. In one embodiment, the injectable collimator may be coupled to a fiber optic cable, which in turn may be coupled to a light source. In another aspect, the application provides an injectable liquid light guide and collimator assembly. In another aspect, the application provides an injectable collimator operationally configured to collimate electromagnetic radiation received from a waveguide or radiant conduit to a specified beam diameter or spot size. A spot size down to a few microns may be achieved as desired.

In another aspect, the application provides an injectable collimator operationally configured to adjust the focal length of the optical interface as desired, e.g., according to varying wavelengths of electromagnetic radiation received by the collimator.

In another aspect, the application provides a device, assembly, system and method for the emanation of electromagnetic radiation upon one or more targets. In another aspect, the application provides a device, assembly, system and method for the emanation of electromagnetic radiation to one or more blood products housed in one or more containers—sealed and/or unsealed. In another aspect, the application provides a device, assembly, system and method for the emanation of electromagnetic radiation to a target fluid housed in an open container, sealed container or otherwise closed container. In another aspect, the application provides a device, assembly, system and method for the emanation of electromagnetic radiation upon one or more fluids or fluid solutions housed in an open container or a sealed container. In another aspect the application provides a device, assembly, system and method operationally effective to sterilize the one or more fluids or fluid solutions. In another aspect, the application provides a device, assembly, system and method for the emanation of electromagnetic radiation upon a volume of water and/or one or more water based solutions.

In another aspect, the application provides a device, assembly, system and method for the emanation of electromagnetic radiation to one or more subcutaneous artificial conduits including, but not necessarily limited to an arteriovenous ("A-V") graft and the like. In another aspect, the application provides a device, assembly, system and method for the emanation of electromagnetic radiation to one or more fluid storage containers, e.g., a bag or other container housing fluid, including but not necessarily limited to animal fluid. Thus, it is contemplated that the device, assembly, system and method may be used to treat blood prior to transfusion procedures and the like, pre-surgery, intra-surgery, post-surgery. The device, assembly, system may also be employed to emanate electromagnetic radiation subcutaneously pre-surgery, intra-surgery, post-surgery as desired.

In another aspect, the application provides a device, assembly, system and method for the emanation of electromagnetic radiation upon one or more target locations in a manner effective to provide for non-ablating emanation of electromagnetic radiation. In another aspect, the application provides a device, assembly, system and method for the emanation of electromagnetic radiation upon one or more target locations of a subject without evaporation and/or sublimation of target material and/or target fluid of the target subject.

In another aspect, the application provides a device, assembly, system and method for the non-destructive emanation of electromagnetic radiation upon one or more target locations of a subject. In one implementation, radiant energy may be employed for selective destruction of one or more target blood contaminants in-vitro and/or in-vivo.

In another aspect, the application provides a device, assembly, system and method for the emanation of electromagnetic radiation upon one or more targets via an injectable collimator. The collimator may include one or more inlets for receiving electromagnetic radiation and one or more outlets for emitting electromagnetic radiation out there from. In one embodiment, the one or more inlets may have a larger diameter than one or more outlets or vice versa. In another embodiment, the outlets and inlets may be substantially equal in size. In another embodiment, the waves of electromagnetic radiation exiting an outlet may be narrowed. To "narrow" electromagnetic radiation may mean either to cause the directions of motion of the electromagnetic radiation to become more aligned in a specific direction, e.g., collimated or parallel, or to cause the spatial cross section of the electromagnetic radiation to become smaller.

In another aspect, the application provides a delivery member operationally configured to guide, transmit or otherwise convey electromagnetic radiation to one or more subsurface sites of a target subject. In another aspect, the application provides a waveguide operationally configured to guide or otherwise convey transformed electromagnetic radiation to one or more subsurface sites of a target subject. In another aspect, the application provides a waveguide operationally configured to guide or otherwise convey collimated electromagnetic radiation to one or more subsurface sites of a target subject. In another aspect, the application provides a waveguide operationally configured to guide or otherwise convey transformed electromagnetic radiation and one or more fluids to one or more subsurface sites of a target subject.

In another aspect, the application provides a waveguide operationally configured to guide, transmit or otherwise convey electromagnetic radiation to one or more subcutaneous sites of a target subject. In another aspect, the application provides a waveguide operationally configured to guide, transmit or otherwise convey transformed electromagnetic radiation to one or more subcutaneous sites of a target subject. In another aspect, the application provides a waveguide operationally configured to guide, transmit or otherwise convey collimated electromagnetic radiation to one or more subcutaneous sites of a target subject. In another aspect, the application provides a waveguide operationally configured to guide or otherwise convey transformed electromagnetic radiation and one or more fluids to one or more subcutaneous sites of a target subject.

In another aspect, the application provides a device, assembly, system and method operationally configured for the postoperative conveyance of electromagnetic radiation to a subcutaneous site of a target subject and/or to a site external a target subject including, but not necessarily limited to one or more containers housing one or more fluids— fluids of a patient and/or other fluids.

In another aspect, the application provides a waveguide, waveguide assembly, or device insertable into the vascular system of a target subject for guiding, transmitting or otherwise conveying electromagnetic radiation to one or more vascular system sites. In still another aspect, the application provides a waveguide, waveguide assembly, or device insertable into the vascular system of a target subject for guiding, transmitting or otherwise conveying electromagnetic radiation and/or one or more fluids to one or more vascular system sites.

In another aspect, the application provides a waveguide, waveguide assembly, system and method for selective delivery of electromagnetic radiation to tissue of animal at one or more surface locations and/or subsurface locations including, but not necessarily limited to internal tissue locations, the lumens of the body, internal structures of animal bone, and combinations thereof. Internal tissue locations may include intramuscular and/or internal organ locations.

In another aspect, the application provides a waveguide, waveguide assembly, system and method for intravenous and/or intra-arterial emanation of electromagnetic radiation.

In another aspect, the application provides a waveguide operationally configured to guide or otherwise convey transformed electromagnetic radiation, including but not necessarily limited to collimated electromagnetic radiation, to one or more target sites of a subject.

In another aspect, the application provides a waveguide operationally configured to provide intravenous and/or intra-arterial delivery of transformed electromagnetic radiation. In another aspect, the application provides a waveguide assembly operationally configured for intravenous and/or intra-arterial delivery of collimated electromagnetic radiation. In another aspect, the application provides a waveguide assembly operationally configured for intravenous and/or intra-arterial delivery of transformed electromagnetic radiation and one or more fluids.

In another aspect, the application provides a method of guiding electromagnetic radiation to one or more target sites of a subject. In another aspect, the application provides a method of guiding electromagnetic radiation to a subsurface or a subcutaneous site of a target subject.

In another aspect, the application provides a method of guiding or otherwise conveying collimated electromagnetic radiation to one or more sites of a target subject. In another aspect, the application provides a method of guiding or otherwise conveying collimated electromagnetic radiation to one or more subsurface and/or subcutaneous sites of a target subject.

In one aspect, the application provides a waveguide comprising transformation optics, the waveguide being operationally configured for intravenous and/or intra-arterial delivery of electromagnetic radiation. In another aspect, the application provides a device, assembly, system and method for the intravenous and/or intra-arterial delivery of electromagnetic radiation and one or more anti-coagulants.

In another aspect, the application provides a hypodermic waveguide. In another aspect, the application provides a hypodermic waveguide assembly. In another aspect, the application provides a hypodermic liquid light guide.

In another aspect, the application provides a waveguide operationally configured to penetrate a target subject for guiding or otherwise conveying electromagnetic radiation to a penetrated site within a target subject. In another aspect, the application provides a waveguide assembly operationally configured to penetrate a target subject for guiding or otherwise conveying electromagnetic radiation to a penetrated site within a target subject. In another aspect, the application provides a system including a delivery member operationally configured to penetrate a target subject for guiding or otherwise conveying electromagnetic radiation to a penetrated site within a target subject.

In another aspect, the application provides a waveguide operationally configured to guide or otherwise convey electromagnetic radiation into a target subject. In another aspect, the application provides a waveguide assembly operationally configured to guide or otherwise convey electromagnetic radiation into a target subject. In another aspect, the application provides a system including a waveguide device or assembly comprising transformation optics, the waveguide device or assembly being operationally configured to guide or otherwise convey electromagnetic radiation to or into a target subject.

In another aspect, the application provides a waveguide device or assembly including transformation optics and a penetrable liquid light guide operationally configured to guide or otherwise convey electromagnetic radiation and one or more fluids to one or more sites of a target subject. In another aspect, the application provides a system including a waveguide assembly including transformation optics and a penetrable liquid light guide operationally configured to guide or otherwise convey electromagnetic radiation received from one or more sources and one or more fluids received from one or more sources to one or more sites of a target subject.

In another aspect, the application provides an assembly including transformation optics operationally, the assembly being configured to convey electromagnetic radiation to one or more subsurface sites of a target subject. In another aspect, the application provides an assembly including transformation optics, the assembly being operationally configured to convey electromagnetic radiation to one or more subcutaneous sites of a target subject.

In one aspect, the application provides a liquid light guide assembly operationally configured to receive radiant energy and one or more fluids and deliver radiant energy and fluids to a target site of subject. In one aspect, the application provides a liquid light guide assembly operationally configured to receive radiant energy and one or more fluids and deliver radiant energy and fluids to a subcutaneous site of subject.

In one aspect, the application provides a waveguide assembly for injecting electromagnetic radiation and/or one or more fluids into a target subject. In another aspect, the application provides a waveguide for injecting electromagnetic radiation and/or one or more therapeutic agents into a target subject.

In one aspect, the application provides a device, assembly, system and method for guiding, transmitting, or otherwise conveying electromagnetic radiation received from a source of electromagnetic radiation to a target site—the device and/or assembly being operationally configured to transform the electromagnetic radiation received from the source. The source of electromagnetic radiation is operationally configured to produce radiation across the entire electromagnetic spectrum.

In one aspect, the application provides a device, assembly, system and method for guiding, transmitting, or otherwise conveying electromagnetic radiation in the optical spectrum to one or more target sites.

In one aspect, the application provides a device, assembly, system and method for transforming electromagnetic radiation prior to the electromagnetic radiation reaching one or more target sites.

In one aspect, the application provides a device, assembly, system and method for conveying electromagnetic radiation to one or more target sites of a subject. In one simplified implementation, the application provides a device operationally configured to receive electromagnetic radiation at an inlet and convey the electromagnetic radiation out through an outlet, the device being operationally configured to transform, manipulate or otherwise affect the electromagnetic radiation prior to its exiting out through the outlet.

In another aspect, the application provides a device, assembly, system and method for conveying electromagnetic radiation from one or more waveguides through one or more optical interfaces prior to the electromagnetic radiation being conveyed out through a hollow member to one or more target sites of a subject.

In another aspect, the application provides a device, assembly, system and method for conveying electromagnetic radiation from one or more waveguides through one or more optical interfaces prior to the electromagnetic radiation being conveyed out through a hollow member to a target site of a subject. In another aspect, the application provides a device, assembly, system and method for conveying electromagnetic radiation from one or more waveguides through one or more optical interfaces prior to the electromagnetic radiation being conveyed out through a hollow puncture forming member to a target site of a subject.

In another aspect, the application provides a device, assembly, system and method for conveying electromagnetic radiation to one or more subcutaneous sites of a subject.

In another aspect, the application provides a device, assembly, system and method for conveying electromagnetic radiation to one or more dermal sites of a subject.

In another aspect, the application provides a device, assembly, system and method for conveying electromagnetic radiation to one or more epidermal sites of a subject.

In another aspect, the application provides a device, assembly, system and method for conveying electromagnetic radiation to one or more topical sites of a subject.

In another aspect, the application provides a device, assembly, system and method for collective targeting of organisms including a host organism and one or more parasite organisms with electromagnetic radiation. In another aspect, the application provides a liquid light guide assembly for collective targeting of organisms including a host organism and one or more parasite organisms with electromagnetic radiation.

In another aspect, the application provides a device, system and method for collective targeting of organisms including a host organism and one or more mutual or commensal symbionts with electromagnetic radiation. In another aspect, the application provides a liquid light guide assembly for collective targeting of organisms including a host organism and one or more mutual or commensal symbionts with electromagnetic radiation.

In another aspect, the application provides a device, assembly, system and method for collective targeting of two or more organisms on or within a host organism with electromagnetic radiation.

In another aspect, the application provides a device, assembly, system and method for conveying electromagnetic radiation to one or more subsurface sites of a subject.

In another aspect, the application provides a device, assembly, system and method for conveying electromagnetic radiation to one or more subcutaneous sites of a subject. In particular, one or more sources of electromagnetic radiation and one or more sources of one or more fluids or fluid solutions, each of which is in communication with one or more hollow members or hollow tubular members operationally configured to convey the electromagnetic radiation and fluid to one or more target sites, e.g., subcutaneous sites. In the device, assembly and hollow member or hollow tubular member, the fluid acts as an electromagnetic waveguide for the electromagnetic radiation propagating there through. In one embodiment, the hollow member or hollow puncture forming member has a high index core surrounded by a low index, i.e., index of refraction, cladding. In such embodiment, the one or more fluid or fluid solutions employed, e.g., a saline solution, acts as the core and the hollow member acts as the cladding as the terms are understood in the art of waveguides. It is also contemplated that the hollow member or hollow puncture forming member discussed herein includes one or more coatings on the inner surfaces there through to affect conveyance of the electromagnetic radiation and/or fluid as desired.

In another aspect, the application provides a system for conveying one or more frequencies of electromagnetic radiation, the system including one or more sources of electromagnetic radiation and one or more sources of one or more fluids, each of which is in communication with a hollow puncture forming member operationally configured for subcutaneous injection into a target subject. In another embodiment, the system may include one or more therapeutic agents. In another embodiment, the system may include one or more photo-active drugs.

In another aspect, the application provides a device, assembly, system and method for conveying electromagnetic radiation from one or more waveguides through one or more optical interfaces and a hollow puncture forming member to a subcutaneous location within an animal.

In another aspect, the application provides a device, assembly, system and method for substantially transforming electromagnetic radiation.

In another aspect, the application provides a device, assembly, system and method for substantially narrowing electromagnetic radiation.

In another aspect, the application provides a device, assembly, system and method for substantially collimating electromagnetic radiation.

In another aspect, the application provides a device, assembly, system and method for substantially transforming electromagnetic radiation for intravenous and/or intra-arterial use.

In another aspect, the application provides a device, assembly, system and method for substantially collimating electromagnetic radiation for intravenous and/or intra-arterial use.

In another aspect, the application provides a device, assembly, system and method for substantially transforming beams of light for intravenous use and/or intra-arterial.

In another aspect, the application provides a device, assembly, system and method for substantially collimating beams of light for intravenous use and/or intra-arterial.

In another aspect, the application provides a device, assembly, system and method for transmitting collimated electromagnetic radiation through one or more hollow puncture forming members. In another aspect, the application provides a device, assembly, system and method for transmitting collimated electromagnetic radiation and fluid through one or more hollow puncture forming members.

In another aspect, the application provides a device, assembly, system and method for transmitting transformed light through one or more hollow puncture forming members. In another aspect, the application provides a device, assembly, system and method for transmitting transformed light and fluid through one or more hollow puncture forming members.

In another aspect, the application provides a device, assembly, system and method for transmitting collimated light through one or more hollow members or hollow puncture forming members. In another aspect, the application provides a device, assembly, system and method for transmitting collimated light and fluid through one or more hollow members or hollow puncture forming members.

In another aspect, the application provides a device, assembly, system and method for transmitting collimated electromagnetic radiation through one or more hollow members or hollow puncture forming members into a blood vessel of a target subject.

In another aspect, the application provides a device, assembly, system and method for emanating a target subject with collimated electromagnetic radiation.

In another aspect, the application provides a device, assembly, system and method for guiding, transferring or otherwise conveying collimated light through one or more hollow puncture forming members into a blood vessel of a target subject.

In another aspect, the application provides a collimator for transmitting electromagnetic radiation through one or more hollow puncture forming members in communication therewith. In another aspect, the application provides a collimator for transmitting electromagnetic radiation through a liquid light guide in communication therewith.

In another aspect, the application provides a collimator for transmitting electromagnetic radiation through one or more hollow puncture forming members into a blood vessel of a subject. In another aspect, the application provides a collimator for transmitting electromagnetic radiation through a liquid light guide in communication with the collimator into a blood vessel of a subject.

In another aspect, the application provides a system and method for transmitting electromagnetic radiation to one or more subcutaneous sites of a target animal subject. The system and method include a waveguide for conveying radiant energy from a source of radiant energy to a device or assembly in communication with a hollow member, including but not necessarily limited to a hollow puncture forming member. The device or assembly is operationally configured to isolate or otherwise fluidly seal the waveguide from the hollow member and any fluid delivered to the device or assembly as well as any bodily fluid or tissue of a subject. Thus, it is contemplated that a waveguide, e.g., an optical fiber, free from contamination may be reused as desired.

In another aspect, the application provides a device, assembly, system and method for targeting a subject with transformed electromagnetic radiation. In another aspect, the application provides a device, assembly, system and method for targeting a subject with collimated electromagnetic radiation. In one implementation, the device or assembly is operationally configured to receive electromagnetic radiation and fluid therein and convey the electromagnetic radiation and fluid out from the device or assembly. In another implementation, the device or assembly is operationally configured to receive electromagnetic radiation and fluid therein and convey the electromagnetic radiation and fluid out from the device or assembly through a common outlet. In one particular embodiment, the device or assembly includes a transparent fluid barrier. In another particular embodiment, the device or assembly includes a transparent fluid barrier disposed between a waveguide in radiant communication with the device or assembly and a hollow member in radiant and fluid communication with device or assembly.

In another aspect, the application provides an optical device or assembly operationally configured to transmit transformed electromagnetic radiation there through, the transformed electromagnetic radiation being deliverable to one or more target sites external the device.

In another aspect, the application provides an optical device or assembly operationally configured to transmit transformed electromagnetic radiation through one or more hollow puncture forming members attached thereto.

In another aspect, the application provides a device including a lens, the device being operationally configured to transmit transformed electromagnetic radiation through one or more hollow puncture forming members attached thereto. In another aspect, the application provides a device including a lens, the device being operationally configured to transmit collimated electromagnetic radiation through one or more hollow puncture forming members attached thereto.

In another aspect, the application provides a device or assembly for receiving (1) one or more electromagnetic radiation waveguides at a first end and (2) a hollow puncture forming member at a second end; the device being operationally configured to convey electromagnetic radiation received from the one or more waveguides out through the hollow puncture forming member. In another aspect, the application provides a device or assembly for receiving (1) one or more electromagnetic radiation waveguides at a first inlet, (2) a fluid stream at a second inlet and (3) a hollow puncture forming member at a first outlet, the device being operationally configured to convey electromagnetic radiation received from the one or more waveguides and fluid out through the hollow puncture forming member—the fluid acting as an electromagnetic waveguide for the electromagnetic radiation propagating through the hollow puncture forming member.

In another aspect, the application provides a device or assembly operationally configured to receive one or more electromagnetic radiation waveguides at a first end, the device or assembly being operationally configured to convey electromagnetic radiation received from the one or more waveguides out through an aperture of the device. In another aspect, the application provides a device or assembly operationally configured to receive one or more electromagnetic radiation waveguides at a first inlet and fluid at a second inlet, the device or assembly being operationally configured to convey electromagnetic radiation received from the one or more waveguides and fluid out through an aperture of the device or assembly.

In another aspect, the application provides a device or assembly for receiving (1) one or more electromagnetic radiation waveguides at a first end and (2) a hollow puncture forming member at a second end; the device or assembly being operationally configured to narrow electromagnetic radiation received from the waveguides and convey the same out through the hollow puncture forming member.

In another aspect, the application provides a device or assembly for receiving (1) one or more electromagnetic radiation waveguides at a first end and (2) a hollow puncture forming member at a second end; the device or assembly being operationally configured to collimate electromagnetic radiation received from the waveguides and convey the same out through the hollow puncture forming member.

In another aspect, the application provides a device or assembly releasably attachable to an optical waveguide at a first end and a hollow puncture forming member at a second end, wherein the device or assembly is constructed from one or more materials operationally configured to transform, e.g., collimate, electromagnetic radiation received from the optical waveguide, the transformed electromagnetic radiation being conveyed out through the hollow puncture forming member.

In another aspect, the application provides a device or assembly releasably attachable to an optical fiber at a first end and releasably attachable to a hypodermic needle at a second end, wherein the device or assembly is constructed from one or more materials operationally configured to collimate electromagnetic radiation received from the optical fiber and convey the collimated electromagnetic radiation out through the needle; wherein the optical fiber is set apart from or otherwise isolated from the needle.

In another aspect, the application provides a device or assembly releasably attachable to an optical fiber at a first inlet, releasably attachable to a fluid conduit at a second inlet and releasably attachable to a hypodermic needle at a first outlet. The device or assembly operationally configured to transform electromagnetic radiation received from the optical fiber by employing transformation optics, the transformed electromagnetic radiation being conveyed out of the needle; wherein the optical fiber is set apart from or otherwise isolated from the needle, at least in part, via the transformation optics.

In another aspect, the application provides a system and method for transmitting electromagnetic radiation to an intravenous or intra-arterial site, the system including one or more saline solution sources, one or more electromagnetic radiation sources, one or more waveguides in communication with the electromagnetic radiation sources, a collimator and a hollow member or hollow puncture forming member in optical communication with the collimator; wherein the collimator is operationally configured to apply a transform to the electromagnetic radiation received from the one or more waveguides, the transformed electromagnetic radiation being conveyable out through the hollow puncture forming member attached thereto.

In another aspect, the application provides a disposable device for conveying or otherwise directing electromagnetic radiation to a target site including, but not necessarily limited to a subsurface site, subcutaneous site, and combinations thereof.

In another aspect, the application provides a reusable device for conveying or otherwise directing electromagnetic radiation to a target site including, but not necessarily limited to a subsurface site, subcutaneous site, and combinations thereof.

In another aspect, the application provides a system for transmitting electromagnetic radiation to a target site such as a topical, subsurface or subcutaneous site, including communicating to an operator of the system the frequency of the electromagnetic radiation being conveyed to the site.

In another aspect, the application provides an assembly for transmitting electromagnetic radiation to a subcutaneous site including a hollow puncture forming member having a reflective inner surface.

In another aspect, the application provides a system including an assembly operationally configured to simultaneously convey electromagnetic radiation and one or more parenteral substances to a subcutaneous site.

In another aspect, the application provides a device for receiving (1) one or more optical fibers at a first end, and (2) a hypodermic needle at a second end; the device being operationally configured to collimate the electromagnetic radiation received from the one or more optical fibers and direct the collimated electromagnetic radiation out through the hypodermic needle.

In another aspect, the application provides a device, assembly, system and method for targeting and/or treating one or more blood contaminants of a subject with electromagnetic radiation.

In another aspect, the application provides a device, assembly, system and method for targeting and/or treating one or more blood disorders of a subject with electromagnetic radiation.

In another aspect, the application provides a device, assembly, system and method for targeting and/or treating one or more blood diseases of a subject with electromagnetic radiation.

In another aspect, the application provides a device, assembly, system and method for targeting and/or treating one or more blood infections of a subject with electromagnetic radiation.

In another aspect, the application provides a device, assembly, system and method for targeting and/or treating one or more infectious diseases of a subject with electromagnetic radiation. In another aspect, the application provides a device, assembly, system and method for targeting and/or treating one or more infectious diseases of a subject with transformed electromagnetic radiation.

In another aspect, the application provides a device, assembly, system and method for targeting and/or treating one or more emerging infectious diseases of a subject with electromagnetic radiation. In another aspect, the application provides a device, assembly, system and method for targeting and/or treating one or more emerging infectious diseases of a subject with transformed electromagnetic radiation.

In another aspect, the application provides a device, assembly, system and method for treating and/or treating one or more blood cancers of a subject with electromagnetic radiation.

In another aspect, the application provides a device, assembly, system and method for targeting and/or treating one or more blood-borne pathogens of a subject with electromagnetic radiation.

In another aspect, the application provides a device, assembly, system and method for targeting and/or treating malaria with electromagnetic radiation.

In another aspect, the application provides a device, assembly, system and method for targeting and/or treating syphilis with electromagnetic radiation.

In another aspect, the application provides a device, assembly, system and method for targeting and/or treating brucellosis with electromagnetic radiation.

In another aspect, the application provides a device, assembly, system and method for targeting and/or treating Hepatitis A with electromagnetic radiation.

In another aspect, the application provides a device, assembly, system and method for targeting and/or treating Hepatitis B with electromagnetic radiation.

In another aspect, the application provides a device, assembly, system and method for targeting and/or treating Hepatitis C with electromagnetic radiation.

In another aspect, the application provides a device, assembly, system and method for targeting and/or treating Hepatitis D with electromagnetic radiation.

In another aspect, the application provides a device, assembly, system and method for targeting and/or treating Hepatitis E with electromagnetic radiation.

In another aspect, the application provides a device, assembly, system and method for targeting and/or treating Hepatitis X with electromagnetic radiation.

In another aspect, the application provides a device, assembly, system and method for targeting and/or treating Hepatitis G with electromagnetic radiation.

In another aspect, the application provides a device, assembly, system and method for targeting Human Immunodeficiency Virus ("HIV") with electromagnetic radiation. As understood by skilled artisans, HIV may include a retrovirus or group of retroviruses denominated "HIV", "HIV-1," "HIV-2," "HIV-3" and "HIV-4." The most common cause of AIDS is thought to be HTLV-III, typically referred to as HIV-1.

In another aspect, the application provides a device, assembly, system and method for targeting and/or treating one or more RNA viruses (as the term is understood by the skilled artisan) with electromagnetic radiation.

In another aspect, the application provides a device, assembly, system and method for targeting and/or treating viral hemorrhagic fever with electromagnetic radiation.

In another aspect, the application provides a device, assembly, system and method for targeting and/or treating ebola virus disease ("EVD") with electromagnetic radiation.

In another aspect, the application provides a device, assembly, system and method for targeting and/or treating one or more blood contaminants, one or more blood disorders, one or more blood diseases, one or more blood infections, one or more infectious diseases, one or more emerging infectious diseases, one or more blood cancers, one or more pathogens, one or more blood products, one or more blood contaminants with electromagnetic radiation and intravenous therapy.

In another aspect, the application provides a system and method for adjusting or otherwise altering the electromagnetic radiation and/or the duration of treatment of one or more blood contaminants, one or more blood disorders, one or more blood diseases, one or more blood infections, one or more infectious diseases, one or more emerging infectious diseases, one or more blood cancers, one or more pathogens, one or more blood products, one or more blood contaminants with electromagnetic radiation.

In another aspect, the application provides an apparatus operationally configured to generate selected wavelengths of electromagnetic radiation at a selected power level for a specified duration of time, the electromagnetic radiation being conveyable to one or more surface and/or subsurface target sites of a subject.

In another aspect, the application provides a system and method operationally configured to generate selectable wavelengths of light at a selected power level for a specified duration of time, the light being conveyable to one or more surface and/or subsurface target sites of a subject via the system.

In another aspect, the application provides a system and method operationally configured to generate and deliver selectable wavelengths of electromagnetic radiation at user selectable power levels to one or more surface and/or subsurface target sites of a subject.

In another aspect, the application provides a system and method operationally configured to generate and deliver selectable wavelengths of light at user selectable power levels to one or more surface and/or subsurface target sites of a subject.

In another aspect, the application provides a system and method operationally configured to generate selectable wavelengths of electromagnetic radiation at user selectable power levels, the system including a puncture forming device operationally configured to convey the electromagnetic radiation to a surface and/or subsurface target site of a subject.

In another aspect, the application provides a device or assembly for receiving (1) one or more electromagnetic radiation waveguides at a first end and (2) a hollow puncture forming member at a second end; the device or assembly being operationally configured to transform electromagnetic radiation received from the one or more waveguides and convey the same out through the hollow puncture forming member, the device or assembly being operationally configured to isolate the one or more electromagnetic radiation waveguides apart from the hollow puncture forming member.

In another aspect, the application provides a device or assembly for receiving (1) one or more electromagnetic radiation waveguides at a first end and (2) a hollow puncture forming member at a second end; the device or assembly being operationally configured to transform electromagnetic radiation received from the one or more waveguides and convey the electromagnetic radiation out through the hollow puncture forming member, the device or assembly being operationally configured to isolate the one or more electromagnetic radiation waveguides apart from an open tip of the hollow puncture forming member.

In another aspect, the application provides a device or assembly for receiving (1) one or more electromagnetic radiation waveguides at a first end and (2) a hollow puncture forming member at a second end; the device or assembly being operationally configured to collimate electromagnetic radiation received from the one or more waveguides and convey the electromagnetic radiation out through the hollow puncture forming member, the device or assembly being operationally configured to isolate the one or more electromagnetic radiation waveguides apart from an open tip of the hollow puncture forming member.

In another aspect, the application provides a device or assembly for receiving (1) one or more optical fibers at a first location, (2) one or more fluids at one or more second locations and (3) a needle at a third location; the device or assembly being operationally configured to collimate electromagnetic radiation received from the one or more optical fibers and convey the collimated electromagnetic radiation and fluid out through the needle, the device or assembly being operationally configured to isolate the one or more optical fibers apart from the needle and fluid within the device or assembly.

In another aspect, the application provides a device or assembly for receiving (1) one or more optical fibers at a first location, (2) one or more fluids at one or more second locations and (3) a hypodermic needle at a third location; the device or assembly being operationally configured to collimate electromagnetic radiation received from the one or more optical fibers and convey the collimated electromagnetic radiation and fluid out through the needle, the device or assembly being operationally configured to isolate the one or more optical fibers apart from an open tip of the needle and fluid within the device or assembly.

In another aspect, the application provides a system operationally configured to guide or otherwise convey electromagnetic radiation from one or more sources of electromagnetic radiation to one or more target sites, the system including one or more sources of electromagnetic radiation, one or more optical interfaces in communication with the one or more sources of electromagnetic radiation, and one or more delivery devices in communication with the one or more optical interfaces for conveying electromagnetic radiation to one or more target sites. The system may further include one or more fluid sources. The system may be operationally configured to convey fluid and electromagnetic radiation out of a common outlet of the device. For example, the system may be operationally configured to convey fluid and electromagnetic radiation out from the device to one or more target sites.

In another aspect, the application provides a system operationally configured to guide or otherwise convey electromagnetic radiation to one or more target sites, the system including at least one or more sources of electromagnetic radiation, one or more waveguides in communication with the one or more sources of electromagnetic radiation, one or more optical interfaces in communication with the one or more waveguides, and one or more delivery devices in communication with the one or more optical interfaces for conveying electromagnetic radiation to one or more target sites. The system may further include one or more fluid sources. The system may be operationally configured to convey fluid and electromagnetic radiation out from the device.

In another aspect, the application provides a system operationally configured to guide or otherwise convey electromagnetic radiation to one or more target sites, the system including at least one or more sources of electromagnetic radiation, one or more waveguides in communication with the one or more sources of electromagnetic radiation, the one or more waveguides being provided with one or more optical interfaces, and one or more delivery devices in communication with the one or more waveguides for conveying electromagnetic radiation to one or more target sites. The system may further include one or more fluid sources. The system may be operationally configured to convey fluid and electromagnetic radiation out from the device. The system may be operationally configured to convey fluid and electromagnetic radiation out from the device to one or more target sites.

In another aspect, the application provides a system operationally configured to guide or otherwise convey electromagnetic radiation to one or more target sites, the system including at least one or more sources of electromagnetic radiation, one or more waveguides in communication with the one or more sources of electromagnetic radiation, and one or more delivery devices provided with optical interfaces, whereby the delivery devices are in communication with the one or more waveguides and operationally configured to convey electromagnetic radiation to one or more target sites. The system may further include one or more fluid sources. The system may be operationally configured to convey fluid and electromagnetic radiation out from the device. The system may be operationally configured to convey fluid and electromagnetic radiation out from the device to one or more target sites.

In another embodiment, the application provides a device or assembly having one or more sources of electromagnetic radiation, one or more optical interfaces, and one or more outlets for conveyance of electromagnetic radiation to one or more target sites.

In another embodiment, the application provides a device or assembly having one or more sources of electromagnetic radiation, one or more sources of fluid, one or more optical interfaces, and one or more outlets for conveyance of electromagnetic radiation and fluid. The device may include a self contained power source for powering the one or more sources of electromagnetic radiation. Or, in the alternative, the one or more sources of electromagnetic radiation may be powered via an external source.

In another embodiment, the application provides a device or assembly including a hollow puncture forming member comprised of one or more non-absorbent materials.

In another embodiment, the application provides a device or assembly including a hollow puncture forming member including an inner surface comprised of one or more non-absorbent materials.

In another embodiment, the application provides a device or assembly including a metal hollow puncture forming member including an inner surface comprised one or more non-absorbent materials.

In another embodiment, the application provides a device or assembly including a plastic hollow puncture forming member comprised of one or more non-absorbent materials.

In another embodiment, the application provides a device or assembly including a plastic puncture forming member including an inner surface comprised of one or more non-absorbent materials.

In another embodiment, the application provides a device or assembly including a hollow puncture forming member constructed from one or more composite materials, the hollow puncture forming member including an inner surface comprised of one or more non-absorbent materials.

In another embodiment, the application provides a device or assembly including a hollow puncture forming member constructed from silicone, the hollow puncture forming member including an inner surface comprised of one or more non-absorbent materials.

In another embodiment, the application provides a device or assembly including a cannulation technique for intravenous and/or intra-arterial conveyance of electromagnetic radiation.

In another embodiment, the application provides a device or assembly including a hollow member or a hollow puncture forming member defined by an inner surface of total internal reflection. In another embodiment, the application provides a device or assembly having an outlet for electromagnetic radiation and/or fluid defined by an inner surface of total internal reflection.

In another embodiment, the application provides a hollow puncture forming member substantially bonded to an inner optical fiber.

In another embodiment, the application provides a device, assembly, system, and method for irradiation of blood using electromagnetic radiation. The blood may belong to a single person or animal or multiple persons or animals when treating blood housed in one or more containers.

In another embodiment, the application provides a device, assembly, system, and method for radiant energy blood irradiation in vivo and/or in vitro.

In another embodiment, the application provides a device, assembly, system, and method for extracorporeal targeting of animal fluid using electromagnetic radiation. In another embodiment, the application provides a device, assembly, system, and method for extracorporeal targeting and intravenous and/or intra-arterial targeting of animal fluid using electromagnetic radiation.

In another embodiment, the application provides a device, assembly, system, and method incorporating an extracorporeal circuit and an injectable waveguide operationally configured to emit electromagnetic radiation there from. In one aspect, the extracorporeal circuit and injectable waveguide are operationally configured to target animal fluid using electromagnetic radiation. In one embodiment, the injectable waveguide is suitable effective as a liquid light guide in operation.

In another aspect, the application provides a device or assembly for transmitting electromagnetic radiation out there from to a surface location and/or a subsurface location including, but not necessarily limited to a subcutaneous site, the device or assembly including a hollow puncture forming member having a reflective inner surface. In one embodiment, the hollow puncture forming member may be formed from one or more materials operationally configured to be shaped into a desired form. In another embodiment, the hollow puncture forming member may be formed from one or more resins and/or one or more polyresins operationally configured to be shaped into a desired form.

In another aspect, the application provides a device or assembly for transmitting electromagnetic radiation to a surface location and/or a subsurface location of a target subject including, but not necessarily limited to a subcutaneous site, the device including a hollow puncture forming member joined to an optical fiber housed therein.

In another aspect, the application provides a device, assembly, system and method of photoluminescence, as the term is understood by the skilled artisan. The system may include a source of electromagnetic radiation whereby the radiation output of the source may be adjusted according to one or more parameters including, but not necessarily limited to the electromagnetic spectrum of a target subject. The system is operationally configured to convey electromagnetic radiation from the source to a device or assembly for conveying the electromagnetic radiation to one or more target sites of the subject.

In another aspect, the application provides a device, assembly, system and method of hemo-irradiation, as the term is understood by the skilled artisan.

In another aspect, the application provides a device, assembly, system and method of photopheresis, as the term is understood by the skilled artisan.

In another aspect, the application provides a device, assembly, system and method of photochemotherapy, as the term is understood by the skilled artisan.

In another aspect, the application provides a device, assembly, system and method of photobiological therapy, as the phrase is understood by the skilled artisan.

In another aspect, the application provides a device, assembly, system and method of photo-oxidation, as the term is understood by the skilled artisan.

In another aspect, the application provides a device, assembly, system and method of ultraviolet blood irradiation, as the phrase is understood by the skilled artisan.

In another aspect, the application provides a device, assembly, system and method of photodynamic therapy, as the phrase is understood by the skilled artisan.

In another aspect, the application provides a method of exposing animal blood to electromagnetic radiation.

In another aspect, the application provides a device, assembly, system and method for guiding, transmitting or otherwise conveying electromagnetic radiation to one or more target sites of a subject in a manner effective to inactivate blood contaminants of the subject.

In another aspect, the application provides a device, assembly, system and method for guiding, transmitting or otherwise conveying electromagnetic radiation to one or more target sites of a subject in a manner effective to inactivate toxins and viruses of the subject.

In another aspect, the application provides a device, assembly, system and method for guiding, transmitting or otherwise conveying electromagnetic radiation to one or more target sites of a subject in a manner effective to destroy and/or inhibit viruses of the subject.

In another aspect, the application provides a device, system and method for guiding, transmitting or otherwise conveying electromagnetic radiation to one or more target sites of a subject in a manner effective to destroy and/or inhibit the growth of bacteria of the subject.

In another aspect, the application provides a device, assembly, system and method for guiding, transmitting or otherwise conveying electromagnetic radiation to one or more target sites of a subject in a manner effective to kill pathogens in the bloodstream of the subject, the duration of exposure of the blood to electromagnetic radiation being less than the duration required to kill the same pathogens outside of the subject, e.g., the targeting of pathogens in a laboratory setting.

In another aspect, the application provides a device, assembly, system and method for guiding, transmitting or otherwise conveying electromagnetic radiation to one or more target sites of a subject in a manner effective to destroy and/or inhibit the growth of fungi of the subject.

In another aspect, the application provides a device, assembly, system and method for guiding, transmitting or otherwise conveying electromagnetic radiation to one or more target sites of an animal subject in a manner effective to increase the oxygen-combining power of the blood of the subject.

In another aspect, the application provides a device, assembly, system and method for guiding, transmitting or otherwise conveying electromagnetic radiation to one or more target sites of an animal subject in a manner effective to activate steroid hormones of the subject.

In another aspect, the application provides a device, assembly, system and method for guiding, transmitting or otherwise conveying electromagnetic radiation to one or more target sites of an animal subject in a manner effective to increase cell permeability of the subject.

In another aspect, the application provides a device, assembly, system and method for guiding, transmitting or otherwise conveying electromagnetic radiation to one or more target sites of an animal subject in a manner effective for the blood of the subject to continue emanating secondary radiation following treatment.

In another aspect, the application provides a device, assembly, system and method for guiding, transmitting or otherwise conveying electromagnetic radiation to one or more target sites of an animal subject in a manner effective to cause vasodilation.

In another aspect, the application provides a device, assembly, system and method for guiding, transmitting or otherwise conveying electromagnetic radiation to one or more target sites of an animal subject in a manner effective to activate white blood cells of the subject.

In another aspect, the application provides a device, system and method for guiding, transmitting or otherwise conveying electromagnetic radiation to one or more target sites of an animal subject in a manner effective to decrease platelet aggregation of the subject.

In another aspect, the application provides a device, assembly, system and method for guiding, transmitting or otherwise conveying electromagnetic radiation to one or more target sites of an animal subject in a manner effective to stimulate fibrinolysis of the subject.

In another aspect, the application provides a device, assembly, system and method for guiding, transmitting or otherwise conveying electromagnetic radiation to one or more target sites of an animal subject in a manner effective to decrease the viscosity of blood of the subject.

In another aspect, the application provides a device, assembly, system and method for guiding, transmitting or otherwise conveying electromagnetic radiation to one or more target sites of an animal subject in a manner effective to stimulate corticosteroid production of the subject.

In another aspect, the application provides a device, assembly, system and method for guiding, transmitting or otherwise conveying electromagnetic radiation to one or more target sites of an animal subject in a manner effective to improve or increase microcirculation of the subject.

In another aspect, the application provides a device, assembly, system and method for guiding, transmitting or otherwise conveying electromagnetic radiation to one or more target sites of an animal subject whereby multiple treatments of a subject has cumulative physiological and/or therapeutic effects.

In another aspect, the application provides a device, assembly, system and method for guiding, transmitting or otherwise conveying electromagnetic radiation to one or more target sites of an animal subject in a manner effective to restore normal chemical balances of the subject.

In another aspect, the application provides a device, assembly, system and method for guiding, transmitting or otherwise conveying electromagnetic radiation to one or more target sites of an animal subject in a manner effective to enhance local and systemic resistance of the subject.

In another aspect, the application provides a device, assembly, system and method for guiding, transmitting or otherwise conveying electromagnetic radiation to one or more target sites of an animal subject in a manner effective to damage the DNA inside target cells making the cells unable to divide and reproduce.

In another aspect, the application provides a device, assembly, system and method for guiding, transmitting or otherwise conveying electromagnetic radiation to the blood of an animal subject in a manner effective to cause the hemoglobin to absorb the electromagnetic radiation.

In another aspect, the application provides a device, assembly, system and method for guiding, transmitting or otherwise conveying electromagnetic radiation to the blood of an animal subject in a manner effective to produce an autogeneous vaccine.

In another aspect, the application provides a device, assembly, system and method for guiding, transmitting or otherwise conveying electromagnetic radiation to capillaries of one or more target subjects.

In another aspect, the application provides a device, assembly, system and method for guiding, transmitting or otherwise conveying electromagnetic radiation to the blood of an animal subject in a manner effective to increase vitamin D content and/or cholesterol in the blood plasma of the subject.

In another aspect, the application provides a device, assembly, system and method for guiding, transmitting or otherwise conveying electromagnetic radiation to the blood of an animal subject in a manner effective to increase oxygen absorption by the blood of the subject.

In another aspect, the application provides a device, assembly, system and method for guiding, transmitting or otherwise conveying electromagnetic radiation to the blood of an animal subject for treating ultraviolet-light deficiency as understood by the skilled artisan.

In another aspect, the application provides a device, assembly, system and method for guiding, transmitting or otherwise conveying electromagnetic radiation to the blood of an animal subject for producing one or more photochemical reactions.

In another aspect, the application provides an electromagnetic radiation source, a radiation conduit, a source of one or more therapeutic agents and a device in communication with the radiation source and the therapeutic agent source that is operationally configured to direct electromagnetic radiation and one or more therapeutic agents to a target site such as a subcutaneous site of an animal. In this embodiment, one or more of (1) the intensity of the electromagnetic radiation, (2) the wavelength of the spectral energy used and (3) the duration of exposure may be determined according to (a) the absorption characteristics of the one or more blood contaminants targeted for exposure to the electromagnetic radiation, (b) as necessary to produce a desired photo-chemical change in the animal.

In another aspect, the application provides a device, assembly, system and method for treating and/or filtering and/or purifying one or more fluids to be conveyed from a source to a target site. Thus, in one aspect, the device, assembly and system may be operationally configured to treat one or more fluids via mechanical treatment and/or radiant energy targeting.

In another aspect, the application provides a device, assembly, system and method for treating and/or adding one or more components to fluid being conveyed to a target site.

In another aspect, the application provides a device, assembly, system and method for guiding, transmitting or otherwise conveying electromagnetic radiation to one or more target sites making use of radio-frequency identification ("RFID") technology (often referred to as RFID tags) to ensure that only approved component parts may be used as part of the system. In other words, if the correct data is not transmitted according to the required RFID, then one or more component parts including the source of electromagnetic radiation, waveguide, device or assembly may not be operable. Such identification measures may support anti-counterfeiting, provide tamper proofing of the device, assemblies and system herein, protect against the manufacturing and sale of unendorsed copycat component parts, electronics or other items. Likewise, it also contemplated that one or more system components may be given a unique serial number. An electromagnetic radiation source may be calibrated according to the hollow puncture forming member identified for use in one or more particular treatments. Thus, an antenna may be used near an optical fiber whip operationally configured to read a tag encrypted code as desired. In other embodiments, image based technology may be employed as understood by the skilled artisan. In one embodiment, QR Code technology may be employed as desired.

In another aspect, the application provides a device, assembly, system and method operationally configured to convey fluid and electromagnetic radiation to one or more target sites. In particular, a source of electromagnetic radiation may be operationally configured to produce electromagnetic radiation of a particular wavelength and amplitude. In one aspect, the wavelength and amplitude of the electromagnetic radiation may be substantially maintained throughout the system. In another aspect, the wavelength and amplitude of the electromagnetic radiation may be altered via one or more mechanical means. In another aspect, a wavelength and amplitude of radiant energy generated by the source of electromagnetic radiation at any given moment may be determined or otherwise calculated in a manner effective to emit a particular wavelength and amplitude of radiant energy to a target site according to one or more variables or parameters including, but not necessarily limited to the index of refraction and/or total internal reflection and/or numerical aperture and/or various absorption properties and/or scattering properties of any waveguides, optical interfaces and hollow puncture forming members employed, the compression of radiant energy during the transition from one waveguide into another waveguide of smaller cross section, the index of refraction and/or absorption properties and/or scattering properties of fluids used, and combinations thereof.

In another aspect, the application provides a system including a radiant energy source programmable as desired, a waveguide in radiant communication with the source, a transformation hub for receiving the waveguide in communication therewith and for transforming radiant energy received via the waveguide, a fluid housing in radiant communication with the transformation hub and in fluid communication with one or more fluid sources, and a hollow puncture forming member in radiant communication and fluid communication with the fluid housing.

In another aspect, the application provides for the transformation of electromagnetic waves via transformation optics at a point between a source of electromagnetic radiation and a target of the electromagnetic radiation. The application suitably provides transformation optics set apart from a hollow puncture forming member operationally configured to deliver electromagnetic radiation to a target.

In another aspect, the application provides a device or assembly comprising transformation optics for transforming electromagnetic radiation in a manner best suited for conveyance of the electromagnetic radiation through a hollow member in radiant communication with the device or assembly. It is also contemplated that the transformation may comprise attenuation of undesirable frequencies of electromagnetic radiation or conversion of at least part of emitted electromagnetic radiation to a more desirable form.

In another aspect, the application provides a device or assembly comprising transformation optics for transforming electromagnetic radiation received by the device or assembly. The device or assembly is operationally configured to receive a hollow member in attachment thereto. In one embodiment, the center of the transformation optics is substantially aligned with the longitudinal axis of the hollow member. In another embodiment, varying transformation optics are interchangeable with the device or assembly as desired.

In one aspect, the application provides for photodynamic therapy by employing a waveguide assembly for injecting electromagnetic radiation and/or one or more fluids into a target subject. In one exemplary embodiment, the application provides a method including injecting photosensitizers that concentrate in diseased cells of a target animal.

In another aspect, the application provides devices, assemblies and systems including one or more anti-counterfeiting technologies including, not necessarily limited to plastic identifiers, e.g., particle taggants, optical devices and quantum dots, hologram labeling, radio-frequency identification ("RFID"), RFID crystagrams, integrated circuits, encryption, and combinations thereof—as each is understood by the skilled artisan.

In another aspect, the application provides methods for targeting blood contaminants of animals with electromagnetic radiation of one or more frequencies for one or more durations as desired.

Discussion

The following description is not to be taken in a limiting sense but is made merely for the purpose of describing the general principles of the teachings of the embodiments discussed herein. To better understand the novelty of the teachings of the embodiments, reference is hereafter made to the accompanying drawings. It is to be fully recognized that the different teachings of the embodiments discussed below may be employed separately or in any suitable combination to produce desired results.

As shown in the simplified illustration of FIG. 1, a first simplified system is provided. In this embodiment, the system suitably includes a first electromagnetic radiation source 100, a first waveguide 102 (or "radiant energy conduit"), a first fluid source 104 and a first treatment device 106. In another embodiment, the first electromagnetic radiation source 100 may be understood to include one or more waveguides 102. As shown, the treatment device 106 is in (1) radiant communication with the electromagnetic radiant source 100 via the waveguide 102 and in (2) fluid communication with the fluid source 104 via fluid conduit 107. The radiation source 100 is in radiant communication with the waveguide 102 via outlet 101 and the waveguide 102 is in radiant communication with the treatment device 106 via a proximal attachment 108. In this embodiment, the treatment device 106 is operationally configured to convey electromagnetic radiation and fluid received via waveguide 102 and fluid conduit 107 to a target site including but not necessarily limited to a subcutaneous target site of a subject 10, which in FIG. 1 includes a blood vessel 15.

The system may also include an electromagnetic radiation source 100 operationally configured to communicate with two or more waveguides 102. As such, electromagnetic radiation may be conveyed via two or more waveguides 102 to target sites of one or more subjects.

Figure 2:
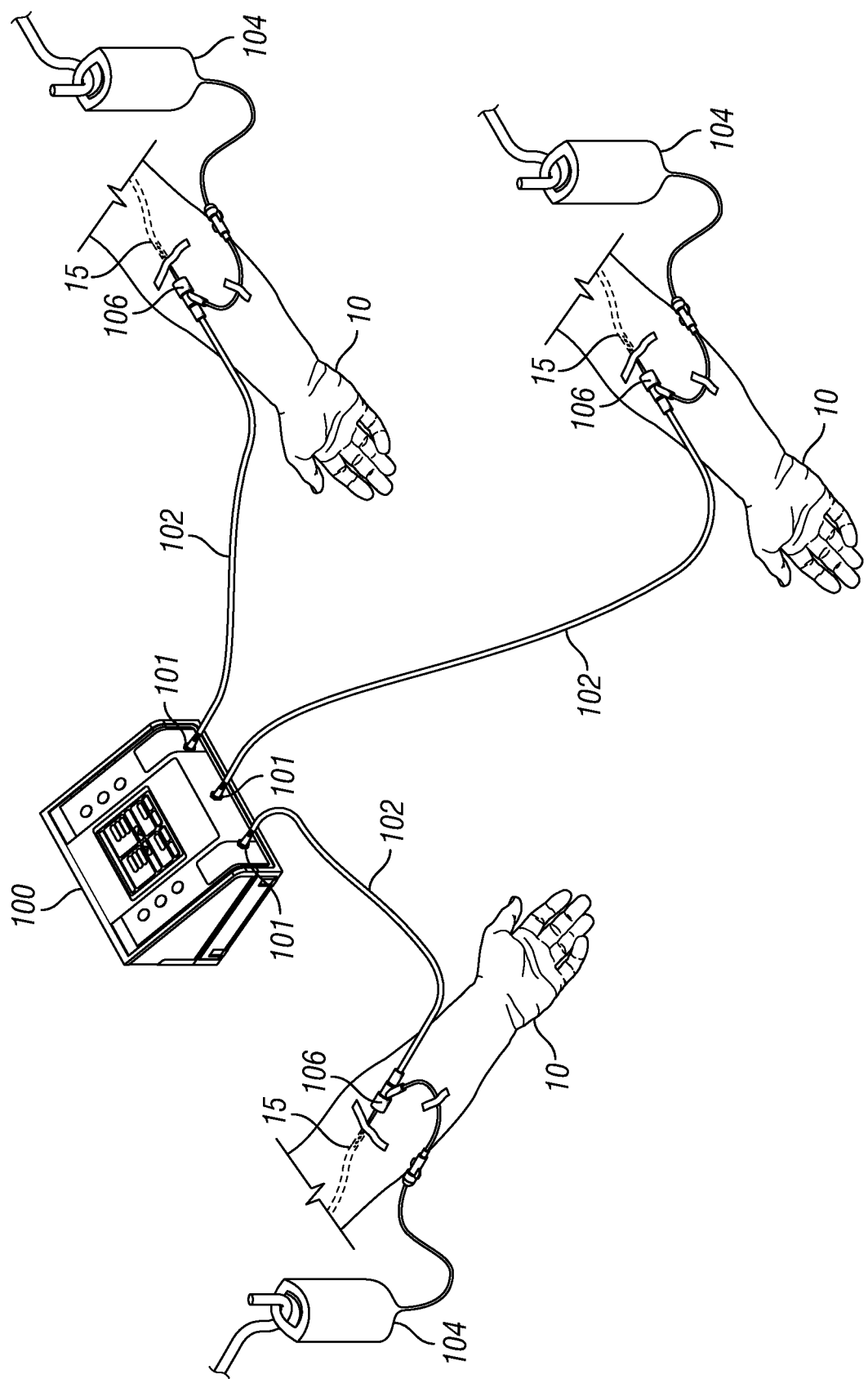
FIG. 2 illustrates another simplified embodiment of a system of this application.

In the particular embodiment of FIG. 2, the electromagnetic radiation source 100 includes three outlets 101 in radiant communication with corresponding waveguides 102 and treatment devices 106 for conveying electromagnetic radiation to blood vessels of three separate target subjects 10. It is also contemplated that multiple outlets 101, waveguides 102 and treatment devices 106 may be used to convey electromagnetic radiation to multiple sites of a single target subject 10, e.g., locating one treatment device 106 within a blood vessel of a target subject's 10 arm and locating another treatment device 106 within a blood vessel of the target subject's 10 leg. When targeting fluid housed in a container or a surface location, multiple treatment devices 106 may target a similar container or site.

Suitably, the treatment device 106 includes at least one port, inlet, or connection member operationally configured to receive or otherwise communicate with the waveguide 102 and at least one port, inlet, or connection member operationally configured to receive or otherwise communicate with the fluid conduit 107. It is contemplated that in one embodiment the treatment device 106 receive only electromagnetic radiation and no fluid, whereby the treatment device 106 is provided with only one or more connection members operationally configured to receive waveguides 102 in communication therewith. In still another embodiment, the treatment device 106 may be provided with one or more multi-purpose connection members operationally configured to receive or otherwise communicate with either a waveguide 102 or a fluid conduit 107.

In one embodiment, the electromagnetic radiation source 100 may be operationally configured to produce electromagnetic radiation across the electromagnetic spectrum. In another embodiment, the electromagnetic radiation source 100 may be operationally configured to produce electromagnetic radiation across a particular range of frequencies or wavelengths. In still another embodiment, the electromagnetic radiation source 100 may be operationally configured to produce electromagnetic radiation at a particular frequency or wavelength. In still another embodiment, the electromagnetic radiation source 100 may be operationally configured to produce electromagnetic radiation across the electromagnetic spectrum at one or more intensities and/or one or more frequencies for a particular duration or durations. Thus, in one embodiment the electromagnetic radiation source 100 may be programmable or otherwise controlled manually to emanate electromagnetic radiation therefrom as desired.

Figure 3:
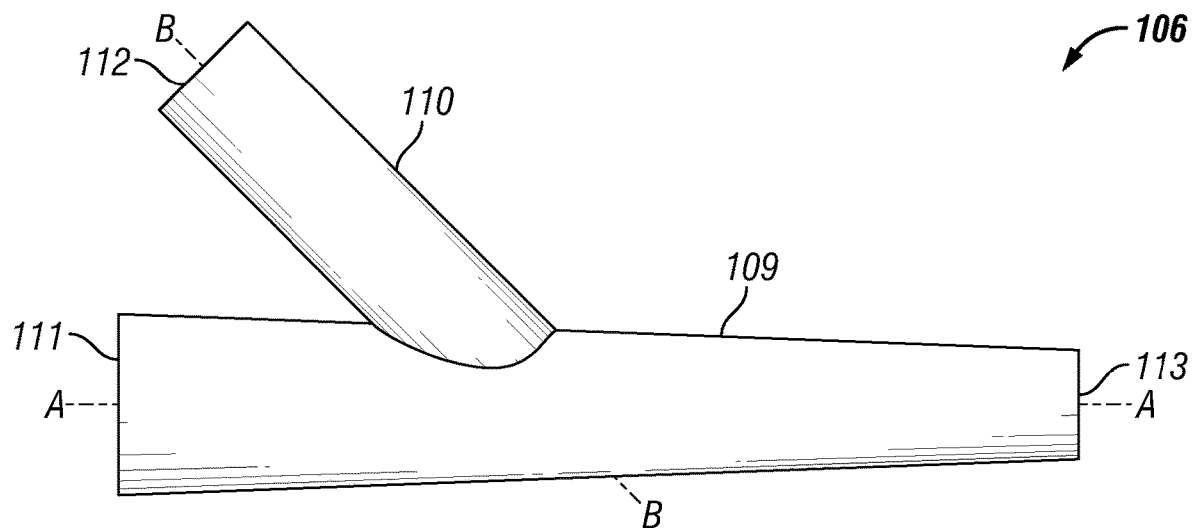
FIG. 3 illustrates a side view of a simplified embodiment of a treatment device.
Figure 4:
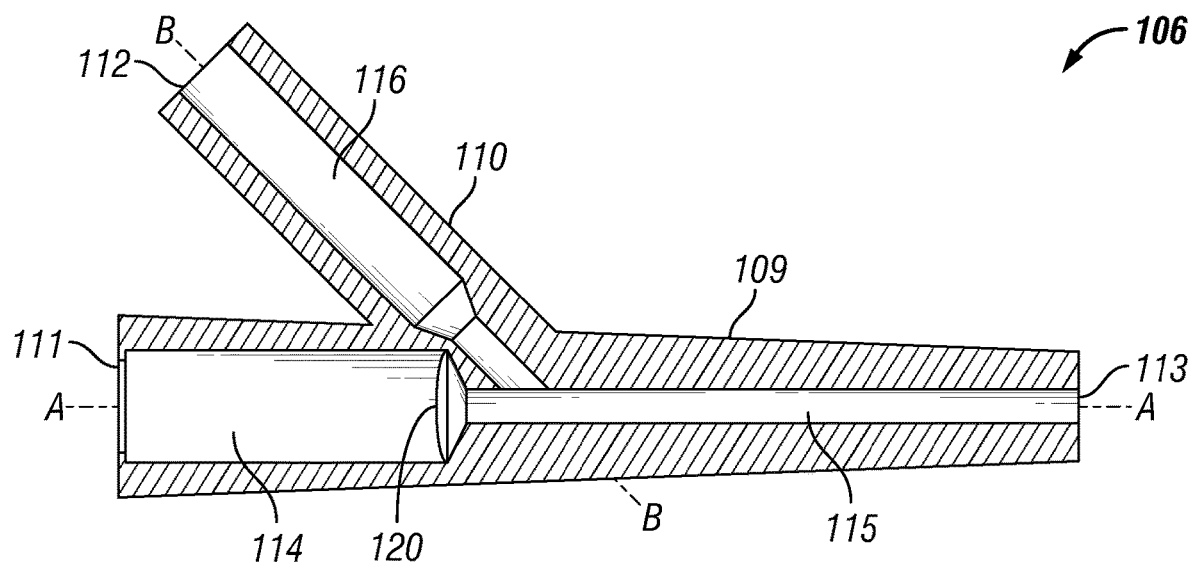
FIG. 4 illustrates a sectional view of the treatment device of FIG. 3.

Turning to FIGS. 3 and 4, a simplified embodiment of a treatment device 106 is provided including a first body 109 and a second body 110 in communication with the first body 109. As shown, the first body 109 has a longitudinal axis A-A and the second body 110 has a longitudinal axis B-B. Non-linear configurations of the bodies 109 and 110 are also herein contemplated for implementation. The outer surfaces of the first and second bodies 109, 110 are not necessarily limited to a particular surface ornamentation, but, it may be desirable to include an outer surface configuration for ease of use by one or more persons handling or using the treatment device 106. Thus, the outer surface of the treatment device 106 may be smooth and/or textured. The outer surface of the treatment device 106 may also include raised surface members or depressed surface areas, e.g., parallel ridges to frictionally engage a person's hand or fingers.

As depicted in FIG. 4, the first body 109 includes (1) a first inlet 111 in communication with a first opening 114 therein and (2) a first outlet 113 in communication with a second opening 115 therein—the first opening 114 being in radiant communication with the second opening 115. The second body 110 includes a second inlet 112 in communication with a third opening 116 therein. The second body 110 is suitably connected to the first body 109 in a manner effective to communicate the third opening 116 with the second opening 115. Thus, the second opening 115 suitably lies in communication with both the first opening 114 and the third opening 116.

More particularly, the first inlet 111 is operationally configured to receive a waveguide 102 in attachment thereto to provide radiant communication between the electromagnetic radiation source 100 and the first body 109. Likewise, the second inlet 112 is operationally configured to receive a fluid conduit 107 in attachment thereto to provide fluid communication between the fluid source 104 and the second body 110. Thus, the first outlet 113 suitably lies (1) in radiant communication with the first inlet 111 and (2) in fluid communication with the second inlet 112 in a manner effective to emit electromagnetic radiation and/or discharge fluid out through the first outlet 113.

In one embodiment, the first and second inlets 111, 112 may be operationally configured to receive a corresponding waveguide 102 and fluid conduit 107 in releasable attachment thereto. In another embodiment, one or more of the inlets 111, 112 may be operationally configured to receive a corresponding waveguide 102 and fluid conduit 107 in permanent attachment thereto. As desired, the one or more of the inlets 111, 112 may be operationally configured to receive a corresponding waveguide 102 and fluid conduit 107 in sealed attachment thereto or in a manner effective to diminish leakage of radiant energy and/or fluid during operation of the treatment device 106 and system. In still another embodiment, the treatment device 106, waveguide 102 and fluid conduit 107 may be provided as a single assembly.

Still referring to FIG. 4, the first opening 114 and the second opening 115 may be linearly aligned along the longitudinal axis A-A of the first body 109. In another embodiment, the first opening 114 and the second opening 115 may be linearly aligned substantially parallel to the longitudinal axis A-A of the first body 109. In still another embodiment, the first opening 114 and the opening 115 may be disposed within the first body 109 in a non-linear configuration effective to guide electromagnetic radiation from the first inlet 111 out through the outlet 113.

Suitably, the first opening 114 and the second opening 115 have an inner surfaces operationally configured to guide electromagnetic radiation there through as desired. Thus, in one aspect, the treatment device 106 functions as a waveguide effective to guide electromagnetic radiation received at the first inlet 111 out through the first outlet 113 as desired. In one embodiment, the treatment device 106 may guide electromagnetic radiation there through unobstructed. In another embodiment, the treatment device 106 may be operationally configured to act on the electromagnetic radiation in one or more modes effective to transform the electromagnetic radiation prior to exiting out through the first outlet 113.

As shown in FIG. 4, the first and second openings 114, 115 may be defined by cylindrical inner surfaces. In another embodiment, the first and second openings 114, 115 may be defined by curved non-cylindrical inner surfaces. In another embodiment, the first and second openings 114, 115 may be defined by multi-sided inner surfaces. It is also contemplated that the first and second openings 114, 115 be provided with non-corresponding inner surfaces, e.g., the first opening 114 having four sides and the second opening 115 having a cylindrical inner surface. In one embodiment, the first and second openings 114, 115 may include substantially similar inner diameters or widths. In another embodiment, first and second openings 114, 115 may include different inner diameters or widths. As shown in FIG. 4, the first opening 114 includes a larger diameter than the second opening 115.

In other embodiments, the size and shape of the first inlet 111 may or may not correspond to the size and shape of the first opening 114 and the size and shape of the first outlet 113 may or may not correspond to the size and shape of the second opening 115. In still another embodiment, the size and shape of the first inlet and/or the first opening 114 may be determined according to the size and shape of a waveguide 102 or intermediary device to be attached to the first inlet 111. Likewise, the size and shape of the first outlet 113 may be determined according to a particular target site of a subject 10, a particular dosage of radiant energy to be applied to a subject 10 and/or the size and shape of a hollow puncture forming member to be attached to the first outlet 113.

Still referring to FIGS. 3 and 4, the treatment device 106 may be operationally configured in a manner whereby the third opening 116 lies in fluid communication with second opening 115 at a point along the length of the first body 109 whereby fluid entering the second opening 115 may flow a particular distance to the outlet 113 as desired. Suitably, the fluid may flow through the treatment device 106 under pressure or via gravity in a manner effective for the fluid to exit out through the first outlet 113 as desired. In one embodiment, fluid may flow out through the first outlet 113 in a constant flow. In another embodiment, the system and/or treatment device 106 alone may be provided in a manner effective to provide intermittent fluid flow out through the first outlet 113.

It is also contemplated that a fluid in the form of a liquid or liquid composition having a known refractive index may be introduced into the treatment device 106 via second inlet 112. In such embodiment, the present system may be operationally configured to produce a particular radiant energy at the radiation source 100 and transform the radiant energy within the treatment device 106 via the liquid or liquid composition within the second opening 115 to produce a desired radiant energy emitted out through the first outlet 113. In other words, the waveguide characteristics of the treatment device 106 may be changed as desired according to the refractive index of the fluid introduced into the treatment device 106. Said another way, the numerical aperture of the treatment device 106 may be altered as desired or otherwise determined according to type of fluid introduced into the treatment device 106. In one simplified example where the fluid source is a saline solution administered to a target subject, a first commercially available saline solution product may have a higher salt content than a second commercially available saline solution product, changing the index of refraction of the fluid of the system. In such situation where the first saline solution product is replaced by the second saline solution product for a particular target subject, the output of electromagnetic radiation at the radiation source 100 may need to be adjusted to ensure a substantially similar emission of electromagnetic radiation out from the treatment device 106. Likewise, the radiation source 100 may need to be adjusted to ensure a substantially similar emission of electromagnetic radiation out from the treatment device 106 when the index of refraction of a known fluid is changed by the addition of one or more one or more therapeutic agents to the fluid being administered to a target subject. Thus, it is herein contemplated that one or more calculations may be made to determine a particular frequency and amplitude of radiant energy to be emitted from a treatment device 106 or treatment assembly 200, 300 (discussed below) based on the index of refraction of the fluid or fluid solution used in addition to other system characteristics or parameters. Such calculations may also take into account degradation qualities of the waveguide 102 and/or treatment device 106 being used.

The treatment device 106 may also include one or more optical interfaces 120 located between the first inlet 111 and the second opening 115 for transforming electromagnetic radiation transmitted through the treatment device 106. In one example, one or more optical interfaces 120 may be located at the junction between the first opening 114 and the second opening 115. In still another embodiment, one or more optical interfaces 120 may be located at one or more points within the second opening 115. The one or more optical interfaces 120 are suitably operationally configured to transform the electromagnetic radiation received from the waveguide 102 into a particular type of electromagnetic beam 126 (see for example FIG. 5) to be emitted out from the treatment device 106 via the first outlet 113. In still another implementation, it is further contemplated that the system may be operationally configured to produce a particular radiant energy at the radiation source 100 and transform the radiant energy within the treatment device 106 via the liquid or liquid composition within the second opening 115 and one or more optical interfaces 120 to transform the electromagnetic radiation received from the waveguide 102 into a particular type of electromagnetic beam 126 to be emitted out through the first outlet 113.

As understood by a skilled artisan, electromagnetic radiation 125 propagates through a waveguide, such as an optical fiber, according to the phenomenon of total internal reflection (see for example FIG. 5). By employing one or more optical interfaces 120 the present treatment device 106 is operationally configured to transform, e.g., decrease the spatial cross section of the electromagnetic radiation 126 as desired. It is also contemplated that the frequency and amplitude of the electromagnetic radiation 125 may be changed and/or controlled via non-linear conversions including, but not necessarily limited to the addition of quantum dots to fluid entering the treatment device 106.

In one implementation, the one or more optical interfaces 120 of the present application may be described as optical lenses. Suitable optical lenses include, but are not necessarily limited to parallel radiant energy forming lenses, grin lenses, focusing lenses, and combinations thereof. In one embodiment, the treatment device 106 may include a parallel radiant energy forming lens 120 within the first body 109 or adjacent the first inlet 111 or first outlet 113. For example, the lens 120 may include a collimating lens operationally configured to transform electromagnetic radiation into parallel electromagnetic beams as shown in the simplified illustration of FIG. 5. In one embodiment, the numerical aperture of a collimating lens is about equal to the numerical aperture of the source, i.e., the waveguide coupled to the collimator. In another embodiment, the numerical aperture of a collimating lens is greater than the numerical aperture of the source. In another embodiment, the numerical aperture of a collimating lens is less than the numerical aperture of the source.

In another embodiment, one or more optical interfaces 120 may be provided as grin lenses (as understood by persons of ordinary skill in the art of gradient-index optics) operationally configured to substantially match the propagation of electromagnetic radiation received from a waveguide 102 into the propagation defined by treatment device 106 and/or the hollow puncture forming member 150 (see FIG. 6) attached thereto. In another embodiment, one or more optical interfaces 120 may be provided as focusing lenses operationally configured to focus substantially all of the radiant energy exiting the waveguide 102 into a hollow puncture forming member 150 in radiant communication there with. Thus, in one embodiment the distance of the proximal end 152 of a hollow puncture forming member 150 from an optical interface 120 may be determined according to the focal length of the optical interface 120.

In one non-limiting embodiment, the focusing lens may include, but is not necessarily limited to a plano-convex lens. Depending on (1) the desired radiant energy output conveyed to a target, and/or (2) the configuration of the waveguide 102 and/or the treatment device 106 and/or the hollow puncture forming member 150, one or more optical interfaces 120 including, but not necessarily limited to plano-convex lenses, biconvex lenses, positive meniscus lenses, negative meniscus lenses, plano concave lenses, biocancave lenses, and combinations thereof may be employed as desired.

As shown in FIGS. 5 and 6, optical interfaces 120 may extend across substantially the entire width or diameter of the opening where housed in a manner effective to prevent radiant energy from passing out around the perimeter of the optical interface 120. In one embodiment, an optical interface 120 may be located at the junction between a first opening 114 and the second opening 115 whereby the optical interface 120 extends across the whole inner surface of the first opening 114 ensuring that the radiant energy intended to exit out from the first outlet 113 first propagates through the optical interface 120. In another embodiment as shown in FIG. 7, including an optical interface 120 located at the junction between a first opening 114 and the second opening 115, the optical interface 120 may be located within the second opening 115 extending across substantially the entire inner diameter of the second opening 115 in a manner effective to prevent radiant energy from passing out around the perimeter of the optical interface 120.

With reference again to FIG. 6, the first outlet 113 may be operationally configured to receive a hollow puncture forming member 150 in permanent or releasable attachment thereto. Suitably, the hollow puncture forming member 150 lies in both radiant communication and fluid communication with the second opening 115 in a manner effective to (1) receive and emit electromagnetic radiation and (2) receive and discharge fluid out through the open tip 151 of the hollow puncture forming member 150 (see for example FIG. 8). Thus, in one embodiment the hollow puncture forming member 150 suitably comprises an inner surface operationally configured to act as a waveguide, e.g., a liquid light guide, for guiding electromagnetic radiation out through the open tip 151. As such, the treatment device 106 may be defined as having at least two waveguides in radiant communication for delivery of electromagnetic radiation from a waveguide 102 to a target site of a subject 10 out beyond the open tip 151.

Referring to FIGS. 6-7, the first outlet 113 and second opening 115 may provide a female type mating surface for receiving a hollow puncture forming member 150 therein. Although a hollow puncture forming member 150 may be mated to a functionally desirable depth within the second opening 115, the proximal end 152 of the hollow puncture forming member 150 suitably remains downstream of the junction 129 between second opening 115 and third opening 116 during operation. To ensure such configuration, the inner surface of the second opening 115 may include a raised surface as desired operationally configured to act as a stop for preventing travel distance of a hollow puncture forming member 150 beyond such stop. In another embodiment (not shown), the second opening 115 may be provided as a threaded connection for receiving a corresponding hollow puncture forming member 150 in threaded connection thereto. In still another embodiment, the hollow puncture forming member 150 may include a hub 155 operationally configured to attach to or slip onto the first body 109 whereby the opening of the hollow puncture forming member 150 is axially aligned with the longitudinal axis A-A of the first body 109 (see for example FIGS. 9 and 10).

Without limiting the invention to a particular embodiment, one exemplary hollow puncture forming member 150 may include a cannula. In another embodiment, the hollow puncture forming member 150 may include an intravenous cannula. Cannula may have a blunt end, e.g., blunt-tip microcannula, beveled blunt end cannula, or deflected tip point as desired. Suitable cannula may be constructed from one or more materials, including non-static materials, including but not necessarily limited to metals, plastics, composite materials, crystalline materials, and combinations thereof. In one exemplary embodiment, a cannula may be constructed from stainless steel. In another exemplary embodiment, a cannula may be constructed from hyperchrome stainless steel tubing. Cannula may also include lancent points as desired.

In another embodiment, the hollow puncture forming member 150 may include a hollow needle type device. Suitable needles may include, but are not necessarily limited to reusable or disposable hypodermic needles, emulsifying needles, lancet point needles, non-coring needles, and pipetting needles constructed from one or more materials, for example non-static materials, including but not necessarily limited to metals, plastics, composite materials, crystalline materials, and combinations thereof. Suitable hypodermic needle materials of construction include, but are not necessarily limited to aluminum, tantalum, stainless steel, niobium, nickel iron alloys, nickel alloys, molybdenum, silicon, polymeric materials, composite materials, and combinations thereof. In another embodiment, hypodermic needles may be constructed from polytetrafluoroethylene ("PTFE"). Hypodermic needles may also include one or more tipping technologies to effect hypodermic injections or to otherwise enhance penetration of a surface of a target site. Suitable tipping technologies include, but are not necessarily limited to tips coated with PTFE. Because the treatment device 106 may be built to scale, the needle to be employed is not necessarily limited to any particular gauge or range of gauges.

In still another embodiment, the hollow puncture forming member 150 may include a catheter or flexible catheter tube operationally configured to be inserted into a target body cavity, duct, or vessel. Suitable catheters may include, but are not necessarily limited to angioplasty catheters, internal drug delivery catheters, laser ablation catheters, ultrasonic ablation catheters, thermal or mechanical disruptive catheters, stent delivery catheters, catheters for monitoring drug or other chemical concentrations/indications in vivo, and catheters for monitoring body functions (e.g., cardiac output). One exemplary catheter may include a tapered PTFE catheter.

In still another embodiment, the hollow puncture forming member 150 may include a liquid light guide. In one embodiment, the treatment device 106 may be operationally configured to receive a light guide adapter in releasable attachment thereto for communicating the treatment device 106 with the liquid light guide. In another embodiment, the distal end of the treatment device 106 or first outlet 113 may be operationally configured to receive a liquid light guide in direct attachment thereto.

In one aspect, the hollow puncture forming member 150 may provide for atraumatic insertion for providing radiant energy and one or more therapeutic agents as described above. Depending on the intended use, a particular hollow puncture forming member 150 may also be provided as a medical grade device, e.g., sterile, disposable, reusable. As stated, the treatment device 106 and hollow puncture forming member 150 may be built to scale for a particular operation. Said another way, treatment using the present device, assembly, system and method is scalable whereby larger inner width or inner diameter hollow puncture forming members 150 may be operationally configured to convey more radiant energy there through than smaller hollow puncture forming members 150. Although the treatment device 106 and hollow puncture forming member 150 may be built to scale, for the purposes of subcutaneous applications in animals, suitable hollow puncture forming members 150 may include hypodermic needles according to, but not necessarily limited to the size characteristics of Table 1 below.

TABLE 1

| Needle Gauge | Nominal Outer Diameter | | | Nominal Inner Diameter | | | Nominal Wall Thickness | | |
|---|---|---|---|---|---|---|---|---|---|
| | inches | mm | tol. inches (mm) | inches | mm | tol. inches (mm) | inches | mm | tol. inches (mm) |
| 7 | 0.180 | 4.572 | ±0.001 (±0.025) | 0.150 | 3.810 | ±0.003 (±0.076) | 0.015 | 0.381 | ±0.001 (±0.02) |
| 8 | 0.165 | 4.191 | " | 0.135 | 3.429 | " | " | " | " |
| 9 | 0.148 | 3.759 | " | 0.118 | 2.997 | " | " | " | " |
| 10 | 0.134 | 3.404 | " | 0.106 | 2.692 | " | 0.014 | 0.356 | " |
| 11 | 0.120 | 3.048 | " | 0.094 | 2.388 | " | 0.013 | 0.330 | " |
| 12 | 0.109 | 2.769 | " | 0.085 | 2.159 | " | 0.012 | 0.305 | " |
| 13 | 0.095 | 2.413 | " | 0.071 | 1.803 | " | " | " | " |
| 14 | 0.083 | 2.108 | " | 0.063 | 1.600 | " | 0.01 | 0.254 | " |
| 15 | 0.072 | 1.829 | ±0.0005 (±0.013) | 0.054 | 1.372 | ±0.0015 (±0.038) | 0.009 | 0.229 | ±0.0005 (±0.013) |
| 16 | 0.065 | 1.651 | " | 0.047 | 1.194 | " | " | " | " |
| 17 | 0.058 | 1.473 | " | 0.042 | 1.067 | " | 0.008 | 0.203 | " |
| 18 | 0.050 | 1.270 | " | 0.033 | 0.838 | " | 0.0085 | 0.216 | " |
| 19 | 0.042 | 1.067 | " | 0.027 | 0.686 | " | 0.0075 | 0.191 | " |
| 20 | 0.03575 | 0.9081 | ±0.00025 (±0.0064) | 0.02375 | 0.603 | ±0.00075 (±0.019) | 0.006 | 0.1524 | ±0.00025 (±0.0064) |
| 21 | 0.03225 | 0.8192 | " | 0.02025 | 0.514 | " | " | " | " |
| 22 | 0.02825 | 0.7176 | " | 0.01625 | 0.413 | " | " | " | " |
| 22s | " | " | " | 0.006 | 0.152 | " | 0.0111 | 0.2826 | " |
| 23 | 0.02525 | 0.6414 | " | 0.01325 | 0.337 | " | 0.006 | 0.1524 | " |
| 24 | 0.02225 | 0.5652 | " | 0.01225 | 0.311 | " | 0.005 | 0.1270 | " |
| 25 | 0.02025 | 0.5144 | " | 0.01025 | 0.260 | " | " | " | " |
| 26 | 0.01825 | 0.4636 | " | " | " | " | 0.004 | 0.1016 | " |
| 26s | 0.01865 | 0.4737 | " | 0.005 | 0.127 | " | 0.0068 | 0.1734 | " |
| 27 | 0.01625 | 0.4128 | " | 0.00825 | 0.210 | " | 0.004 | 0.1016 | " |
| 28 | 0.01425 | 0.3620 | " | 0.00725 | 0.184 | " | 0.0035 | 0.0889 | " |
| 29 | 0.01325 | 0.3366 | " | " | " | " | 0.003 | 0.0762 | " |
| 30 | 0.01225 | 0.3112 | " | 0.00625 | 0.159 | " | " | " | " |
| 31 | 0.01025 | 0.2604 | " | 0.00525 | 0.133 | " | 0.0025 | 0.0635 | " |
| 32 | 0.00925 | 0.2350 | " | 0.00425 | 0.108 | " | " | " | " |
| 33 | 0.00825 | 0.2096 | " | " | " | " | 0.002 | 0.0508 | " |
| 34 | 0.00725 | 0.1842 | " | 0.00325 | 0.0826 | " | " | " | " |

It is also contemplated that a suitable hollow puncture forming member 150 may include a hypodermic needle according to, but not necessarily limited to the size characteristics of Table 2 below.

TABLE 2

| Needle Gauge | Nominal O.D. | | | Nominal I.D. | | |
|---|---|---|---|---|---|---|
| | mm | inches | tol. (in.) | mm | inches | tol. (in.) |
| 10 | 3.404 | 0.1340 | ±0.0010 | 2.692 | 0.1060 | ±0.0020 |
| 11 | 3.048 | 0.1200 | " | 2.388 | 0.0940 | " |
| 12 | 2.769 | 0.1090 | " | 2.159 | 0.0850 | " |
| 13 | 2.413 | 0.0950 | " | 1.803 | 0.0710 | " |
| 14 | 2.108 | 0.0830 | " | 1.600 | 0.0630 | " |
| 15 | 1.829 | 0.0720 | ±0.0005 | 1.372 | 0.0540 | ±0.0015 |
| 16 | 1.651 | 0.0650 | " | 1.194 | 0.0470 | " |
| 17 | 1.473 | 0.0580 | " | 1.067 | 0.0420 | " |
| 18 | 1.270 | 0.0500 | " | 0.838 | 0.0330 | " |
| 19 | 1.067 | 0.0420 | " | 0.686 | 0.0270 | " |
| 20 | 0.902 | 0.0355 | +0.0005 −0.0000 | 0.584 | 0.0230 | +0.0015 −0.0000 |
| 21 | 0.813 | 0.0320 | " | 0.495 | 0.0195 | " |
| 22 | 0.711 | 0.0280 | " | 0.394 | 0.0155 | " |
| 22s | 0.711 | 0.0280 | " | 0.140 | 0.0055 | " |
| 23 | 0.635 | 0.0250 | " | 0.318 | 0.0125 | " |
| 24 | 0.559 | 0.0220 | " | 0.292 | 0.0115 | " |
| 25 | 0.508 | 0.0200 | " | 0.241 | 0.0095 | " |
| 25s | 0.508 | 0.0200 | " | 0.140 | 0.0055 | " |
| 26 | 0.457 | 0.0180 | " | 0.241 | 0.0095 | " |
| 26s | 0.467 | 0.0184 | " | 0.114 | 0.0045 | " |
| 27 | 0.406 | 0.0160 | " | 0.191 | 0.0075 | " |
| 28 | 0.356 | 0.0140 | " | 0.165 | 0.0065 | " |
| 29 | 0.330 | 0.0130 | " | 0.165 | 0.0065 | " |
| 30 | 0.305 | 0.0120 | " | 0.140 | 0.0055 | " |
| 31 | 0.254 | 0.0100 | " | 0.114 | 0.0045 | " |
| 32 | 0.229 | 0.0090 | " | 0.089 | 0.0035 | " |
| 33 | 0.203 | 0.0080 | " | 0.089 | 0.0035 | " |

In animals, the length of a particular hypodermic needle employed suitably includes a length operationally configured to convey electromagnetic radiation to one or more particular subcutaneous target sites. In other words, the length of a particular hypodermic needle may be determined according to the size of the target subject. Without limiting the length of hypodermic needles to a particular range, for the purposes of subcutaneous applications in animals, suitable lengths may include from about 0.01 mm to about 5.0 meters. In human applications, a suitable hypodermic needle may range in length from about 1.0 mm to about 50.0 cm. In another embodiment, it is contemplated that nanoneedles (as understood by the skilled artisan) may be employed. It is also contemplated that varying needle point styles may be employed as desired.

Figure 11:
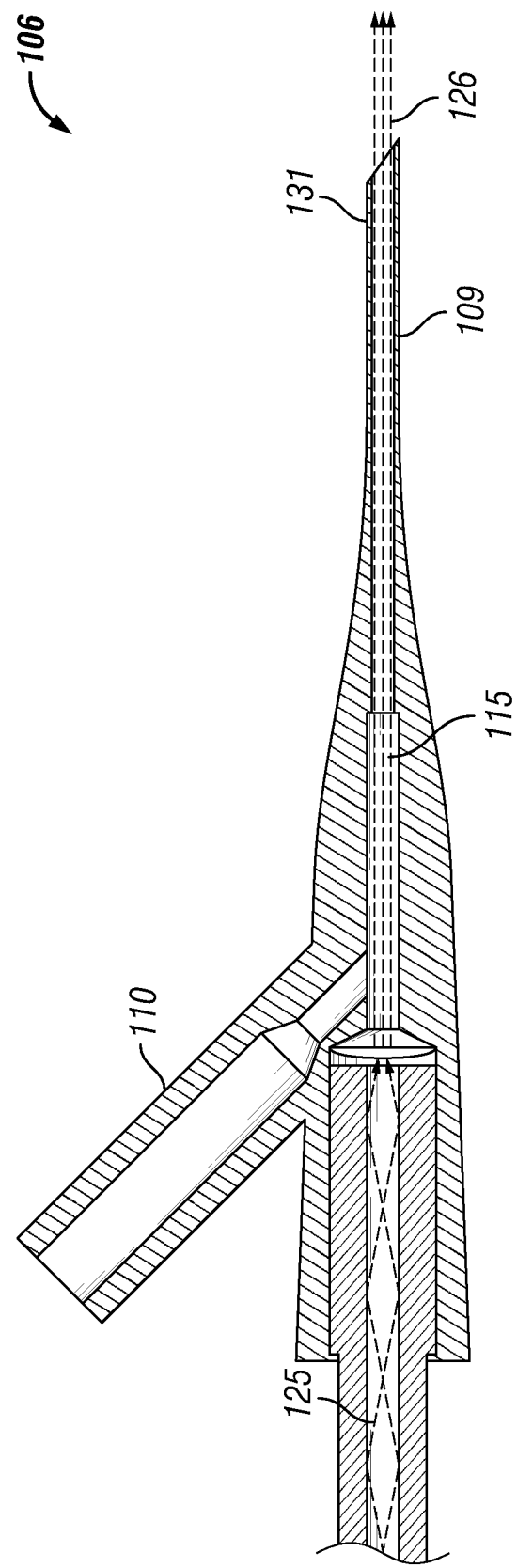
FIG. 11 illustrates a sectional side view of another simplified embodiment of a treatment device.

As shown in FIG. 10, the hollow puncture forming member 150 may be provided with wings 130 (also commonly referred to as a "butterfly" by persons of ordinary skill in the art of healthcare services) to allow for easy fixation of the treatment device 106 to a target subject 10 to help prevent pistoning and/or rolling of the treatment device 106 during operation. In other embodiments, it is contemplated that the first body 109 itself may include a puncture forming outer surface configuration at a distal end 131 (see FIG. 11). In one particular embodiment, the treatment device 106 may be provided as a tapered PTFE device providing for atraumatic insertion of the first body 109.

Figure 12:
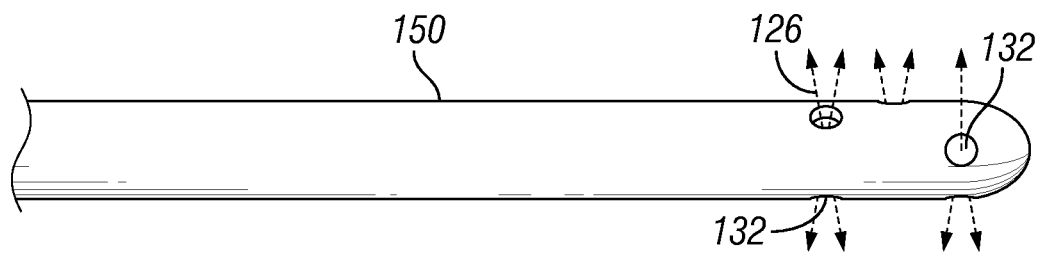
FIG. 12 illustrates a distal portion of an embodiment of a hollow member of the present application.
Figure 13:
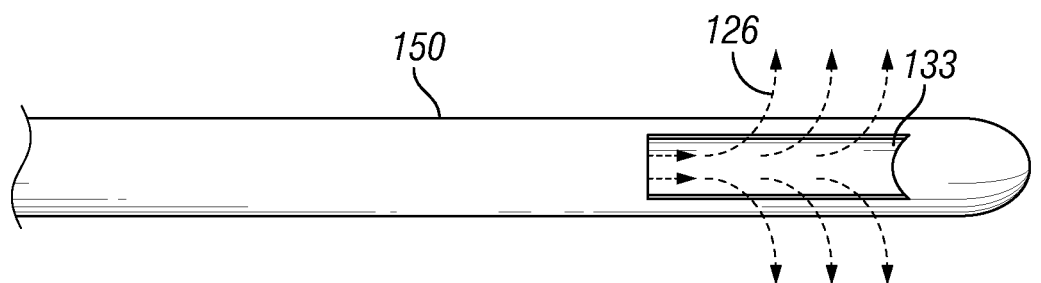
FIG. 13 illustrates a distal portion of an embodiment of a hollow member of the present application.

With attention to FIG. 12, the distal portion of a hollow member or a hollow puncture forming member 150 or first body 109 may include a closed tip with one or more apertures 132 located at or near the tip of the hollow puncture forming member 150 operationally configured for conveyance of electromagnetic radiation there through. In another embodiment, the distal portion of the hollow member or hollow puncture forming member 150 or first body 109 may include a closed tip comprising one or more transparent materials, one or more partially transparent materials, one or more translucent materials, one or more partially translucent materials, and combinations thereof forming one or more windows 133 near the closed tip operationally configured for conveyance of electromagnetic radiation there through (see FIG. 13). In another embodiment, a hollow puncture forming member 150 or first body 109 may include a combination of the elements of FIGS. 12 and 13. In still another embodiment, a hollow puncture forming member 150 or first body 109 may include an open tip 151 or first outlet 113 in addition to the elements of FIGS. 12 and 13.

Turning to FIGS. 14A-14C, another simplified embodiment of a treatment device 106 is provided. Like the embodiment described above, the treatment device 106 of this embodiment suitably includes a hollow first body 109 having a longitudinal axis C-C and a second body 110 in communication with the first body 109 and having a longitudinal axis D-D, the first body 109 being operationally configured to receive a waveguide 102 at a first end and a hollow puncture forming member 150 at a second end, the second body 110 being operationally configured to receive a fluid conduit 107 in attachment thereto. Other non-linear configurations of the bodies 109 and 110 are also contemplated for implementation with this particular embodiment of the treatment device 106. In one implementation, the second body 110 may be flexible or bendable.

With attention to FIGS. 14A-B, the treatment device 106 may further include a conduit 134 in fluid communication with the second body 110 at a first end and operationally configured to receive a fluid conduit 107 in fluid communication thereto. The conduit 134 may be provided as a substantially straight member in axial alignment according to longitudinal axis D-D. In another embodiment, the conduit 134 may be provided as a non-linear member as shown. A conduit 134 may be constructed from one or more rigid materials and/or one or more flexible materials as desired. For example, the conduit 134 may be constructed from one or more metals, polymeric materials, rubbers, glass, plexiglass, filled composite materials, and combinations thereof. Likewise, the conduit 134 may include a length as desired for a particular use. Where the treatment device 106 is to be used to convey radiant energy to a subcutaneous site of an animal, the conduit 134 suitably includes a shape and/or a length providing for adequate manipulation and/or placement of the treatment device 106 and fluid conduit 107 for ease of operation. For use with persons, the conduit 134 may be provided as a flexible tube constructed from one or more polymeric materials and have a length from about 1.27 cm to about 30.48 (about 0.5 inches to about 12.0 inches). With reference to FIG. 14A, one suitable conduit 134 for use with a person 10 has a length of about 11.43 cm (about 4.5 inches).

In one suitable embodiment, the conduit 134 engages the second body via a sealable connection to minimize fluid loss out from the point of attachment between the conduit 134 and the second body 110. In another suitable embodiment, an interconnector may be used to join the conduit 134 to the second body 110 as a snap fit or threaded type male/female fitting. In another suitable embodiment, the distal end of the conduit 134 may include a mating surface or other connector operationally configured to mate or otherwise engage the second inlet 112 or second body 110. In addition, the first inlet 111 is operationally configured to receive a waveguide 102 in radiant communication there with in a manner effective to prevent or otherwise minimize leakage, emission or escape of electromagnetic radiation from within the first body 109, e.g., at a junction between the first body 109 and the waveguide 102.

The treatment device 106 of FIGS. 14A-14C suitably includes one or more optical interfaces 120 housed within a compartment 135 near the first inlet 111 in a manner effective to transform radiant energy received therein to produce a treatment dose of radiant energy emitted out through the tip 151 of the hollow puncture forming member 150. In one particular embodiment, the treatment device 106 is operationally configured emit radiant energy and fluid received through the conduit 134 out through the tip 151.

As shown in the exploded view of FIG. 14C, the treatment device 106 may be provided as an assembly including a first body 109 permanently or releasably attachable to a corresponding conduit 134, a hollow intermediary winged member 136 permanently or releasably attachable to the first body 109 to allow for easy fixation of the treatment device 106 to a target subject 10 to help prevent pistoning and/or rolling of the treatment device 106 during operation, the winged member 136 being axially aligned with the longitudinal axis C-C, and a hollow puncture forming member 150 permanently or releasably attachable to the winged member 136, the hollow puncture forming member 150 being axially aligned with the longitudinal axis C-C.

The hollow intermediary winged member 136 may be substantially planar or include a surface ornamentation effective to abut an outer surface as desired. For example, the hollow intermediary winged member 136 may include a curved surface operationally configured to abut the curvature of the surface of a person's 10 arm. Likewise, the hollow intermediary winged member 136 (or other portion of the treatment device 106) may include an adhesive type surface for adhering the treatment device to a target surface. In addition to single use disposal of one or more of the above parts of the treatment device 106, each of the first body 109, the conduit 134, the hollow intermediary winged member 136, and the hollow puncture forming member 150 may be operationally configured for reuse in any combination.

With reference now to FIGS. 15A-15C, another simplified embodiment of a treatment device 106 is provided. The treatment device 106 of this embodiment includes a first body 109 having a first inlet 111 and first outlet 113 and a second body 110 having a second inlet 112, the second body 110 being in fluid communication with the first body 109. With attention to FIG. 15B, first body 109 may be described as having a multi-sectional or multi-compartment configuration (see Sections 1, 2 and 3). Even though the outer surface configuration of the first body 109 may vary, in the embodiment of FIGS. 15A-15C the first body 109 includes a cylindrical shape of one or more outer diameters. In particular, Section 1 has the smallest outer diameter and Section 3 has the greatest outer diameter. The particular configuration of FIGS. 15A-15C is operationally configured for use with disposable hollow puncture forming members 150. Suitably, the configuration of the treatment device 106 assists in minimizing material costs and/or production costs while also being effective for different types of treatment operations.

With attention to FIG. 15C, Section 1 of the first body 109 is operationally configured to receive a waveguide 102 in radiant communication thereto. Suitably, Section 1 includes an opening 160 defined by an inner surface 161 operationally configured to mate with a fiber optic connector 140. As shown in the simplified embodiment of FIG. 15C, the inner surface 161 of the opening 160 includes a stepped configuration effective to receive a slotted bayonet type fiber optic connector 140 such as a ST Connector in releasable attachment thereto.

Section 2 of the first body 109 suitably includes an opening 162 defined by an inner surface 163 and one or more optical interfaces 120 disposed across the opening 162 as desired. In another embodiment it is contemplated that no optical interfaces 120 are employed. As shown, the opening 162 is in radiant communication with the opening 160 of Section 1 and in fluid communication with the second body 110, the opening 162 having a first volume for receiving radiant energy and/or fluid therein including one or more fluids in an amount up to the volume of the opening 162 as received via the third opening 116. At a minimum, the opening 162 of Section 2 includes an inner surface configuration and/or volume operationally configured to direct radiant energy and a desired amount of fluid out from the opening 162 into the opening 164 of Section 3, which is in radiant and fluid communication with opening 162. Section 3 may also include an inner surface 165 configuration effective to assist in directing radiant energy and/or fluid from the opening 162 out through the first outlet 113. In this particular embodiment, the opening 164 includes a funnel type configuration 166 at the junction with the opening 162 operationally configured to optimize the amount of radiant energy entering the opening 164. Likewise, the first outlet 113 of the opening 164 is operationally configured to receive a hollow puncture forming member 150 in attachment thereto. Thus, in one exemplary mode of operation, radiant energy and/or fluid suitably exits the treatment device 106 via the first outlet 113 or a hollow puncture forming member 150 attached thereto. Suitably, the fluid and radiant energy are conveyed in a manner effective for the hollow puncture forming member 150 attached thereto to act optically similar to a liquid light guide as understood by persons of ordinary skill in the art.

As shown in FIG. 15C, the opening 164 may include a cylindrical shape, but the inner surface 165 of the opening 164 may include a different surface configuration (1) for receiving a particular shaped hollow puncture forming member 150 therein and/or (2) for acting on the radiant energy and/or fluid conveyed there through as desired. Section 3 may also include a threaded surface 167 as desired for receiving a hollow member, e.g., a hollow puncture forming member 150 in releasable attachment thereto. In addition, the second body 110 may be disposed about 45.0 degrees relative to the longitudinal axis of the treatment device 106 as shown or, in another embodiment, the second body 110 may be disposed substantially perpendicular to the longitudinal axis of the treatment device 106.

Figure 16:
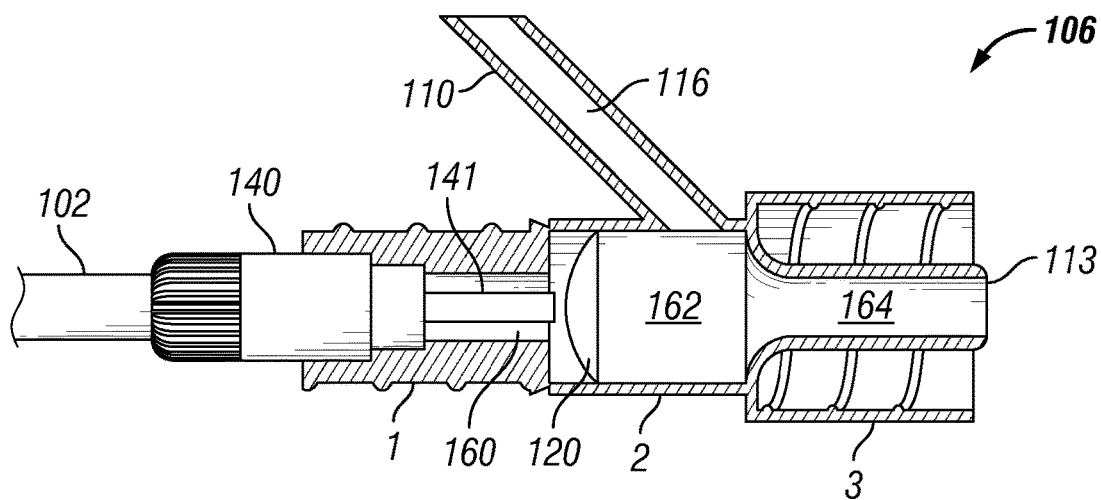
FIG. 16 illustrates a sectional view of a simplified embodiment of a treatment device including a waveguide attached thereto.

Referring now to FIG. 16, Section 2 of this embodiment suitably includes one or more optical interfaces 120 disposed across the inner surface 163 of the opening 162 in a manner effective to transform the electromagnetic radiation received from the waveguide 102 into one or more particular types of electromagnetic beams to be emitted out through first outlet 113. As shown, the inner surface 161 suitably receives the fiber optic connector 140 in releasable attachment whereby the distal end of the ferrule 141 of the connector extends to a point functionally near or in abutment with an optical interface 120. In operation, fluid and radiant energy are combined in the opening 162 in a manner effective for the hollow puncture forming member 150 to operate as a waveguide, e.g., a liquid light guide.

Figure 17:
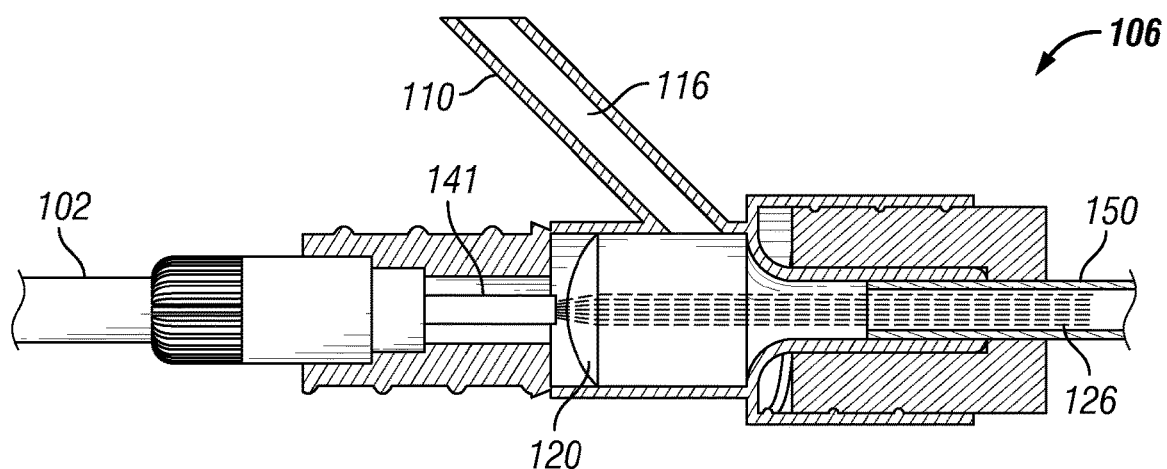
FIG. 17 illustrates a sectional view of a simplified embodiment of a treatment device including a waveguide attached thereto illustrating propagation and transformation of the electromagnetic radiation through the treatment device.
Figure 18:
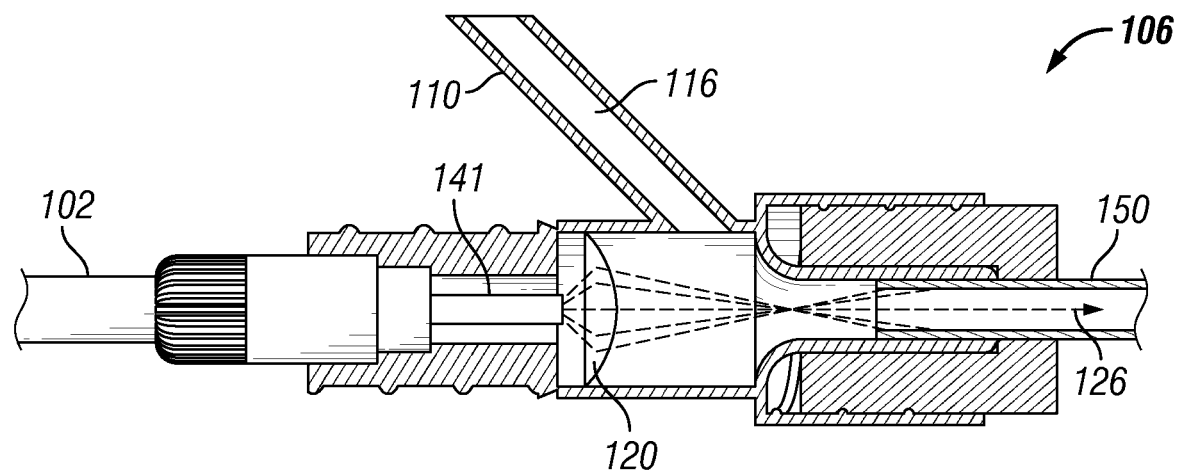
FIG. 18 illustrates another sectional view of a simplified embodiment of a treatment device including a waveguide attached thereto illustrating propagation and transformation of electromagnetic radiation through the treatment device.
Figure 19:
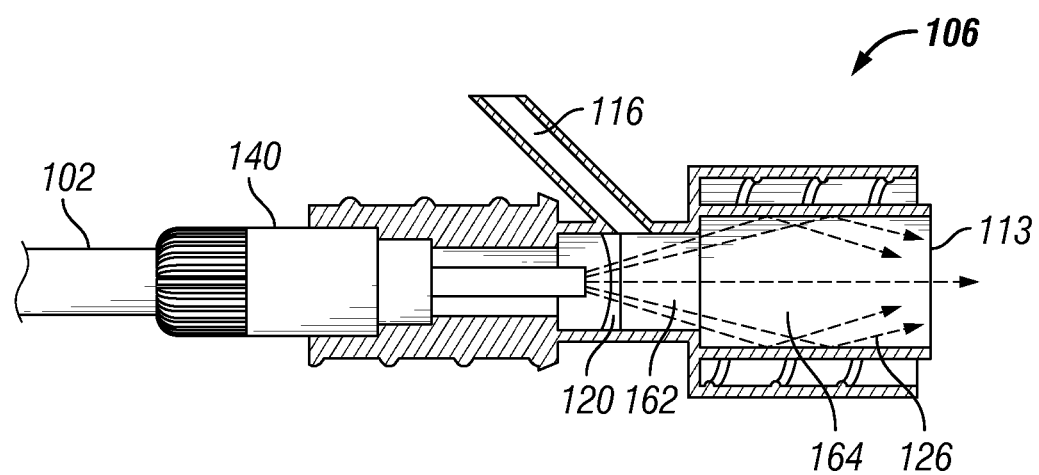
FIG. 19 illustrates another sectional view of a simplified embodiment of a treatment device including a waveguide attached thereto illustrating propagation and transformation of electromagnetic radiation through the treatment device.

In this embodiment, the one or more optical interfaces 120 are operationally configured to transform the electromagnetic radiation 125 received from a waveguide 102 in a manner effective to emit beam(s) 126 out through the first outlet 113 and/or hollow puncture forming member 150 attached thereto as desired. As shown in FIG. 17, an optical interface 120 may be provided as a collimator type lens operationally configured to transform electromagnetic radiation into substantially parallel beams 126 as shown. In another embodiment, an optical interface 120 may be provided as a converging or focusing type lens operationally configured to transform electromagnetic radiation as shown in FIG. 18. In still another embodiment, an optical interface 120 may be provided as a diverging type lens (see FIG. 19) where the treatment device 106 includes an opening 164 larger than the opening 162 housing the optical interface 120.

Figure 20:
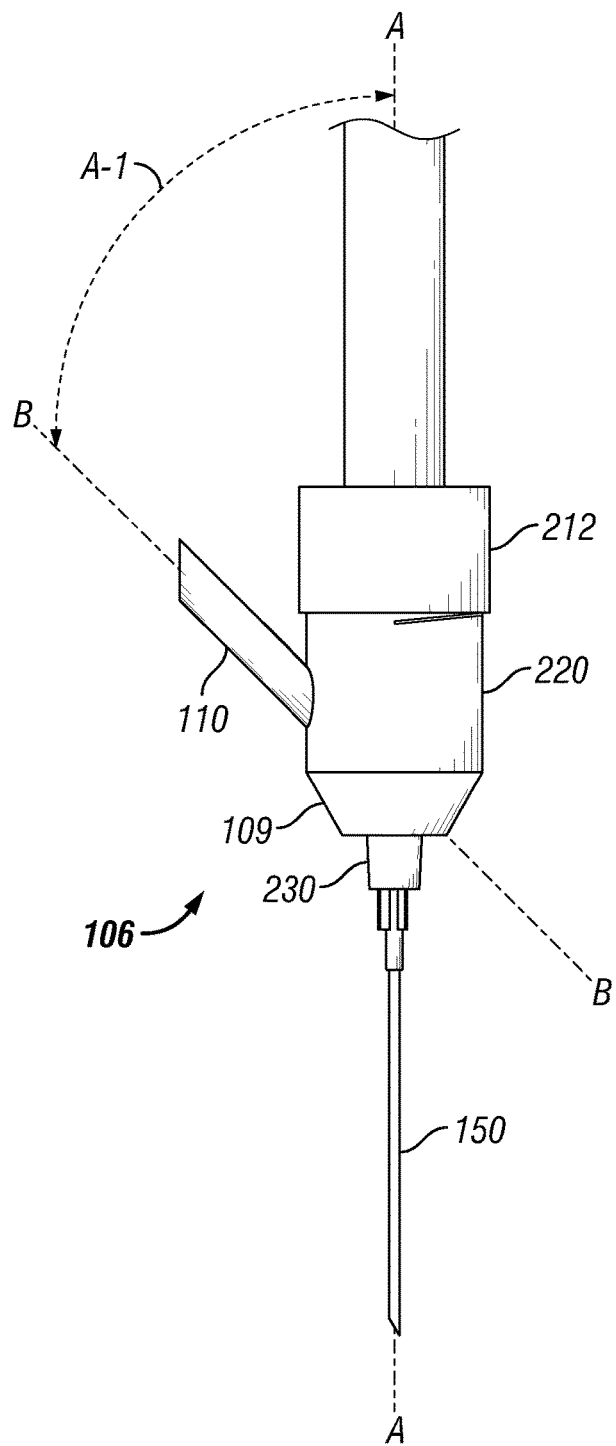
FIG. 20 illustrates another simplified embodiment of a treatment device of the present application including a waveguide and hollow member attached thereto.
Figure 21:
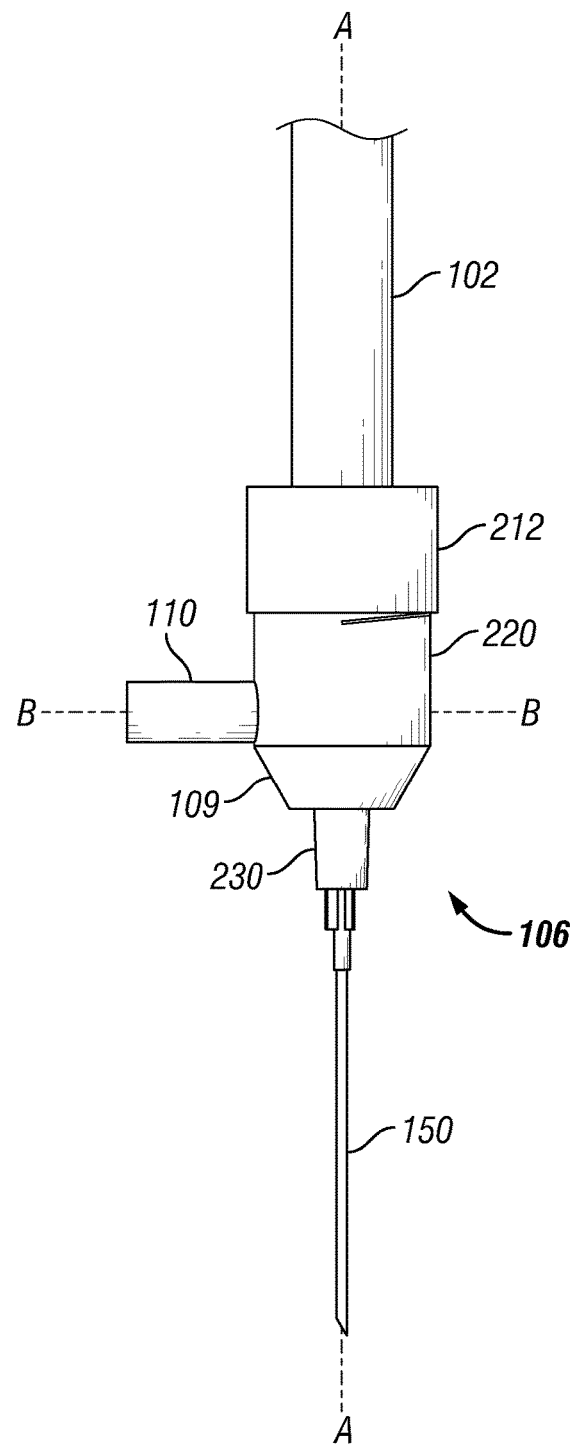
FIG. 21 illustrates another simplified embodiment of a treatment device of the present application including a waveguide and hollow member attached thereto.

Turning now to FIGS. 20 and 21, two other embodiments of the treatment device 106 are provided. As FIG. 20 illustrates, the second body 110 may extend from the first body 109 according to angle A-1. As shown in FIG. 21, the second body 110 may extend from the first body 109 in a substantially perpendicular orientation relative to the longitudinal axis A-A of the treatment device 106 suitable for supplying one or more fluids to the first body 109. Surface configurations of the first and second bodies 109, 110 may vary according to one or more particular applications as desired.

Figure 22:
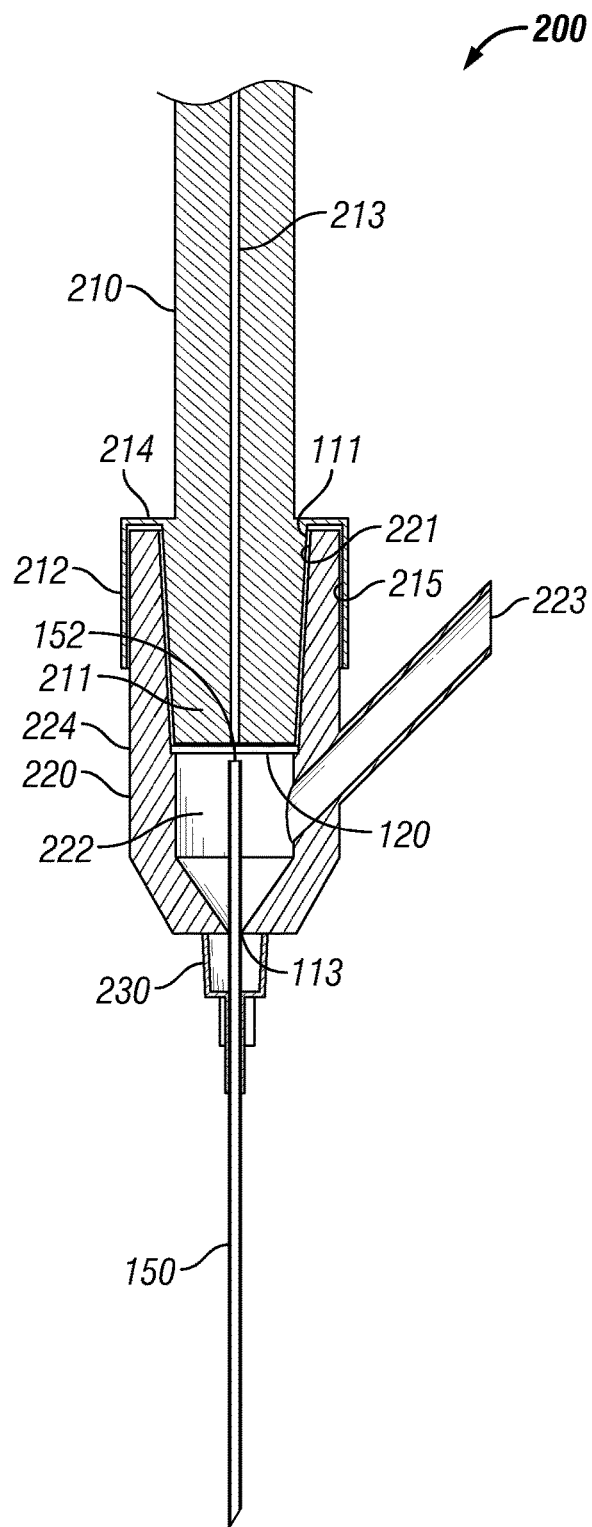
FIG. 22 illustrates a sectional view of a simplified embodiment of a treatment device of the present application including a waveguide and hollow member attached thereto.
Figure 23:
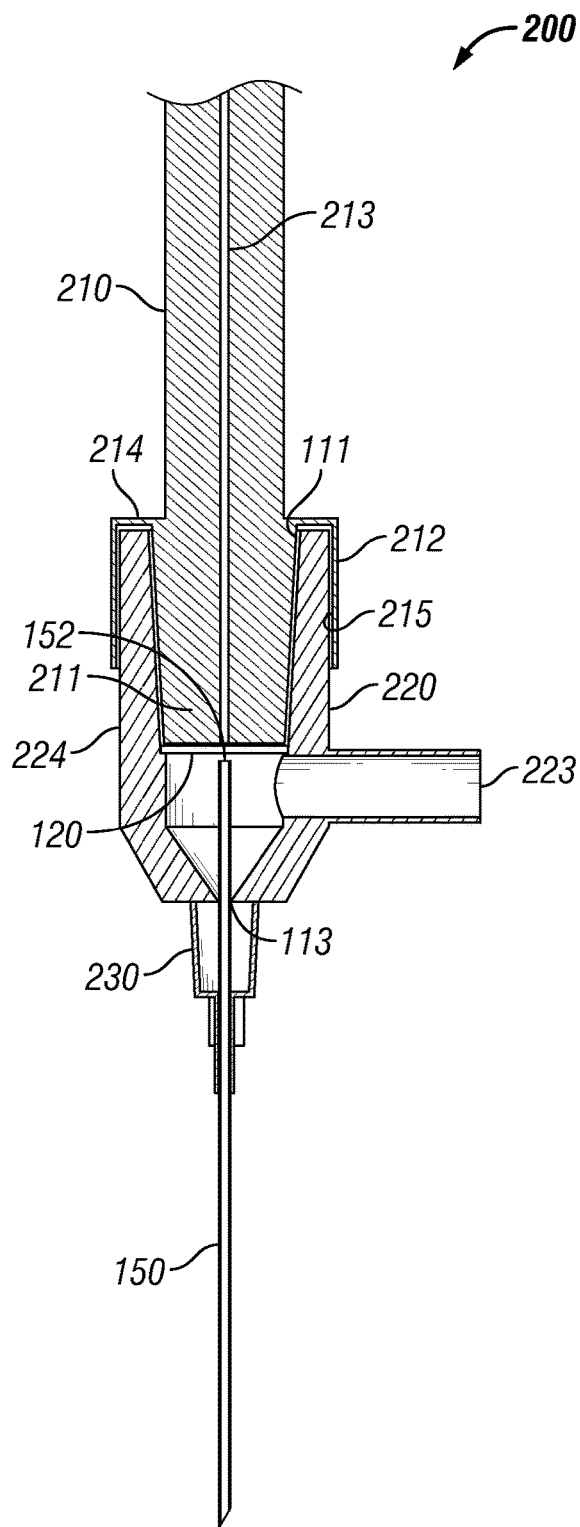
FIG. 23 illustrates a sectional view of a simplified embodiment of a treatment device of the present application including a waveguide and hollow member attached thereto.

The embodiments of FIGS. 20 and 21 are particular assemblies operationally configured to seal or otherwise separate the waveguide 102 from the hollow puncture forming member 150 attached thereto. As shown in FIGS. 22 and 23, the treatment device 106 may be provided as an assembly 200 of one or more reusable component parts and/or one or more disposable component parts. Although the various component parts may be assembled as desired, in one mode of operation it is contemplated to manufacture the treatment device (or as may be referred to here as a "treatment assembly" 200) in a manner effective to minimize manufacturing costs and/or maximize sales of various replacement component parts as desired.

In one simplified embodiment, the treatment assembly 200 may include (1) a waveguide member 210, (2) a main body 220 and (3) a hollow member assembly or a hollow puncture forming member assembly 230. In one implementation, the waveguide member 210, main body 220 and hollow puncture forming member assembly 230 may be provided assembled and following use the entire assembly 200 may be disposed of or reused. In another implementation, one or more component parts may be replaced prior to reuse of the assembly 200 as desired.

In still another implementation, the waveguide member 210, main body 220 and hollow puncture forming member assembly 230 may be provided unassembled whereby particular sized and/or shaped component parts may be fitted together for a particular purpose. For example, a hollow puncture forming member 150 of a particular length and/or gauge may be required as compared to other implementations of the assembly 200. In another embodiment, a particular volume of fluid or fluid solution may be required, which may require a main body 220 having a particular size and shape. In still another embodiment, a waveguide member 210 of a particular length (or a series of waveguides joined together) and/or inner diameter or width may be necessary for a particular treatment or use.

In one embodiment, the main body 220 includes (1) a waveguide receiving inlet 111 operationally configured to receive a waveguide member 210 in a manner effective to provide radiant communication between the main body 220 and the waveguide member 210 and (2) an outlet 113 operationally configured to receive the hollow puncture forming member assembly 230 in a manner effective to provide radiant and fluid communication between the main body 220 and the hollow puncture forming member assembly 230. As shown in FIGS. 22 and 23, the main body 220 may include a female type waveguide receiving inlet 111 defined by an inner surface 221, a fluid inlet 223, and a cavity 222 in radiant communication with the waveguide receiving inlet and in fluid communication with the fluid inlet 223. As shown, the main body 220 may further include one or more optical interfaces 120 defining the border between the waveguide receiving inlet and the cavity 222. In one particularly advantageous embodiment, the optical interface 120 may be disposed along the cavity 222 in a manner effective to fluidly seal the cavity 222 from the waveguide receiving inlet 111. Where the assembly 200 is used on an animal, the waveguide member 210 is suitably isolated from exposure to one or more bodily fluids of an animal to be targeted with the assembly 200. In one embodiment, the optical interface 120 may include a lens according to the description of lenses above. In another embodiment, the optical interface 120 may include a window type member constructed from one or more transparent materials, one or more partially transparent materials, one or more translucent materials, one or more partially translucent materials, and combinations thereof for attenuation of electromagnetic radiation as desired.

Suitably, the cavity 222 is operationally configured to receive a portion of the hollow puncture forming member 150 therein up to a point of abutment of the proximal end 152 with the optical interface 120 that forms a barrier of the cavity 222. As shown, the proximal end 152 of the hollow puncture forming member 150 may lie near the optical interface 120 in a manner effective to maximize a desired amount of radiant energy and/or fluid entering the hollow puncture forming member 150. In one embodiment, the hollow puncture forming member assembly 230 may engage the distal end of the main body 220 in a manner effective to prevent or other minimize movement of the hollow puncture forming member assembly 230 during assembly 200 operation. In another embodiment, attachment of the hollow puncture forming member assembly 230 to the main body 220 may be accomplished solely by mating the hollow puncture forming member 150 with the first outlet 113 in a manner effective to prevent or other minimize movement of the hollow puncture forming member 150 during assembly 200 operation.

In another embodiment, the main body 220 and hollow puncture forming member assembly 230 may be provided as a single unit or one piece item for reuse or for one time use. In such embodiment, the orientation of the hollow puncture forming member 150 within the cavity 222 may be preset or the hollow puncture forming member assembly 230 may include a slidable or otherwise adjustable hollow puncture forming member 150 for determining the distance between the optical interface 120 and the proximal end 152 of the hollow puncture forming member 150. It is further contemplated that a slidable or otherwise adjustable hollow member or hollow puncture forming member 150 may be replaced and disposed of as desired while reusing the remaining assembly 200 component parts.

Still referring to FIGS. 22 and 23 a suitable waveguide member 210 includes a nose 211 operationally configured to mate with the female type waveguide receiving inlet 111 of the main body 220. In one embodiment, the nose 211 may be operationally configured to engage the inner surface 221 in fixed abutment thereto during operation of the assembly 200. In other embodiments, the nose 211 may engage the inner surface 221 via one or more methods including, but not necessarily limited to a snap-fit connection, a threaded connection, a push and turn connection, a screw on configuration, and a press fit connection. In another embodiment, screws, bolts, rivets and the like may be used to attach the nose 211 to the main body 220. Thus, it is further contemplated that one or more seals or gasket type members may be used between the nose 211 and the main body 220 as desired. As shown in the embodiments of FIGS. 22 and 23, the nose 211 is mated with the female type waveguide receiving inlet 111 of the main body 220 via a slotted connection.

Without limiting the invention to a particular embodiment, the orientation of the nose 211 within the waveguide receiving inlet may be determined according to one or more assembly 200 design characteristics, fluid characteristics, attenuation characteristics of the optical interface 120, the angular distribution of light exiting the waveguide member 210, the desired emission of radiant energy out from the assembly 200, and combinations thereof. As shown, the outer surface of the nose 211 may lie in substantial abutment with the inner surface 221 whereby the outlet of the core 213 of the waveguide member 210 lies near the optical interface 120 minimizing the distance of propagation of electromagnetic radiation between the waveguide member 210 and the optical interface 120. As shown, the nose 211 suitably engages the main body 220 in a manner effective to minimize loss of radiant energy out through the female type waveguide receiving inlet 111 of the main body 220. In another embodiment, the nose 211 may engage the main body 220 in a manner effective to direct radiant energy toward the optical interface 120 at a distance up to about the outer edge of the inlet waveguide receiving 111.

As shown in FIGS. 22 and 23, one suitable waveguide member 210 may include an outer skirt 212 for ease of manual operation. The inner surface 215 of the skirt 212 may be operationally configured to engage the outer surface 224 of the main body 220 in a fixed position during operation of the assembly 200. Thus, in one embodiment the wave guide member 210 may be attached to the main body 220 via the skirt 212 rather than via engagement of the nose 211 and female type waveguide receiving inlet of the main body 220 as discussed above. Without limiting the mode of engagement, the skirt 212 and outer surface 224 of the main body 220 may be attached via cooperating threads, a lug-slot connection, a push and turn connection, a snap-fit connection, via screws, bolts, rivets and the like, or otherwise latching the skirt 212 to the main body 220 as desired. As shown in the embodiments of FIGS. 22 and 23, a suitable skirt 212 may include a shoulder 214 operationally configured to abut the perimeter of the inlet 111 providing a desired depth of the nose 211 within the female type waveguide receiving inlet 111 of the main body 220.

Still referring to FIGS. 22 and 23, in one suitable embodiment at least part of the central axis of the waveguide member 210 is substantially aligned with the central axis of the hollow puncture forming member 150. In operation, radiant energy is emitted from the core 213 of the waveguide member 210 through the optical interface 120 into the proximal end 152 of the hollow puncture forming member 150, whereby the hollow puncture forming member 150 acts in a manner similar to a liquid light guide.

Figure 24:
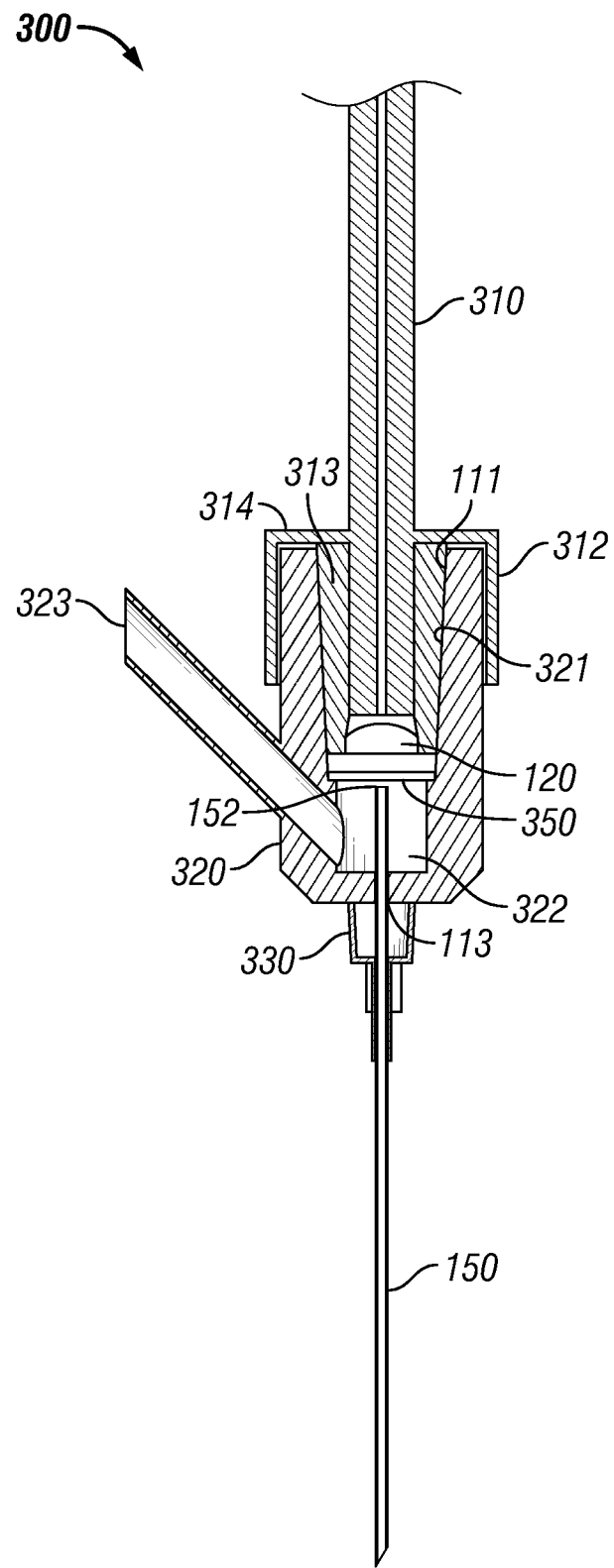
FIG. 24 illustrates a sectional view of a simplified embodiment of a treatment assembly of the present application including a waveguide and hollow member attached thereto.

Turning now to FIG. 24, another treatment assembly 300 is provided. Without limiting the assembly 300 to any particular number of assembled component parts one suitable assembly 300 may include (1) a waveguide member 310, (2) a main body 320 and (3) a hollow member assembly or hollow puncture forming member assembly 330. In one implementation, the waveguide member 310, main body 320 and hollow puncture forming member assembly 330 may be provided assembled and following use the entire assembly 300 may be disposed of or reused. In another implementation, one or more component parts of the assembly 300 may be replaced prior to reuse of the assembly 300. In still another implementation, the waveguide member 310, main body 320 and hollow puncture forming member assembly 330 may be provided unassembled whereby particular sized and/or shaped component parts may be fitted together for a particular treatment or use. For example, hollow members or hollow puncture forming member 150 of a particular length and/or gauge may be required for a particular use as compared to other implementations of the assembly 300. In another embodiment, a particular volume of fluid or fluid solution may be required, which may require a main body 320 having a particular size and shape cavity 322 for receiving fluid therein. In still another embodiment, a waveguide member 310 of a particular length (or a series of waveguides joined together) and/or inner diameter or width may be necessary for a particular treatment or use.

Figure 25:
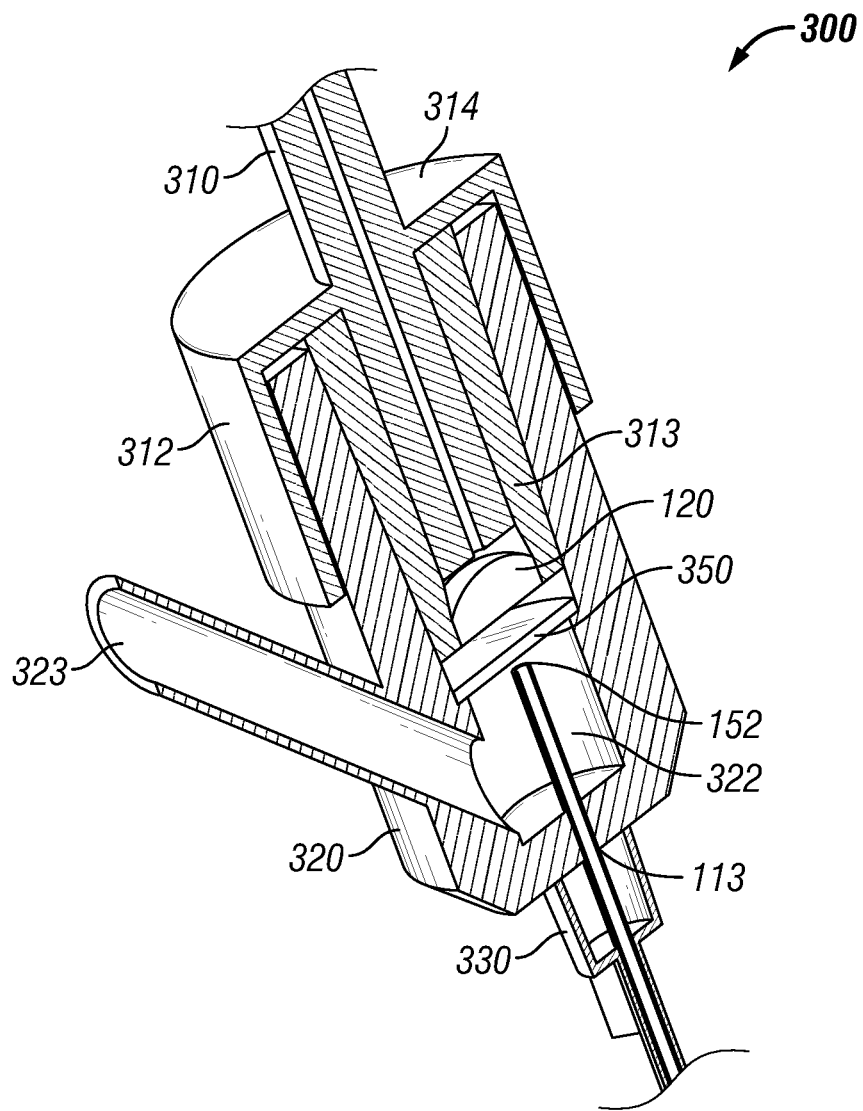
FIG. 25 illustrates a partial sectional view of a simplified embodiment of a treatment assembly of the present application including a waveguide and hollow member attached thereto.

As shown, the waveguide member 310 may include one or more waveguides 102 in series and one or more optical interfaces 120 mounted at the distal end of the waveguide 102. In one embodiment, one or more optical interfaces 120 may be permanently connected to the waveguide 102. In another embodiment, one or more optical interfaces 120 may be releasably attached to the waveguide 102 providing for interchangeability of optical interfaces 120 and varying the possible optical characteristics of the waveguide member 310 and/or assembly 300. In one embodiment, an optical interface 120 may be connected to a waveguide 102 via one or more intermediary members operationally configured to convey electromagnetic radiation from the waveguide 102 toward the optical interface 120. Without limiting the invention, suitable intermediary members may include spacer type members with apertures there through, e.g., a ring type spacer connected on one side by the waveguide 102 and connected to the optical interface 120 on its opposing side. As seen in the simplified embodiment of FIGS. 24 and 25, the waveguide member 310 includes an optical mount 313 operationally configured to surround or otherwise enclose at least part of the waveguide 102 and at least part of the optical interface 120 in a manner effective to maintain the optical interface 120 in a fixed position relative to the waveguide 102. In addition, the optical mount 313 may act as the nose of the waveguide member 310 for purposes of engaging the main body 320, thus, the outer surface of the optical mount 313 may include a surface configuration for attachment to the main body 320 as desired. For example, the optical mount 313 may engage the main body 320 in a manner similar as the nose 211 discussed above in relation to FIGS. 22 and 23. Likewise, the waveguide member 310 may include a skirt 312 and shoulder 314 similar as discussed above.

In one embodiment, the main body 320 may include (1) an inlet 111 operationally configured to receive a waveguide member 310 in a manner effective for radiant communication between the main body 320 and the waveguide member 310 and (2) an outlet 113 operationally configured to receive the hollow puncture forming member assembly 330 in a manner effective for radiant and fluid communication between the main body 320 and the hollow puncture forming member assembly 330. As shown, the main body 320 may include a female type waveguide receiving inlet 111 defined by an inner surface 321, a fluid inlet 323 and a cavity 322 in radiant communication with the female type waveguide receiving inlet 111 and in fluid communication with the fluid inlet 323. In addition, the main body 320 may include a secondary optical interface 350 defining the border between the waveguide receiving inlet 111 and the cavity 322. In one particularly advantageous embodiment, the secondary optical interface 350 may be disposed along the cavity 322 in a manner effective to fluidly seal the cavity 322 from the waveguide receiving inlet 111 and, thus, physically seal the cavity 322 from the waveguide member 310 of the assembly 300—providing separation between the waveguide member 310 and the hollow puncture forming member 150. In one embodiment, the secondary optical interface 350 may include a lens according to the description of lenses above. In another embodiment, the secondary optical interface 350 may include a substantially planar window type member constructed from one or more transparent materials, one or more partially transparent materials, one or more translucent materials, one or more partially translucent materials, and combinations thereof, for attenuation of electromagnetic radiation as desired. In one suitable embodiment, the secondary optical interface 350 may include a transparent plastic material. In another suitable embodiment, the secondary optical interface 350 may include a transparent glass material. In another suitable embodiment, the secondary optical interface 350 may include a transparent crystalline material. Without limiting the invention, a suitable a secondary optical interface 350 may include a material (1) substantially impermeable to fluids or fluid solutions entering the cavity 322 during assembly 300 operation and (2) operationally configured to affect or not affect the propagation of radiant energy guided through the assembly 300 as desired. Where the assembly 300 is used on an animal, the waveguide member 310 is suitably isolated from exposure to one or more bodily fluids of the animal to be targeted with the assembly 300.

Still referring to FIG. 24, the cavity 322 is operationally configured to receive a portion of the hollow puncture forming member 150 therein up to a point of abutment of the proximal end 152 of the hollow puncture forming member 150 with the secondary optical interface 350. As shown, the proximal end 152 of the hollow puncture forming member 150 may lie near the secondary optical interface 350 in a manner effective to maximize a desired amount of radiant energy and/or fluid entering the hollow puncture forming member 150. In one embodiment, the hollow puncture forming member assembly 330 may engage the distal end of the main body 320. For example, the outer surface of the main body 320 may be operationally configured to receive the hollow puncture forming member assembly 330 in releasable attachment thereto. In another embodiment, attachment of the hollow puncture forming member assembly 330 to the main body 320 may be accomplished solely by mating the hollow puncture forming member 150 with the first outlet 113 in a manner effective to prevent or other minimize movement of the hollow puncture forming member 150 during assembly 300 operation. In still another embodiment, the main body 320 and hollow puncture forming member assembly 330 may be provided as a single unit or one piece item for reuse or for one time use. In such embodiment, the orientation of the hollow puncture forming member 150 within the cavity 322 may be preset or the hollow puncture forming member assembly 330 may include a slidable or otherwise adjustable hollow puncture forming member 150 for determining the distance between the secondary optical interface 350 and the proximal end 152 of the hollow puncture forming member 150. It is further contemplated that a slidable or otherwise adjustable hollow puncture forming member 150 may be replaced and disposed of as desired while reusing the remaining assembly 300 component parts.

Figure 26:
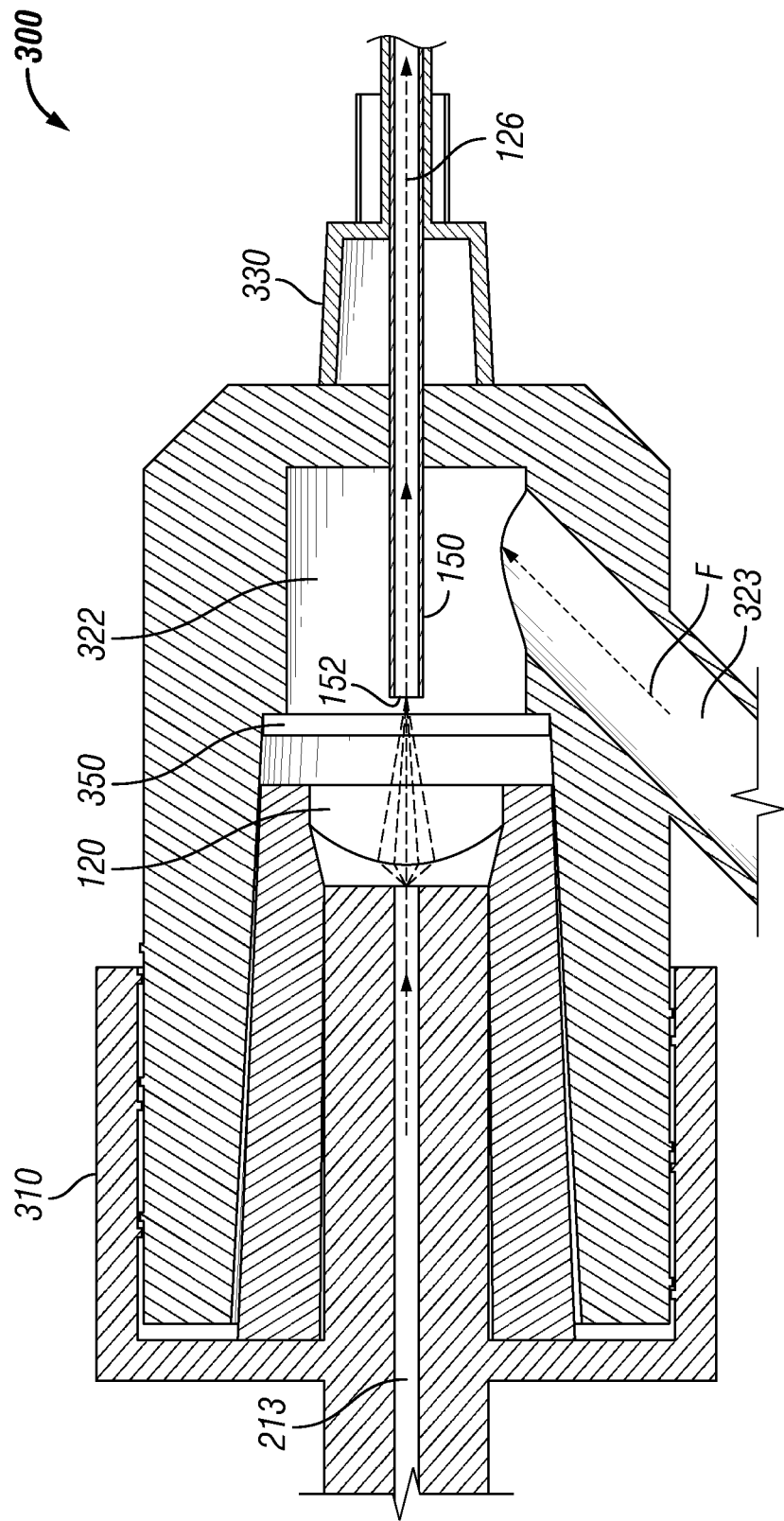
FIG. 26 illustrates a partial sectional view of a treatment assembly of the present application including a waveguide and hollow member attached thereto illustrating propagation and transformation of electromagnetic radiation through the treatment device.

Turning to FIG. 26, in operation electromagnetic radiation 125 may be conveyed through the core 213 of the waveguide member 310 and an optical interface 120, which is operationally configured to transform the electromagnetic energy 125 in a manner effective to convey transformed electromagnetic radiation 126 into the proximal end 152 of the hollow puncture forming member 150, whereby the hollow puncture forming member 150 is operationally configured to receive electromagnetic radiation 126 and fluid or a fluid solution received from fluid inlet 323 (according to exemplary Arrow F) in a manner effective for the hollow puncture forming member 150 to act in a similar manner as a liquid light guide for delivering radiant energy to one or more target sites, including a therapeutic amount of radiant energy and/or fluid or a fluid solution. As shown in FIG. 26, at least part of the central axis of the waveguide member 310 is substantially aligned with the central axis of the hollow puncture forming member 150.

Turning to FIGS. 27-32, another treatment assembly 400 is provided. As shown in the simplified exploded view FIG. 27, the treatment assembly 400 suitably includes three main components, namely (1) a cable member 401, (2) an interconnect member 402 and (3) a hollow dispensing member 403. The cable member 401 is in radiant communication with electromagnetic radiation source 100 and the interconnect member 402. The interconnect member 402 is further in radiant communication with the hollow dispensing member 403 and in fluid communication with a fluid source 104. The hollow dispensing member 403 is operationally configured to provide an exit point of electromagnetic radiation and/or one or more fluids or fluid solutions out from the treatment assembly 400.

Figure 29:
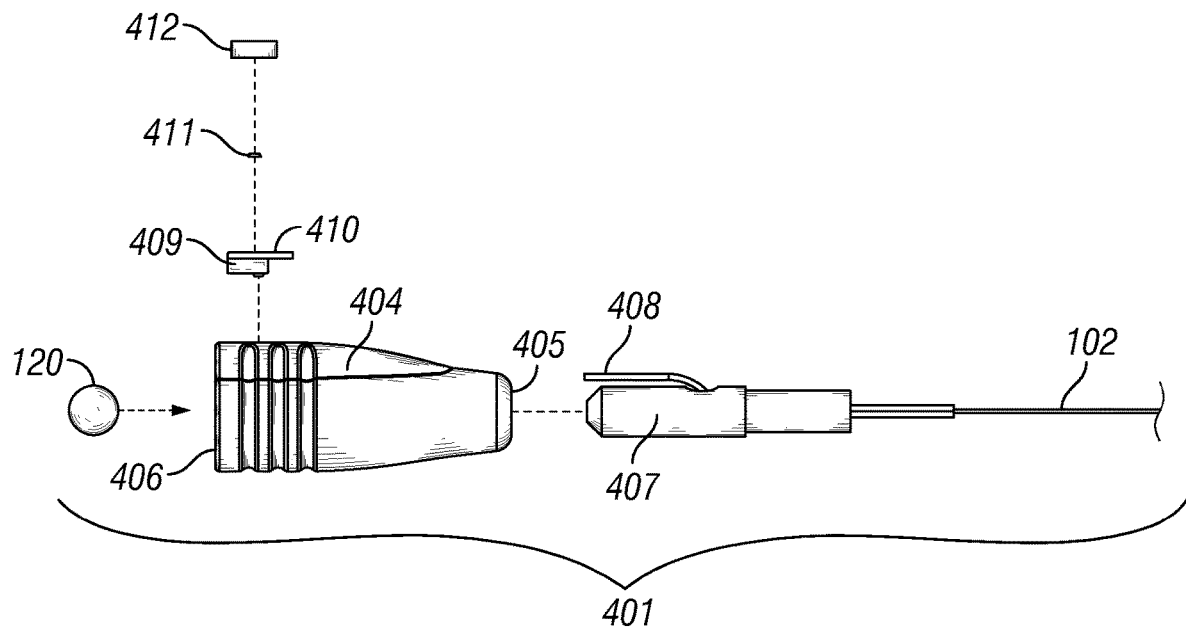
FIG. 29 illustrates an exploded view of an exemplary cable member and a waveguide.

With attention to FIG. 28, the cable member 401 is operationally configured to receive a waveguide 102 in radiant communication therewith. In this particular embodiment, the cable member 401 includes an overmold member 404 with a first opening or port 405 operationally configured to mate with a terminal end of a waveguide 102, e.g., a termination ferrule 407, and a second opening or port 406 operationally configured to mate with the interconnect member 402. Without limiting the invention, a suitable cable member 401 may further include the following component parts: (1) an electrical connector 409, (2) a printed circuit board ("PCB") 410, (3) one or more light emitting diodes ("LED") 411 and (4) a window member 412. An exploded view of an embodiment of the cable member 401 and waveguide 102 is depicted in FIG. 29.

Suitably, the inner surface of the opening 405 corresponds in size and shape to at least part of the termination ferrule 407 (and interference member 408 attached thereto)—providing a close fit between the termination ferrule 407 and the overmold member 404. In suitable operation, the waveguide 102 is held in place via the termination ferrule 407 and the termination ferrule 407 and one or more optical interfaces 120 are held in place via the overmold member 404. In one embodiment, optical interfaces 120 may be machine fit, pressed within the cable member 401 after molding or overmolded into the overmold member 404. In another embodiment, the configuration of the opening 405 and optical interfaces 120 may allow an optical interface 120 to be held in a static position during assembly 400 operation.

As shown, the optical interface 120 is disposed across the entire opening 405 eliminating electromagnetic radiation from propagating around the optical interface 120.

As further shown in FIG. 28, a suitable interconnect member 402 includes (1) a main body 420, (2) an opening 421, (3) a window member 422 suitably transparent at corresponding electromagnetic frequencies, (4) an integrated circuit ("IC") 424, (5) a fluid opening 426, (6) a cavity 427 in fluid communication with the fluid opening 426, (7) a nose 429, e.g., a tapered nose, having an outlet 428 in fluid communication with the cavity 427 and in radiant communication with the cable member 401 and (8) a connection member 430 attachable to the main body 420. In operation, the main body 420 is mated to the cable member 401 via opening 406. For example, the main body 420 may be mated to the cable member 401 via a snap fit connection including, but not necessarily limited to a detent type snap action built into the main body 420 and cable member 401. The interconnect member 402 is further depicted in the simplified illustrations of FIGS. 30A-30D.

Figure 30A:
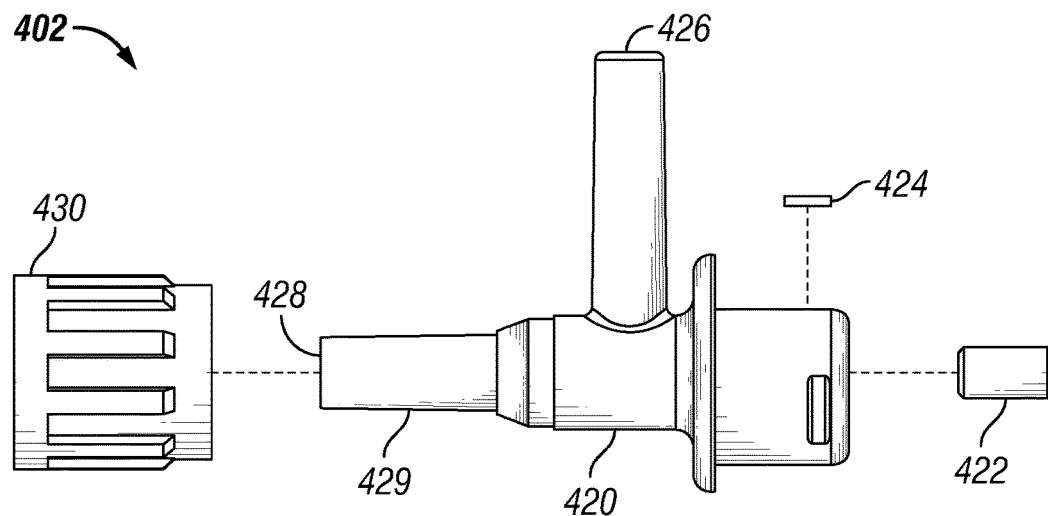
FIG. 30A illustrates an exploded view of an exemplary interconnect member.
Figure 30B:
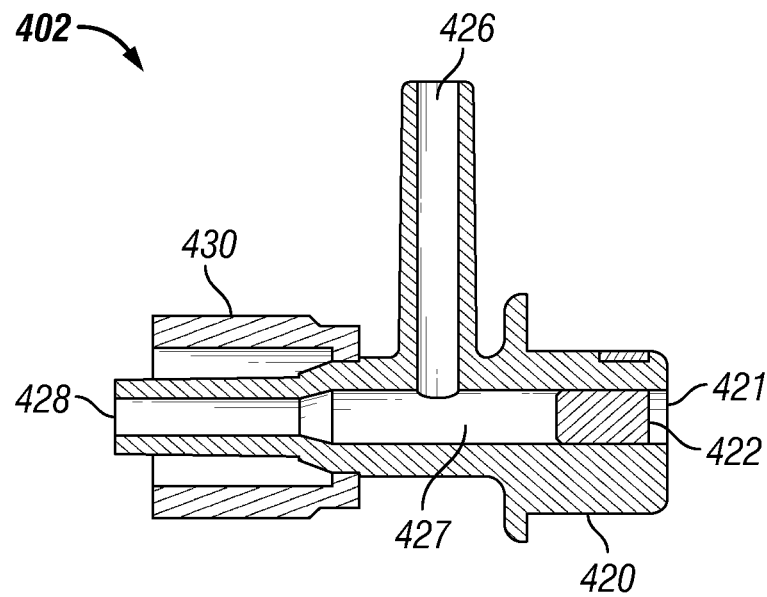
FIG. 30B illustrates a sectional side view of the interconnect member of FIG. 30A.
Figure 30C:
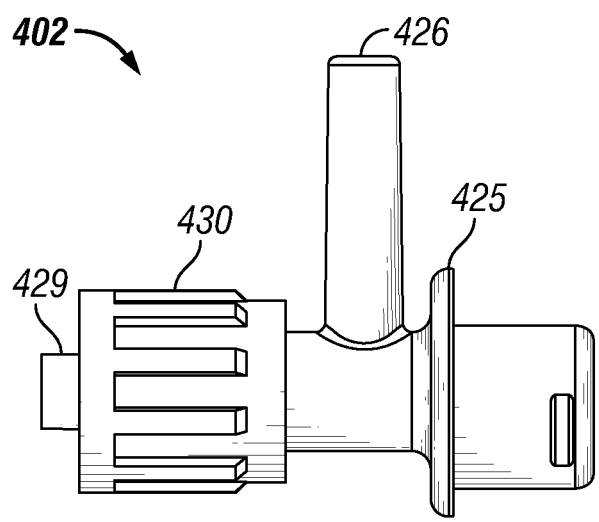
FIG. 30C illustrates a side view of the interconnect member of FIG. 30A.
Figure 30D:
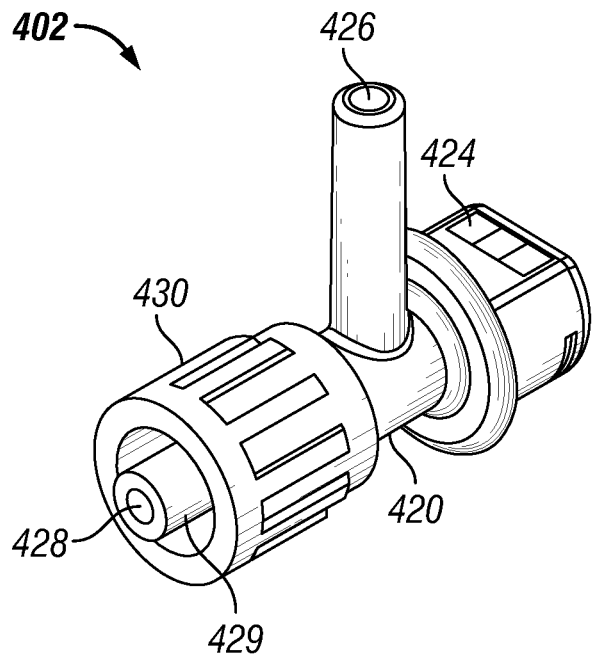
FIG. 30D illustrates a perspective view of the interconnect member of FIG. 30A.
Figure 31:
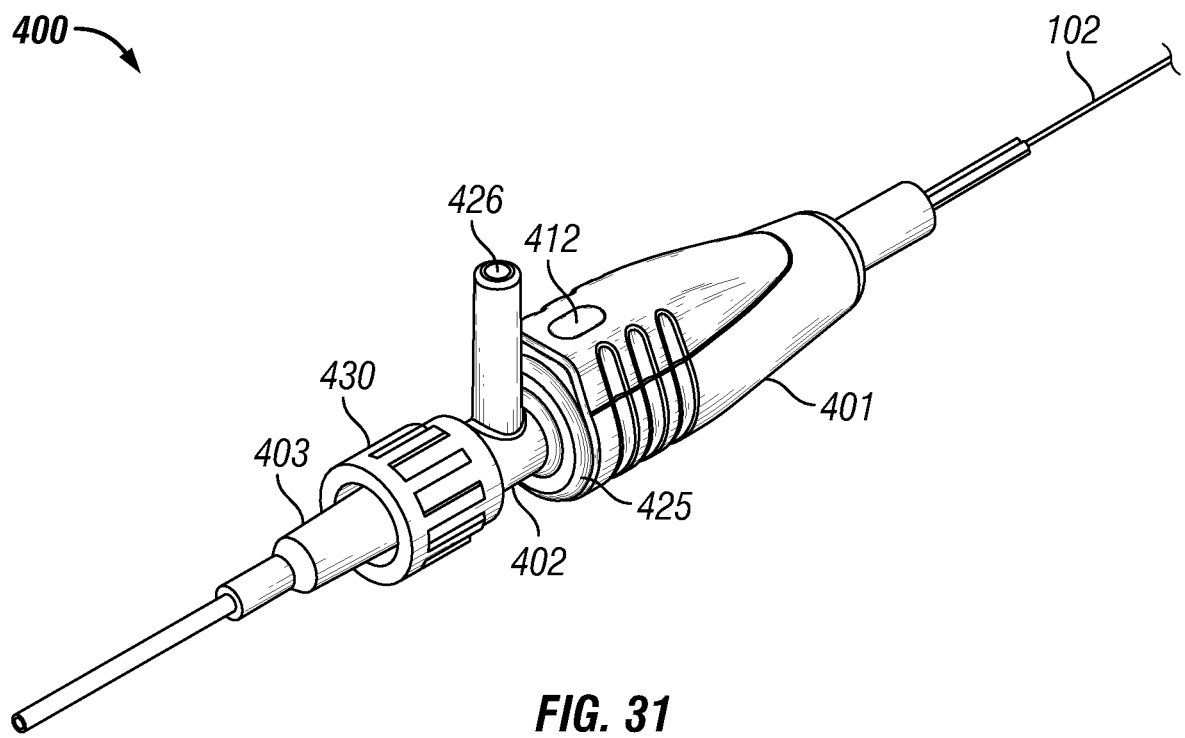
FIG. 31 illustrates a perspective view of an assembly of the present application.

Again referring to FIG. 28, a hollow dispensing member 403 suitably includes a hub 440 having an inlet 441 and a hollow member 150 attached thereto having an outlet at its open tip 151—the hollow member 150 being in communication with the hub 440. As discussed above, the type of hollow member 150 that may be employed is not limited to any one particular embodiment. As depicted in FIG. 28, a suitable hollow dispensing member 403 is releasably attachable to the connection member 430. In one simplified embodiment, the connection member 430 may include a Luer lock type device and the hollow dispensing member 403 may include a Luer lock needle operationally compatible with the Luer lock 430 as understood by the skilled artisan. With reference to FIGS. 30D and 31, the hub 440 of a Luer lock needle is operationally configured to fit onto the outer surface of the nose 429 along the inner perimeter of the Luer lock 430. An exemplary blunt Luer lock needle is shown in FIG. 27. An exemplary sharp Luer lock needle is shown in FIG. 28. As also understood by the skilled artisan, Luer lock needles and other dispensing hollow members are typically disposable items—the hollow member 150 often being constructed from stainless steel and the hub 440 often being constructed from plastic including, but not necessarily limited to polypropylene. As discussed above, other hollow members 150 may be used, e.g., a catheter or flexible catheter tube. An example of a suitable Luer lock 430 is commercially available on the internet at www.qosina.com.

Figure 32:
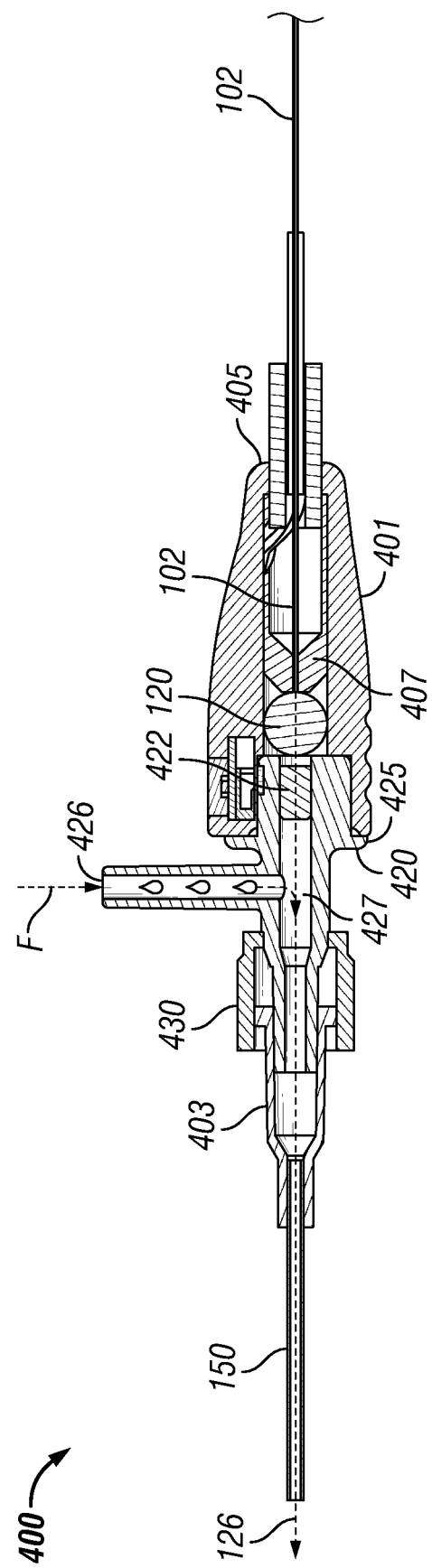
FIG. 32 illustrates a sectional side view of the assembly of FIG. 31.

Turning to FIG. 32, the longitudinal axis of the waveguide 102, cavity 427 and hollow member 150 of the treatment assembly 400 are axially aligned. In addition, the center of the optical interface 120 is substantially aligned with the longitudinal axis of each. In operation, the termination ferrule 407 is connected to the cable member 401 in a manner whereby the distal end of the waveguide 102 is set a predetermined distance (also may be referred to as a precise distance, because distance may affect the focus, e.g., the collimation, of electromagnetic radiation into fluid in the interconnect member 402) from the optical interface 120 thereby minimizing the distance of propagation of electromagnetic radiation between the waveguide 102 and the optical interface 120. Although the treatment assembly 400 may built to scale, in one suitable embodiment the distal end of the waveguide 102 may lie from a position of abutment with the optical interface 120 up to a precise distance apart from the optical interface 120 during assembly 400 operation.

As described above, the main body 420 suitably mates with the cable member 401 in a manner effective to minimize the distance of propagation of electromagnetic radiation between the optical interface 120 and the opening 421 of the interconnect member 402 in a manner effective to maximize energy transfer from the waveguide 102 through the hollow dispensing member 403. As shown in FIGS. 31 and 32, the distal end of the overmold member 404 suitably abuts a rim 425 disposed along the main body 420 when the component parts are assembled for operation. In one suitable embodiment, the opening 421 of the interconnect member 402 may lie from a position of abutment with the optical interface 120 up to a predetermined apart from the optical interface 120 during assembly 400 operation. This distance suitably has no effect on assembly 400 operation. It is further contemplated that the inner surface of the opening 421 may be coated with one or more anti-reflective optical coatings in a manner effective to negate reflection losses of electromagnetic radiation.

As light propagates from an electromagnetic radiation source 100 (see for example FIG. 1) through a waveguide 102, the numerical aperture of the waveguide 102 defines the exit angle of electromagnetic radiation from the waveguide 102 as the electromagnetic radiation interfaces the optical interface, e.g., lens, 120. As electromagnetic radiation 126 enters the opening 421, the electromagnetic radiation 126 propagates through the window member 422 continuing through the cavity 427 and hollow member 150 exiting out there from toward a target site. A suitable window member 422 may be constructed from one or more materials including, but not necessarily limited to glass, synthetic quartz, polymeric material, e.g., sapphire, and combinations thereof. In one embodiment, the window member 422 may be machine fit, pressed in after molding within the interconnect member 402 or overmolded into the interconnect member 402 as desired. In another embodiment, the configuration of the inner surface of the opening 421 and the window member 422 may allow a window member 422 to be held in a static position during assembly 400 operation. As shown, a suitable window member 422 is disposed across the entire opening 421 sealing off the cavity 427 in a manner whereby electromagnetic radiation cannot propagate around the window member 422 and fluid cannot flow beyond the window member 422 toward the optical interface 120. In particular, the interconnect member 402, via window member 422, is operationally configured to isolate the waveguide 102, optical interface 120 and the air space adjacent the optical interface 120 from fluid or fluid solutions delivered to the optical interface 120 via fluid opening 426 (see Arrow F). In addition, the interconnect member 402, via window member 422, is operationally configured to isolate the waveguide 102 from the hollow dispensing member 403.

When assembled, the IC 424, e.g., an encryption IC, or authentication IC as the terms are known by persons of ordinary skill in the art, is suitably attached to the surface of the main body 420 or to a depression along the main body 420 via one or more adhesive materials such as epoxy or the like. In operation, when the main body 420 is mated with the second opening 406 of the cable member 401, the IC 424 interfaces the electrical connector 409 of the cable member 401, which is held intact via the PCB 410. Suitably, the IC 424 electronically communicates assembly 400 operating information to the electrical connector 409 and PCB 410, which in turn may electrically communicate operating information to one or more LED 411 attached to the PCB 410 and/or to the electromagnetic radiation source 100. In a simplified mode of operation, the assembly 400 may be protected against counterfeiting of component parts whereby, to initiate use of the assembly 400, the IC 424 must electronically communicate with the electromagnetic radiation source 100 to validate authenticity of the interconnect member 402 before the electromagnetic radiation source 100 may be operated. As understood by the skilled artisan, one or more of the assembly 400 component parts and/or the electromagnetic radiation source 100 may be programmed as desired. Suitably, PCB 410 communicates with the electromagnetic radiation source 100 via wiring. Without limiting the invention, small gauge wiring from about 0.00501 $mm^2$ to about 0.0320 $mm^2$ (from about 40 AWG to about 32 AWG) may be used. In addition, wireless communication between the assembly 400 and the source 100 may also be employed as desired, e.g., via radio-frequency identification ("RFID").

In one suitable embodiment, the assembly 400 may include two or more colored LED 411 for indicating various operation information as desired. For example, one red LED and one blue LED may be used to indicate certain operation information to one or more persons through the window member 412 (see for example FIG. 31). In a non-limiting example of the assembly 400 including the conveyance of light there through, a blinking red LED may indicate a fault, a blinking blue LED may indicate active UV propagation and a solid red LED may indicate active visible light propagation. A suitable window member 412 may be constructed from glass, one or more polymeric materials, synthetic quartz, and combinations thereof. In addition, the window member 412 may be form fit within an opening on the main body 420, held in place via one or more adhesive materials or snap fit as desired.

Without limiting the means of production, a suitable overmold member 404 and main body 420 may be formed via molds, e.g., injection molding, overmold member 404 and the main body 420 being constructed from one or more materials as described below. For human use, one or more bio-approved polymeric materials may be used to construct the overmold member 404 and main body 420 as desired. For example, in the United States of America, one or more bio-approved polymeric materials may include materials as approved by the United States Food and Drug Administration ("FDA") at such time. In addition, the overmold member 404 and/or the interconnect member 402 may be reused or disposable following a single use as desired or as otherwise required.

As understood by the skilled artisan, the treatment device 106 and assemblies 200, 300, 400 discussed above may be constructed from any material durable enough to perform one or more treatments over one or more durations as described herein. In particular, the treatment device 106 and assembly component parts may be constructed of materials including but not necessarily limited to those materials resistant to chipping, cracking, excessive bending and reshaping as a result of ozone, weathering, heat, moisture, other outside mechanical and chemical influences, as well as various impacts and other loads placed on the treatment device 106 and assembly component parts. Likewise, the treatment device 106 and assembly component parts may be constructed from one or more materials durable enough to withstand one or more of boiling, autoclaving, dry heat sterilization, flaming, detergent washing, bathing via an acid bath and combinations thereof for purposes of reuse of the treatment device 106 and assembly component parts. Also, the treatment device 106 and assembly component parts may comprise any color or combination of colors, or in the alternative, the treatment device 106 may be wholly or partly transparent and translucent depending on individual preferences and needs.

Suitable treatment device 106 and assembly component parts materials may include, but are not necessarily limited to metals, polymeric materials, rubbers, glass, plexiglass, filled composite materials, woods, minerals, and combinations thereof. Suitable polymeric materials may include, but are not necessarily limited to thermoplastics, synthetic plastics, semi-synthetic organic plastics, and combinations thereof. Exemplary plastics may include, but are not necessarily limited to nylon, vinyl polymers and polyvinyl chloride ("PVC"), polyethylene, polyethylene terephthalate ("PET"), polymethylpentene, polypropylene, polycarbonate, and combinations thereof. In one particular embodiment, the treatment device 106 and assembly component parts may be constructed from one or more polymeric materials and one or more pro-degradant additives effective to provide a degradable treatment device 106 and assembly component parts. Suitable pro-degradant materials may include, but are not necessarily limited to one or more transition metal salts. Without limiting the invention to a particular mode, the treatment device 106 and assembly component parts may be produced via one or more processes including, but not necessarily limited to assembly of various parts, injection molding, blow molding, thermoforming, rotational molding, compression molding, three-dimensional printing, film and sheet extrusion, and pipe and cable extrusion as each is understood by a skilled artisan.

A suitable waveguide 102 or radiant energy conduit is effective to guide or otherwise convey electromagnetic radiation there through at one or more rates of attenuation as desired. For the purposes of this application, suitable waveguides 102 may include, but are not necessarily limited to liquid light guides, glass optical fibers, plastic optical fibers, photonic-crystal fibers ("PCF"), and combinations thereof. Suitable liquid light guides may include any desired liquid transmissive fluid encapsulated therein as desired. For the purposes of this application, liquid light guides are operationally configured to convey radiant energy from about 200 nm to about 2000 nm. Suitable glass optical fibers may be constructed from materials including, but not necessarily limited to silica glass, e.g., germanosilicate or aluminosilicate glass, fluoride glass, e.g., fluorozirconate and fluoroaluminate, chalcogenide glass, phosphate glasses, crystalline materials such as sapphire, and combinations thereof. Suitable plastic optical fibers may be constructed from materials including, but not necessarily limited to poly (methyl methacrylate) ("PMMA"). For conveying radiant energy to a subsurface or subcutaneous location of an animal, a suitable waveguide 102 has an attenuation coefficient of about 0.5 dB/m or lower. Without limiting the invention to a particular mode of operation, one suitable waveguide 102 includes a fused silica UV grade fiber commercially available from Molex, Inc., which may be located on the internet at the following address: www-.molex.com.

Without limiting the invention, optical fibers may further be described according to the following:

Fiber couplers may be employed to couple radiant energy between two fibers, typically with the coupling coefficient depending on the optical wavelength;

As understood by the skilled artisan Fiber Bragg gratings may be employed to provide various wavelength-dependent reflection and transmission properties—such may be used as optical filters or for introducing chromatic dispersion into a system;

Fiber polarizers may be employed for guiding only electromagnetic radiation with a certain polarization direction;

Fiber amplifiers may be employed for amplifying electromagnetic radiation in certain wavelength regions;

Various types of optical modulators such as electroabsorption modulators and electro-optic modulators may be employed;

Faraday isolators, optical isolators, or optical diodes, may be employed including the us of collimation optics;

Fiber-optic switches as understood by the skilled artisan may be employed;

Mechanical splices may be employed as desired;

Double-clad fibers may be employed as desired; and

Polarization-maintaining fibers and photonic crystal fibers may be employed as desired.

As desired, one or more connections may be employed to assist in the conveyance of electromagnetic radiation from the electromagnetic radiation source 100 to the waveguide 102 and to the treatment device 106 or assemblies 200, 300, 400. Suitable connections may be operationally configured to engage each of the electromagnetic radiation source 100, waveguide 102 and treatment device 106 in a manner effective to maintain substantially all of the electromagnetic radiation within the system components free of leakage thereof during operation. The connections may include optical fiber connectors, optical fiber couplers, luer fittings or adapters, ferrule connectors, compression fittings, and combinations thereof. As one simplified example, the conduit 134 in FIG. 14A may include a luer-lock connector 137 and cap 138 for receiving a fluid conduit 107 in fluid communication thereto. Suitable optical fiber connectors include, but are not necessarily limited to FC connectors, E2000 connectors, LuxCis connectors, SMA 905 connectors, ST connectors, and TOSLINK connectors as each are understood by the skilled artisan. Suitable connections may be constructed from metals, polymeric materials, rubbers, glass, plexiglass, filled composite materials, and combinations thereof. Metal connection materials may include, but are not necessarily limited to stainless steel, brass, nickel-plated brass, aluminum, copper, and combinations thereof. Plastic connection materials may include nylon, vinyl polymers and polyvinyl chloride ("PVC"), polyethylene, polyethylene terephthalate ("PET"), polymethylpentene, polypropylene, polycarbonate, and combinations thereof.

The electromagnetic radiation source 100, as shown in FIGS. 1 and 2, may derive radiant energy from one or more sources as desired. Suitable sources of radiant energy may include, but are not necessarily limited to (1) one or more incandescent lamps or bulbs (which can have one or more rotating filters around each bulb), (2) one or more semiconductor light sources (including but not necessarily limited to light-emitting diodes "LED"), (3) one or more diode laser lights, (4) one or more quartz-halogen lights, (5) one or more gas-discharge lamps, and combinations thereof. A suitable electromagnetic radiation source 100 is operationally configured to produce electromagnetic radiation across the entire electromagnetic spectrum. Without limiting the invention to a particular embodiment, the electromagnetic radiation source 100 may be self-powered, e.g., battery power, or powered by an external source, e.g., a wall outlet and the like.

Without limiting the application to a particular embodiment, the electromagnetic radiation source 100 of the present application may include an electromagnetic radiation source 100 as described in U.S. patent applications Ser. No. 11/686,767 filed on Mar. 15, 2007 or U.S. patent application Ser. No. 13/783,387 filed on Mar. 3, 2013, which are hereby incorporated by reference in their entirety. A suitable electromagnetic radiation source 100 may include one or more of the following components:

(1) UV LEDS: The main LED may include a high power 365 nm version as commercially available from Nichia Corporation. To fill in lower wavelength UV energy UVTOP LEDs may be used in wavelengths from about 295 nm to about 310 nm. Such LEDs are commercially available from Sensor Electronic Technology, Inc. Suitably, light is coupled from each of these LED sources directly into a 600 um fiber or the like. This is done via a process using a ball-lensed fiber that uses a precision 3-axis stage to optimize the coupling. Each LED and fiber assembly is connected into an SMA 905 fiber optic connector (as understood by the skilled artisan) so that individual LEDs can be serviced as necessary;

(2) UV Fiber Optics: One suitable fiber may include a 600 um core size. The fibers are terminated in a "Y" fashion. Such design allows close to about 50.0% of the fiber coupled from each fiber to be coupled into the next fiber. Such configuration results in about 25.0% of the optical power from each LED making it to the beam splitter as such is understood by the skilled artisan. Mechanical and optical data for suitable fibers, including Polymicro optical fibers, is commercially provided by Molex Incorporated;

(3) Fused Silica UV Lenses (inside a collimator): The light emitted from the fiber is collimated for transmission through the beam-splitter. There is a reciprocating collimator on the output side of the beam-splitter used to focus the light back into the output fiber. Information on the UV grade fused silica and plano convex lenses that may be employed herein is commercially available from Edmund Optics, Inc.;

(4) UV Short Pass Filter: A dichroic filter may be used to combine the visible LED and UV-LEDs. Suitably, the wavelengths that are not transmitted are reflected;

(5) Visible LED and LED optic: As understood by the skilled artisan a CREE Cool White LED may be used as is commercially available from Cree, Inc. Another bright single die LED may be used as desired. Suitably, an acrylic injection molded lens is used to collimate the light from the LED, this reflects from the beam-splitter and is focused into the output fiber; and (6) Feedback Photodiode: A feedback photodiode may be used to measure the output of the UV-LEDs and calibrate the power output prior to every usage or treatment using the radiation source. As understood by the skilled artisan, the photodiode receives a small reflection from the beam splitter.

Figure 33:
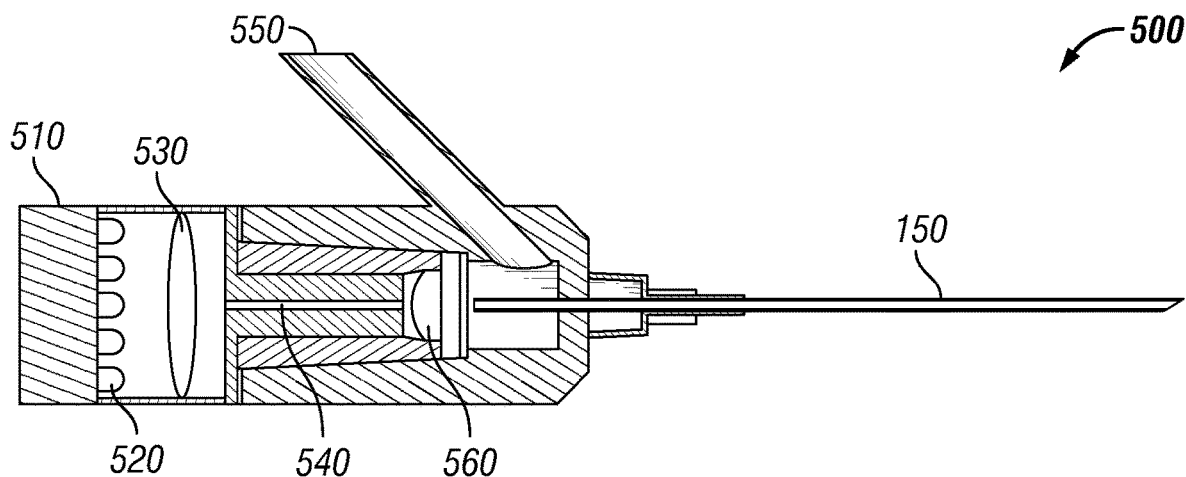
FIG. 33 illustrates a sectional side view of another simplified embodiment of a treatment device of the present application.

FIG. 33 illustrates a first non-limiting "all in one" type self-powered treatment device 500 operationally configured to produce and convey electromagnetic radiation and fluid to one or more target sites. In this simplified illustration, the treatment device 500 includes a power source 510, an electromagnetic radiation source 520, one or more optical interfaces 530 for transforming electromagnetic radiation entering the waveguide 540, a fluid inlet 550 and at least a second optical interface 560 used alone or with another window type member similar to the embodiments described above, e.g., effective for sealing off fluid flow toward the one or more optical interfaces 530. In one embodiment, the electromagnetic radiation source 520 may include a single radiant energy source, an LED array, or array of other radiant energy sources as desired. In suitable operation, the treatment device 500 is operationally configured to convey electromagnetic radiation and/or one or more fluids or fluid solutions out through the distal end of the hollow member or hollow puncture forming member 150 that is in radiant and fluid communication thereto. In another embodiment, other optic configurations including those described above may be employed into the present treatment device 500. In another embodiment it is also contemplated that the treatment device 500 be powered via a power cord similar to other electronic appliance type devices and the like. In another embodiment, the treatment device 500 may include a fluid storage compartment in fluid communication with the hollow member 150. The treatment device 500 may be operationally configured to make use of disposable type hollow members or hollow puncture forming members 150 as described herein.

Figure 34:
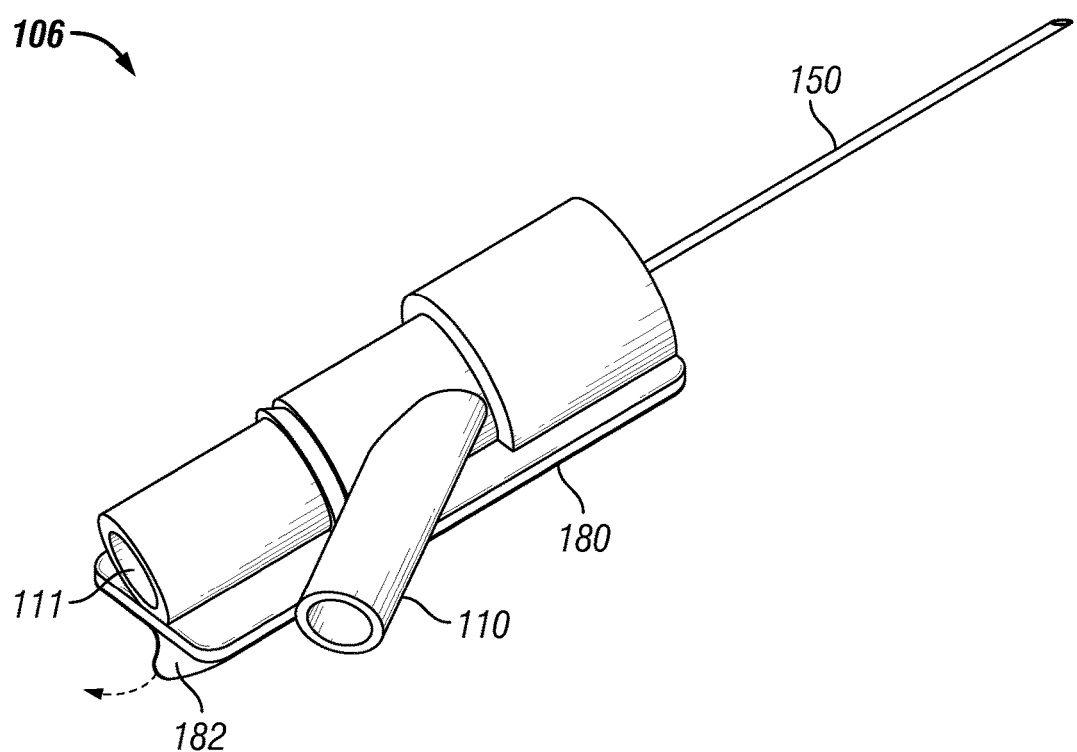
FIG. 34 illustrates a perspective view of another simplified embodiment of a treatment assembly of the present application.

Turning now to the simplified illustration of a treatment device 106 in FIG. 34, it is further contemplated that one or more outer surfaces of the treatment device 106 may include a mating type surface for contacting the treatment device 106 with one or more target surfaces. Such surfaces may include one or more shapes or surface configurations as desired. For example, a treatment device 106 may include a curved surface operationally configured to be set atop a curved target surface. Such surfaces may also include one or more raised surface portions raised above adjacent areas for providing a slip-resistant surface. In the embodiment of FIG. 34, the treatment device 106 is shown as having a substantially planar mating surface. As further illustrated in FIG. 34, the mating surface may include one or more adhesives providing an adhesive type surface 180 covered by a peelable layer 182. In an embodiment where the treatment device 106 of FIG. 34 is configured for human treatment as shown in FIG. 1, it is contemplated that the adhesive type surface 180 may be placed onto the skin of a person's arm whereby the adhesive material is operationally configured to maintain the treatment device 106 in a substantially fixed position on the arm. Suitable adhesive type surfaces may include one or more tacky substances as understood by the skilled artisan. In one particular embodiment, removal of the treatment device 106 from a subject's skin should not cause injury, pain or discomfort to the individual. Similar to other embodiments of the treatment device 106 and treatment assemblies, the treatment device of FIG. 34 may include two or more inlets or ports as desired for receiving electromagnetic radiation from waveguides 102 communicating with each such inlet or port. Likewise the treatment device 106 of FIG. 34 may be reusable, replacing only the hollow member or hollow puncture forming member 150 following each use of the treatment device 106.

It is further contemplated that the treatment devices and assemblies of this application may include one or more sensor type devices operationally configured to detect the spatial relationship between the sensor and a target surface of a subject. Such sensors provide a safety feature preventing operation of the treatment devices and/or treatment assemblies as desired. Suitable sensors include, but are not necessarily limited to projected field sensors, proximity sensors, projected capacitive sensors, and combinations thereof. Other suitable sensors may be described as being operationally configured to detect a target surface of a subject through a non-electrically conductive medium.

It is further contemplated that treatment devices and assemblies of this application may include one or more filter type members for filtering out solids, pathogens, and combinations thereof prior to the fluids and fluid solutions flowing to a common area of the devices and assemblies (for example see cavity 427). For example, in an emergency situation a device, assembly or system of this application including one or more filter type members may be used in a remote area making use of contaminated water as the fluid source. One suitable filter type member may be operationally configured to remove chlorine, heavy metals including aluminum, arsenic, cadmium, copper, lead, mercury, iodine, endrin, dichlorodiphenyltrichloroethane, lindane, heptachlor, polychlorinated biphenyls, atrazine, simazine, nitrite, bromodichloromethane, bromoform, benzene, dibromochloromethae, carbon tetrachloride, ethyl benzene, methyl tert butyl ether, trichloroethane, toluene, xylene, giardia, crytoporidium, *E. Coli, E. Faecalis*, and combinations thereof. In addition to the above, a suitable filter type member may also be operationally configured to provide 99.9999 percent reduction of bacteria, cysts and viruses.

In one embodiment, the application may be directed to a method of targeting an animal blood vessel with electromagnetic radiation and fluid including (1) providing an assembly including (A) a device having a first inlet for connecting to a source of electromagnetic radiation, a second inlet for connecting to a source of fluid and an outlet for emitting electromagnetic radiation and fluid received from the electromagnetic radiation and fluid sources, the device being operationally configured to transform the electromagnetic radiation received therein and isolate the fluid received therein from the electromagnetic radiation source and (B) a hollow member attached to the outlet of the device, the hollow member having an open puncture forming distal end; (2) connecting the device to an electromagnetic radiation source and a fluid source; (3) directing the distal end of the hollow puncture forming member into a blood vessel; and (4) conveying transformed electromagnetic radiation and fluid out through the distal end of the hollow member into the blood vessel. In another embodiment, the application may be directed to a device for targeting one or more sites with electromagnetic radiation, the device having a housing operationally configured to convey electromagnetic radiation and fluid there through, the housing having a first inlet for receiving electromagnetic radiation from one or more sources, a second inlet for receiving fluid from one or more sources and an outlet for emitting electromagnetic radiation and fluid received through the first and second inlets; the housing being operationally configured to fluidly seal the first inlet from the second inlet and transform electromagnetic radiation received through the first inlet.

It is believed that the devices, assemblies, systems and methods of the present application and advantages will be understood by the foregoing description. Persons of ordinary skill in the art will recognize that many modifications may be made to the present application without departing from the spirit and scope of the devices, assemblies, systems and methods. The embodiment(s) described herein are meant to be illustrative only and should not be taken as limiting the invention, which is defined in the claims.

We claim:

1. An assembly for targeting electromagnetic radiation at one or more sites including:

a first member including a first opening defined by a first inner surface operationally configured to receive electromagnetic radiation therein from an electromagnetic radiant source, a second opening defined by a second inner surface in radiant communication with the first opening, the first member having transformation optics housed therein;

a second member attachable to the first member, the second member including a first body portion defining a first opening in radiant communication with the first opening of the first member, a fluid opening, a transparent member housed within the first body portion operationally configured to fluidly seal the second member from the first member, and an outlet in radiant communication with the first opening of the first member and in fluid communication with the fluid opening; and a third member including an inlet attachable to the second member and an outlet operationally configured to emit electromagnetic radiation received by the first member and fluid received by the second member;

wherein the second opening of the first member is operationally configured to receive the first body portion of the second member in a mated position within the second opening.

2. The assembly of claim 1 wherein the transformation optics is operationally configured to transform electromagnetic radiation into one or more particular types of electromagnetic beams conveyable through the second opening of the first member, the second member and the third member without employing optical fiber for conveyance of said electromagnetic radiation there through.

3. The assembly of claim 2 wherein the first member is operationally configured to emit parallel beams of electromagnetic radiation out through the outlet of the third member.

4. The assembly of claim 3 wherein the third member is a hypodermic needle.

5. The assembly of claim 1 wherein the third member is operationally configured to receive parallel beams of electromagnetic radiation from the second member and emit said parallel beams of electromagnetic radiation out from the assembly.

6. The assembly of claim 5 wherein the third member is a hypodermic needle.

7. The assembly of claim 1 wherein the second member includes a second body portion defining the outlet of the second member and wherein the inlet of the third member includes an inner surface operationally configured to releasably attach to the second body portion of the second member.

8. The assembly of claim 1 wherein the third member includes a hub defining the inlet of the third member and a hollow member attached to the hub defining the outlet of the third member, wherein the hollow member is spaced apart from the second member.

9. The assembly of claim 1 wherein the transformation optics are disposed across the first inner surface of the first opening of the first member.

10. The assembly of claim 1 wherein the second member is in electronic communication with the first member.

11. The assembly of claim 1 wherein the first member includes an electrical connector and the first body portion of the second member includes an integrated circuit in electronic communication with the electrical connector.

12. The assembly of claim 1 wherein the third member includes a selection of hypodermic needles having a nominal outer diameter with a measurement selected from the group of measurements consisting of 4.572+ or −0.025 mm, 4.191+ or −0.025 mm, 3.759+ or −0.025 mm, 3.404+ or −0.025 mm, 3.048+ or −0.025 mm, 2.769+ or −0.025 mm, 2.413+ or −0.025 mm, 2.108+ or −0.025 mm, 1.829+ or −0.013 mm, 1.651+ or −0.013 mm, 1.473+ or −0.013 mm, 1.270+ or −0.013 mm, 1.067+ or −0.013 mm, 0.9081+ or −0.0064 mm, 0.8192+ or −0.0064 mm, 0.7176+ or −0.0064 mm, 0.6414+ or −0.0064 mm, 0.5652+ or −0.0064 mm, 0.5144+ or −0.0064 mm, 0.4636+ or −0.0064 mm, 0.4737+ or −0.0064 mm, 0.4128+ or −0.0064 mm, 0.3620+ or −0.0064 mm, 0.3366+ or −0.0064 mm, 0.3112+ or −0.0064 mm, 0.2604+ or −0.0064 mm, 0.2350+ or −0.0064 mm, 0.2096+ or −0.0064 mm, and 0.1842+ or −0.0064 mm.

13. An assembly of interchangeable component parts for operation in targeting electromagnetic radiation at one or more sites including:

a first component part having an electromagnetic radiation inlet, an electromagnetic radiation outlet, and one or more optical interfaces operationally configured to transform electromagnetic radiation into one or more particular types of electromagnetic beams to be emitted out from the electromagnetic radiation outlet;

a second component part in radiant communication with the first component part, the second component part having a fluid inlet operationally configured to receive fluid into the second component part, a transparent member for fluidly sealing the second component part from the first component part, and an outlet; and a third component part in communication with the second component part, the third component part having an outlet operationally configured to emit electromagnetic radiation received by the first component part and fluid received by the second component part;

wherein the size of the second component part and the size of the third component part are determined according to a particular operation from amongst a selection of second component parts and third component parts.

14. The assembly of claim 13 wherein the third component part includes a selection of hypodermic needles having a nominal outer diameter with a measurement selected from the group of measurements consisting of 4.572+ or −0.025 mm, 4.191+ or −0.025 mm, 3.759+ or −0.025 mm, 3.404+ or −0.025 mm, 3.048+ or −0.025 mm, 2.769+ or −0.025 mm, 2.413+ or −0.025 mm, 2.108+ or −0.025 mm, 1.829+ or −0.013 mm, 1.651+ or −0.013 mm, 1.473+ or −0.013 mm, 1.270+ or −0.013 mm, 1.067+ or −0.013 mm, 0.9081+ or −0.0064 mm, 0.8192+ or −0.0064 mm, 0.7176+ or −0.0064 mm, 0.6414+ or −0.0064 mm, 0.5652+ or −0.0064 mm, 0.5144+ or −0.0064 mm, 0.4636+ or −0.0064 mm, 0.4737+ or −0.0064 mm, 0.4128+ or −0.0064 mm, 0.3620+ or −0.0064 mm, 0.3366+ or −0.0064 mm, 0.3112+ or −0.0064 mm, 0.2604+ or −0.0064 mm, 0.2350+ or −0.0064 mm, 0.2096+ or −0.0064 mm, and 0.1842+ or −0.0064 mm.

15. The assembly of claim 13 wherein the third component part includes a hollow member with a closed tip and the outlet of the third component part includes at least one aperture located near the closed tip.

* * * * *